(12) United States Patent
Yoshida et al.

(10) Patent No.: US 9,837,612 B2
(45) Date of Patent: Dec. 5, 2017

(54) POLYMER COMPOUND AND LIGHT-EMITTING DEVICE USING SAME

(75) Inventors: Tomoyasu Yoshida, Cambridgeshire (GB); Kazunori Iwakura, Osaka (JP)

(73) Assignee: SUMITOMO CHEMICAL COMPANY, LIMTED, Tokyo (JP)

(*) Notice: Subject to any disclaimer, the term of this patent is extended or adjusted under 35 U.S.C. 154(b) by 645 days.

(21) Appl. No.: 13/995,226

(22) PCT Filed: Dec. 21, 2011

(86) PCT No.: PCT/JP2011/079592
§ 371 (c)(1),
(2), (4) Date: Jun. 18, 2013

(87) PCT Pub. No.: WO2012/086668
PCT Pub. Date: Jun. 28, 2012

(65) Prior Publication Data
US 2013/0284985 A1    Oct. 31, 2013

(30) Foreign Application Priority Data

Dec. 21, 2010 (JP) .............. P2010-284963
Apr. 27, 2011 (JP) .............. P2011-100023

(51) Int. Cl.
| H01L 51/54 | (2006.01) |
| C09K 11/06 | (2006.01) |
| H01L 51/00 | (2006.01) |
| C07C 211/61 | (2006.01) |
| C08G 61/12 | (2006.01) |
| H01L 51/50 | (2006.01) |

(52) U.S. Cl.
CPC ........ *H01L 51/0043* (2013.01); *C07C 211/61* (2013.01); *C08G 61/12* (2013.01); *H01L 51/0039* (2013.01); *C08G 2261/124* (2013.01); *C08G 2261/3142* (2013.01); *C08G 2261/3162* (2013.01); *C08G 2261/342* (2013.01); *C08G 2261/411* (2013.01); *C08G 2261/5222* (2013.01); *C08G 2261/95* (2013.01); *H01L 51/5012* (2013.01); *Y02E 10/549* (2013.01)

(58) Field of Classification Search
CPC ......... C07C 25/00; C07C 25/18; C07C 25/22; C07C 211/61; C07C 2103/00; C07C 2103/90; C07C 2103/91; C07C 2103/22; C07C 2103/26; C08G 61/00; C08G 61/02; C08G 61/10; C08G 61/12; C08G 61/122; C08G 2261/00; C08G 2261/12; C08G 2261/124; C08G 2261/30; C08G 2261/31; C08G 2261/314; C08G 2261/3142; C08G 2261/3162; C08G 2261/316; C08G 2261/34; C08G 2261/342; C08G 2261/40; C08G 2261/411; C08G 2261/412; C08G 2261/5222; C08G 2261/95; C09K 11/06; C09K 2211/14; C09K 2211/1408; C09K 2211/1416; C09K 2211/1425; C09K 2211/1441; C09K 2211/145; C09K 2211/1458; C09K 2211/1466; C09K 2211/1475; C09K 2211/1483; C09K 2211/1491; H01L 51/0032; H01L 51/0034; H01L 51/0035; H01L 51/0038; H01L 51/0039; H01L 51/0043; H01L 51/50; H01L 51/5012; H01L 51/5016; H01L 51/5048; H01L 51/5052; H01L 51/5056; H01L 51/506; H01L 51/5072; H01L 51/5076; Y02E 10/549
USPC ....... 428/690, 691, 917, 411.4, 337; 427/58, 427/66; 313/500–512; 257/40, 88–104, 257/E51.001–E51.052; 252/301.16–301.35, 500; 526/239; 570/183
See application file for complete search history.

(56) References Cited

U.S. PATENT DOCUMENTS 4,356,429 A    10/1982  Tang
4,539,507 A     9/1985  VanSlyke et al.
(Continued)

FOREIGN PATENT DOCUMENTS

CN    101209988 A    7/2008
CN    101654399 A    2/2010
(Continued)

OTHER PUBLICATIONS

Machine translation of TW I394770. Date of publication: May 1, 2013.*

(Continued)

*Primary Examiner* — Andrew K Bohaty
(74) *Attorney, Agent, or Firm* — Panitch Schwarze Belisario & Nadel LLP

(57) ABSTRACT

A polymer compound having a constitutional unit represented by the following formula (1):

(1)

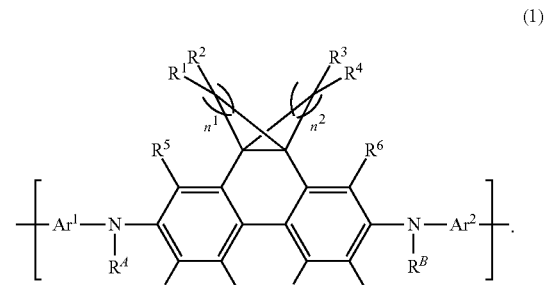

24 Claims, 3 Drawing Sheets

(56) References Cited

U.S. PATENT DOCUMENTS

| | | | |
|---|---|---|---|
| 4,990,634 A | 2/1991 | Mukai et al. | |
| 5,011,757 A | 4/1991 | Akasaki et al. | |
| 5,028,505 A | 7/1991 | Akasaki et al. | |
| 5,121,029 A | 6/1992 | Hosokawa et al. | |
| 6,416,887 B1 | 7/2002 | Tokito et al. | |
| 2004/0062930 A1* | 4/2004 | Roberts | B41M 5/395 428/411.1 |
| 2004/0109955 A1 | 6/2004 | Kitano et al. | |
| 2004/0146743 A1* | 7/2004 | O'Dell | C08G 73/02 428/690 |
| 2004/0158017 A1 | 8/2004 | O'Dell et al. | |
| 2005/0176952 A1 | 8/2005 | Tuan et al. | |
| 2005/0176953 A1 | 8/2005 | Tuan et al. | |
| 2007/0060736 A1 | 3/2007 | Becker et al. | |
| 2008/0102312 A1 | 5/2008 | Parham et al. | |
| 2009/0142876 A1 | 6/2009 | Tuan et al. | |
| 2010/0227974 A1 | 9/2010 | Schulte et al. | |
| 2011/0118411 A1 | 5/2011 | Anryu et al. | |

FOREIGN PATENT DOCUMENTS

| | | |
|---|---|---|
| JP | S57-051781 A | 3/1982 |
| JP | S59-194393 A | 11/1984 |
| JP | S63-070257 A | 3/1988 |
| JP | S63-175860 A | 7/1988 |
| JP | H02-135359 A | 5/1990 |
| JP | H02-135361 A | 5/1990 |
| JP | H02-209988 A | 8/1990 |
| JP | H03-037992 A | 2/1991 |
| JP | H03-152184 A | 6/1991 |
| JP | 2004-143419 A | 5/2004 |
| JP | 2004-527628 A | 9/2004 |
| JP | 2007-501884 A | 2/2007 |
| JP | 2007-534814 A | 11/2007 |
| JP | 2010-501030 A | 1/2010 |
| TW | I295280 B | 4/2008 |
| TW | 200825037 A | 6/2008 |
| TW | I312771 B | 8/2009 |
| TW | 394770 B1 * | 5/2013 |
| TW | I394770 B1 * | 5/2013 |
| WO | 00027946 A1 | 5/2000 |
| WO | 2009131255 A1 | 10/2009 |

OTHER PUBLICATIONS

Machine translaiton of CN101654399. Date of publication: Feb. 24, 2010.*

Search Report dated May 20, 2015 in TW 100147654.

Office Action dated Feb. 25, 2015 in CN Application No. 201180061375.3.

Yamamoto, "Electrically conducting and thermally stable pi-conjugated poly(arylene)s prepared by organometallic processes," Prog. Polym. Sci., vol. 17, pp. 1153-1205 (1992).

Miyaura et al, "Palladium-Catalyzed Cross-Coupling Reactions of Organoboron Compounds," Chem. Rev., vol. 95, pp. 2457-2483 (1995).

Yamamoto et al, "A Novel Type of Polycondensation Utilizing Transition Metal-Catalyzed C-C Coupling. I. Preparation of Thermostable Polyphenylene Type Polymers," Bulletin of the Chemical Society of Japan, vol. 51, No. 7, pp. 2091-2097 (Jul. 1978).

Li et al, "Synthesis and properties of novel poly(p-phenylenevinylene) copolymers for near-infrared emitting diodes," European Polymer Journal, vol. 41, pp. 2923-33 (2005).

Ayats et al, "Alternative Syntheses of the New D2d Symmetric Tetramethyl Tricyclo-[3.3.0.03,7]octane-1,3,5,7-tetracarboxylate," The Journal of Organic Chemistry, vol. 68, No. 22, pp. 8715-8718 (Oct. 31, 2003).

Van Ornum et al, "Steric and electronic effects on the Weiss reaction. Isolation of 1:1 adducts," Journal of the Chemical Society, Perkin Transactions 1, No. 22, pp. 3471-3478 (1997).

Int'l Search Report dated Mar. 27, 2012 in Int'l Application No. PCT/JP2011/079592.

Int'l Preliminary Report on Patentability dated Jul. 4, 2013 in Int'l Application No. PCT/JP2011/079592.

* cited by examiner

POLYMER COMPOUND AND LIGHT-EMITTING DEVICE USING SAME

CROSS-REFERENCE TO RELATED APPLICATION

This application is a Section 371 of International Application No. PCT/JP2011/079592, filed Dec. 21, 2011, which was published in the Japanese language on Jun. 28, 2012, under International Publication No. WO 2012/086668 A1, and the disclosure of which is incorporated herein by reference.

TECHNICAL FIELD

The present invention relates to a polymer compound, its raw material compound, composition containing the polymer compound, a liquid composition containing the polymer compound, an organic film, a light-emitting device, and a display device.

BACKGROUND ART

As a light-emitting material used for the light-emitting device, a polymer compound including a constitutional unit derived from arylamine (Patent Literature 1) and a polymer compound including a constitutional unit derived from fluorene (Patent Literature 2) have been examined, for example.

CITATION LIST

Patent Literature

Patent Literature 1: Japanese Patent Application Laid-Open No. 2004-143419

Patent Literature 2: National Publication of International Patent Application No. 2004-527628

SUMMARY OF INVENTION

Technical Problem

However, in the light-emitting device using the conventional polymer compound, its luminance life is not always sufficient.

Then, the present invention is aimed to provide a polymer compound useful for production of a light-emitting device whose luminance life is excellent. The present invention is moreover aimed to provide a composition containing the polymer compound, a liquid composition, an organic film, a light-emitting element, a surface lighting source, and a display device. The present invention is further aimed to provide a raw material compound for the polymer compound.

Solution to Problem

The present invention provides a polymer compound having a constitutional unit represented by the following formula (1).

[Chemical Formula 1]

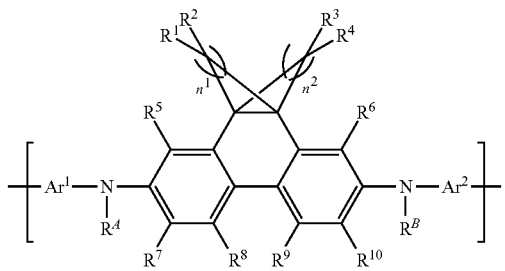

(1)

wherein $n^1$ and $n^2$ each independently represent an integer of 1 to 5; $R^1$, $R^2$, $R^3$, $R^4$, $R^5$, $R^6$, $R^8$, $R^9$ and $R^{10}$ each independently represent a hydrogen atom, an unsubstituted or substituted alkyl group, an unsubstituted or substituted alkoxy group, an unsubstituted or substituted aryl group, an unsubstituted or substituted aryloxy group, or an unsubstituted or substituted monovalent heterocyclic group; $R^A$ and $R^B$ each independently represent a hydrogen atom, an unsubstituted or substituted alkyl group, an unsubstituted or substituted aryl group, or an unsubstituted or substituted monovalent heterocyclic group; $Ar^1$ and $Ar^2$ each independently represent an unsubstituted or substituted arylene group, an unsubstituted or substituted divalent heterocyclic group, or a divalent group in which two or more same or different groups selected from arylene groups and divalent heterocyclic groups are linked (the group may have a substituent); when $R^1$, $R^2$, $R^3$, and $R^4$ exist in plural, the plurality of $R^1$, $R^2$, $R^3$, or $R^4$ may be the same or different from each other; among $R^1$, $R^2$, $R^3$, and $R^4$, adjacent groups may be linked to each other to form a ring structure; among $R^7$, $R^8$, $R^9$ and $R^{10}$, adjacent groups may be linked to each other to form a ring structure; $Ar^1$ and $R^A$ may be linked to each other to form a ring structure; and $Ar^2$ and $R^B$ may be linked to each other to form a ring structure.

According to the polymer compound, a light-emitting element whose luminance life is excellent is obtained.

The polymer compound according to the present invention may further have a constitutional unit represented by the following formula (2).

[Chemical Formula 2]

$$-\!\!\!+\!\!Ar^3\!\!+\!\!\!-$$

(2)

wherein $Ar^3$ represents an unsubstituted or substituted arylene group, an unsubstituted or substituted divalent heterocyclic group, or a divalent group in which two or more same or different groups selected from arylene groups and divalent heterocyclic groups are linked (the divalent group may have a substituent).

The polymer compound according to the present invention may have a constitutional unit consisting of an unsubstituted or substituted fluorenediyl group as the constitutional unit represented by the above formula (2).

The polymer compound according to the present invention may have a constitutional unit consisting of an unsubstituted or substituted 2,7-fluorenediyl group as the constitutional unit represented by the above formula (2).

The polymer compound according to the present invention may have a constitutional unit consisting of at least one group selected from the group consisting of an unsubstituted or substituted phenylene group, an unsubstituted or substituted naphthalenediyl group, an unsubstituted or substituted anthracenediyl group, and a group represented by the following formula (3') as the constitutional unit represented by the above formula (2).

[Chemical Formula 3]

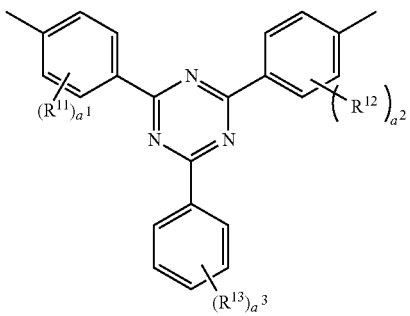

(3')

wherein $a^1$ and $a^2$ each independently represent an integer of 0 to 4; $a^3$ represents an integer of 0 to 5; $R^{11}$, $R^{12}$, and $R^{13}$ each independently represent an unsubstituted or substituted alkyl group, an unsubstituted or substituted alkoxy group, an unsubstituted or substituted aryl group, an unsubstituted or substituted aryloxy group, an unsubstituted or substituted monovalent heterocyclic group, an unsubstituted or substituted alkoxycarbonyl group, an unsubstituted or substituted silyl group, a halogen atom, a carboxyl group, or a cyano group; and when $R^{11}$, $R^{12}$, $R^{13}$, and $R^{14}$ exist in plural, the plurality of $R^{11}$, $R^{12}$, $R^{13}$, or $R^{14}$ may be the same or different from each other.

The polymer compound according to the present invention may further have a constitutional unit represented by the following formula (4):

[Chemical Formula 4]

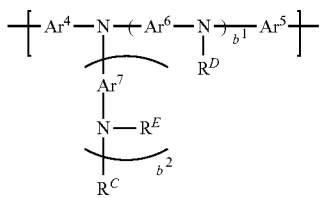

(4)

wherein $b^1$ and $b^2$ each independently represent 0 or 1; $Ar^4$, $Ar^5$, $Ar^6$, and $Ar^7$ each independently represent an unsubstituted or substituted arylene group, an unsubstituted or substituted divalent heterocyclic group, or a divalent group in which two or more same or different groups selected from arylene groups and divalent heterocyclic groups are linked (the group may have a substituent); $R^C$, $R^D$, and $R^E$ each independently represent a hydrogen atom, an unsubstituted or substituted alkyl group, an unsubstituted or substituted aryl group, or an unsubstituted or substituted monovalent heterocyclic group; $Ar^4$, $Ar^5$, $Ar^6$, and $Ar^7$ each may be linked to a group other than the group to form a ring structure, the other group being bonded to a nitrogen atom to which the group is bonded; and the constitutional unit represented by the formula (4) is different from the constitutional unit represented by the formula (1).

As the constitutional unit represented by the above formula (4), the polymer compound according to the present invention may have a constitutional unit represented by the following formula (5):

[Chemical Formula 5]

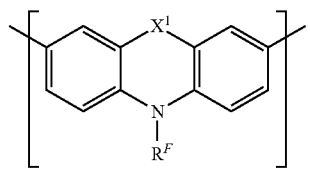

(5)

wherein $R^F$ represents a hydrogen atom, an unsubstituted or substituted alkyl group, an unsubstituted or substituted aryl group, or an unsubstituted or substituted monovalent heterocyclic group; $X^1$ represents a single bond, an oxygen atom, a sulfur atom, or a group represented by —C($R^{14}$)$_2$— ($R^{14}$ represents an unsubstituted or substituted alkyl group or an unsubstituted or substituted aryl group; and a plurality of $R^{14}$ may be the same or different from each other).

The polymer compound according to the present invention may have the constitutional unit represented by the above formula (1), the constitutional unit represented by the above formula (4), a constitutional unit consisting of an unsubstituted or substituted fluorenediyl group, and a constitutional unit consisting of an unsubstituted or substituted phenylene group.

The polymer compound according to the present invention may have the constitutional unit represented by the above formula (1), the constitutional unit represented by the above formula (4), a constitutional unit consisting of an unsubstituted or substituted fluorenediyl group, and a constitutional unit consisting of an unsubstituted or substituted naphthalenediyl group.

The polymer compound according to the present invention may have the constitutional unit represented by the above formula (1), the constitutional unit represented by the above formula (4), a constitutional unit consisting of an unsubstituted or substituted fluorenediyl group, and a constitutional unit consisting of an unsubstituted or substituted anthracenediyl group.

The polymer compound according to the present invention may have the constitutional unit represented by the above formula (1), the constitutional unit represented by the above formula (4), a constitutional unit consisting of an unsubstituted or substituted fluorenediyl group, and the constitutional unit represented by the following formula (3) (namely, the constitutional unit including the group represented by the formula (3')).

[Chemical Formula 6]

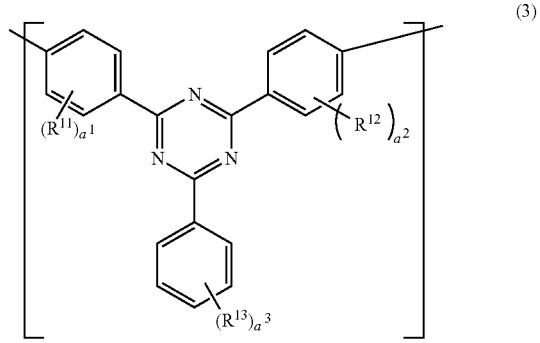

(3)

wherein $a^1$ and $a^2$ each independently represent an integer of 0 to 4; $a^3$ represents an integer of 0 to 5; $R^{11}$, $R^{12}$, and $R^{13}$ each independently represent an unsubstituted or substituted alkyl group, an unsubstituted or substituted alkoxy group, an unsubstituted or substituted aryl group, an unsubstituted or substituted aryloxy group, an unsubstituted or substituted monovalent heterocyclic group, an unsubstituted or substituted alkoxycarbonyl group, an unsubstituted or substituted silyl group, a halogen atom, a carboxyl group, or a cyano group; and when $R^{11}$, $R^{12}$, $R^{13}$, and $R^{14}$ exist in plural, the plurality of $R^{11}$, $R^{12}$, $R^{13}$, or $R^{14}$ may be the same or different from each other.

In the polymer compound according to the present invention, $n^1$ and $n^2$ in the above formula (1) each independently may be 3 or 4.

In the polymer compound according to the present invention, $R^A$ and $R^B$ in the above formula (1) each independently represent an unsubstituted or substituted aryl group or an unsubstituted or substituted monovalent heterocyclic group.

The polymer compound according to the present invention may be synthesized by condensation polymerization of a monomer (1) that introduces the constitutional unit represented by the above formula (1) with a monomer (X) that introduces a constitutional unit different from the constitutional unit, wherein when the number of the monomer (1) is $N_1$ and the number of the monomer (X) is $N_X$, $N_1$ and $N_X$ satisfy the following formula (1). According to the polymer compound, a light-emitting element more excellent in luminance life is obtained. According to the polymer compound, a light-emitting device more excellent in luminance life is obtained.

$$0.1 \leq N_1 \times 100/(N_1+N_X) \leq 50 \qquad (I)$$

Moreover, the present invention provides a compound represented by the following formula (1M):

[Chemical Formula 7]

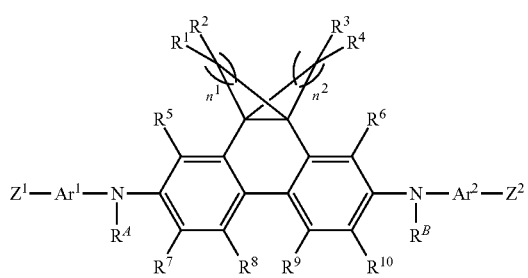

(1M)

wherein $n^1$ and $n^2$ each independently represent an integer of 1 to 5; $R^1$, $R^2$, $R^3$, $R^4$, $R^5$, $R^6$, $R^7$, $R^8$, $R^9$ and $R^{10}$ each independently represent a hydrogen atom, an unsubstituted or substituted alkyl group, an unsubstituted or substituted alkoxy group, an unsubstituted or substituted aryl group, an unsubstituted or substituted aryloxy group, or an unsubstituted or substituted monovalent heterocyclic group; $R^A$ and $R^B$ each independently represent a hydrogen atom, an unsubstituted or substituted alkyl group, an unsubstituted or substituted aryl group, or an unsubstituted or substituted monovalent heterocyclic group; $Ar^1$ and $Ar^2$ each independently represent an unsubstituted or substituted arylene group, an unsubstituted or substituted divalent heterocyclic group, or a divalent group in which two or more same or different groups selected from arylene groups and divalent heterocyclic groups are linked (the group may have a substituent); when $R^2$, $R^3$, and $R^4$ exist in plural, the plurality of $R^1$, $R^2$, $R^3$, or $R^4$ may be the same or different from each other; among $R^1$, $R^2$, $R^3$, and $R^4$, adjacent groups may be linked to each other to form a ring structure; among $R^7$, $R^8$, $R^9$ and $R^{10}$, adjacent groups may be linked to each other to form a ring structure; $Ar^1$ and $R^A$ may be linked to each other to form a ring structure; $Ar^2$ and $R^B$ may be linked to each other to form a ring structure; and $Z^1$ and $Z^2$ each independently represent a group selected from the following substituent group:

<Substituent Group> a chlorine atom, a bromine atom, iodine atom, a group represented by $-O-S(=O)_2R^{41}$ wherein $R^{41}$ represents an alkyl group, or an aryl group that may be substituted with an alkyl group, an alkoxy group, a nitro group, a fluorine atom, or a cyano group, a group represented by $-B(OR^{42})_2$ wherein $R^{42}$ represents a hydrogen atom or an alkyl group; and a plurality of $R^{42}$ present may be the same or different from each other and may be bonded to each other to form a cyclic structure, a group represented by $-BF_4Q^1$ wherein $Q^1$ represents a monovalent cation selected from the group consisting of $Li^+$, $Na^+$, $K^+$, $Rb^+$, and $Cs^+$, a group represented by $-MgY^1$ wherein $Y^1$ represents a chlorine atom, a bromine atom, or an iodine atom, a group represented by $-ZnY^2$ wherein $Y^2$ represents a chlorine atom, a bromine atom, or an iodine atom, and a group represented by $-Sn(R^{43})_3$ wherein $R^{43}$ represents a hydrogen atom or an alkyl group; and a plurality of $R^{43}$ present may be the same or different from each other and may be bonded to each other to form a cyclic structure.

Moreover, the present invention provides a composition containing the polymer compound according to the present invention and at least one selected from the group consisting of a hole transport material, an electron transport material, and a light-emitting material. The composition can be suitably used in production of the light-emitting device, and the light-emitting device to be obtained is excellent in luminance life.

The composition according to the present invention may contain a triplet light-emitting complex as the light-emitting material. The composition can be suitably used in production of the light-emitting device, and the light-emitting device to be obtained is excellent in luminance life.

Moreover, the present invention provides a liquid composition containing the polymer compound according to the present invention and a solvent. According to the liquid composition, an organic film containing the polymer compound can be easily produced.

Moreover, the present invention provides an organic film containing the polymer compound according to the present invention. The organic film is useful for production of the light-emitting device whose luminance life is excellent.

Moreover, the present invention provides an organic film using the composition according to the present invention. The organic film is useful for production of the light-emitting device whose luminance life is excellent.

Moreover, the present invention provides a light-emitting device having the organic film according to the present invention. The light-emitting device is excellent in luminance life.

Moreover, the present invention provides a surface lighting source and a display device having the light-emitting device according to the present invention.

Advantageous Effects of Invention

According to the present invention, a polymer compound useful for production of a light-emitting device whose luminance life is excellent can be provided. Moreover, according to the present invention, a composition, liquid composition, organic film, light-emitting device, surface lighting source, and display device containing the polymer compound can be provided. Further, according to the present invention, a raw material compound for the polymer compound can be provided.

DESCRIPTION OF EMBODIMENTS

Figure 1:
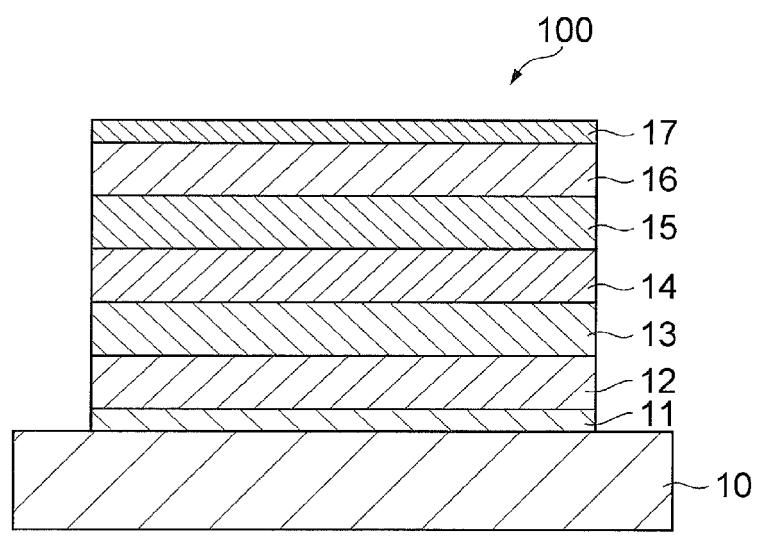
FIG. 1 is a schematic sectional view showing one embodiment of a light-emitting device according to the present invention.

Hereinafter, terms commonly used herein will be described, using examples when necessary.

Herein, "Me" represents a methyl group, "Et" represents an ethyl group, "Ph" represents a phenyl group, and "t-Bu" represents a tert-butyl group.

The "constitutional unit" means one or more unit structures that are present in the polymer compound. It is preferable that the "constitutional unit" be included in the polymer compound as a "repeating unit" (namely, two or more unit structures that are present in the polymer compound).

The term "$C_x$ to $C_y$" (x and y are a positive integer that satisfies x<y) means that the number of carbon atoms in a partial structure corresponding to the name of the functional group written immediately after the term is x to y. Namely, in the case where the organic group written immediately after "$C_x$ to $C_y$" is an organic group named in combination of a plurality of names of functional groups (for example, a $C_x$ to $C_y$ alkoxyphenyl group), the term means that among the plurality of names of functional groups, the number of carbon atoms in the partial structure corresponding to the name of the functional group written immediately after "$C_x$ to $C_y$" (for example, alkoxy) is x to y. For example, the "$C_1$ to $C_{12}$ alkyl group" means an alkyl group having 1 to 12 carbon atoms, and the "$C_1$ to $C_{12}$ alkoxyphenyl group" means a phenyl group having an "alkoxy group having 1 to 12 carbon atoms."

Herein, the term "unsubstituted or substituted" means that the functional group written immediately after the term may have a substituent. For example, the "unsubstituted or substituted alkyl group" means an "unsubstituted alkyl group or an alkyl group having a substituent."

Examples of the substituent include an alkyl group, an alkoxy group, an alkylthio group, an aryl group, an acyloxy group, an arylthio group, an alkenyl group, an alkynyl group, an amino group, a silyl group, halogen atoms, an acyl group, an acyloxy group, an oxycarbonyl group, a monovalent heterocyclic group, a heterocycleoxy group, a heterocyclethio group, imine residues, amide compound residues, acid imide residues, a carboxyl group, a hydroxy group, a nitro group, and a cyano group. These groups may further have a substituent selected from the groups above.

The "alkyl group" may have a substituent, and may be any of a linear alkyl group, a branched alkyl group, and a cyclic alkyl group (cycloalkyl group). Unless otherwise specified, without including the number of carbon atoms of the substituent, the number of carbon atoms of the alkyl group is preferably 1 to 20, more preferably 1 to 15, and still more preferably 1 to 12 in the linear alkyl group and the branched alkyl group; without including the number of carbon atoms of the substituent, the number of carbon atoms of the alkyl group is preferably 3 to 20, more preferably 3 to 15, and still more preferably 3 to 12 in the cyclic alkyl group. Examples of the alkyl group include a methyl group, an ethyl group, a propyl group, an isopropyl group, a butyl group, an isobutyl group, a sec-butyl group, a tert-butyl group, a pentyl group, an isoamyl group, a hexyl group, a cyclohexyl group, a heptyl group, an octyl group, a 2-ethylhexyl group, a nonyl group, a decyl group, a 3,7-dimethyloctyl group, and a dodecyl group.

The "alkoxy group" may have a substituent, and may be any of a linear alkoxy group, a branched alkoxy group, and a cyclic alkoxy group (cycloalkoxy group). Unless otherwise specified, without including the number of carbon atoms of the substituent, the number of carbon atoms of the alkoxy group is preferably 1 to 20, more preferably 1 to 15, and still more preferably 1 to 12 in the linear alkoxy group and the branched alkoxy group; without including the number of carbon atoms of the substituent, the number of carbon atoms of the alkoxy group is preferably 3 to 20, more preferably 3 to 15, and still more preferably 3 to 12 in the cyclic alkoxy group. Examples of the alkoxy group include a methoxy group, ethoxy group, a propyloxy group, an isopropyloxy group, a butoxy group, an isobutoxy group, a sec-butoxy group, a tert-butoxy group, a pentyloxy group, a hexyloxy group, a cyclohexyloxy group, a heptyloxy group, an octyloxy group, a 2-ethylhexyloxy group, a nonyloxy group, a decyloxy group, a 3,7-dimethyloctyloxy group, and a dodecyloxy group.

The "alkylthio group" may have a substituent, and may be any of a linear alkylthio group, a chain alkylthio group, and a cyclic alkylthio group (cycloalkylthio group). Unless otherwise specified, without including the number of carbon atoms of the substituent, the number of carbon atoms of the alkoxy group is preferably 1 to 20, more preferably 1 to 15, and still more preferably 1 to 12 in the linear alkylthio group and the branched alkylthio group; without including the number of carbon atoms of the substituent, the number of carbon atoms of the alkoxy group is preferably 3 to 20, more preferably 3 to 15, and still more preferably 3 to 12 in the cyclic alkylthio group. Examples of the alkylthio group include a methylthio group, an ethylthio group, a propylthio group, an isopropylthio group, a butylthio group, an isobutylthio group, a sec-butylthio group, a tert-butylthio group, a pentylthio group, a hexylthio group, a cyclohexylthio group, a heptylthio group, an octylthio group, a 2-ethylhexylthio group, a nonylthio group, a decylthio group, a 3,7-dimethyloctylthio group, and a dodecylthio group.

The "aryl group" is the remaining atomic group in which one hydrogen atom bonded to carbon atoms that form an aromatic ring is removed from an aromatic hydrocarbon. The aryl group may have a substituent, and examples of the aryl group include those having a benzene ring, and those having a condensation ring. Unless otherwise specified, without including the number of carbon atoms of the substituent, the number of carbon atoms of the aryl group is preferably 6 to 60, more preferably 6 to 48, and still more preferably 6 to 30. Examples of the aromatic hydrocarbon include benzene, naphthalene, anthracene, phenanthrene, naphthacene, fluorene, pyrene, and perylene. Examples of the aryl group include a phenyl group, a 1-naphthyl group, a 2-naphthyl group, a 1-anthracenyl group, a 2-anthracenyl group, a 9-anthracenyl group, and 2-fluorenyl group.

The "aryloxy group" is the group represented by —O—$Ar^{11}$ ($Ar^{11}$ represents the aryl group), and the aryl group in $Ar^{11}$ may have a substituent. Unless otherwise specified, without including the number of carbon atoms of the substituent, the number of carbon atoms of the aryloxy group is preferably 6 to 60, more preferably 6 to 48, and still more preferably 6 to 30. Examples of the aryloxy group include a phenoxy group, a 1-naphthyloxy group, a 2-naphthyloxy group, a 1-anthracenyloxy group, a 2-anthracenyloxy group, a 9-anthracenyloxy group, and a 2-fluorenyloxy group.

The "arylthio group" is the group represented by —S—$Ar^{12}$ ($Ar^{12}$ represents the aryl group), and the aryl group in $Ar^{12}$ may have a substituent. Unless otherwise specified, without including the number of carbon atoms of the substituent, the number of carbon atoms of the arylthio group is preferably 6 to 60, more preferably 6 to 48, and still more preferably 6 to 30. Examples of the arylthio group include a phenylthio group, a 1-naphthylthio group, a 2-naphthylthio group, a 1-anthracenylthio group, a 2-anthracenylthio group, a 9-anthracenylthio group, and a 2-fluorenylthio group.

The "alkenyl group" is the remaining atomic group in which one hydrogen atom bonded to $sp^2$ carbon atoms in alkene is removed. The alkenyl group may have a substituent, and may be any of a linear alkenyl group, a branched alkenyl group, and a cyclic alkenyl group. Unless otherwise specified, without including the number of carbon atoms of the substituent, the number of carbon atoms of the alkenyl group is preferably 2 to 20, more preferably 2 to 15, and still more preferably 2 to 10 in the linear alkenyl group and the branched alkenyl group; without including the number of carbon atoms of the substituent, the number of carbon atoms of the alkenyl group is preferably 3 to 20, more preferably 4 to 15, and still more preferably 5 to 10 in the cyclic alkenyl group. Examples of the alkenyl group include a vinyl group, a 1-propenyl group, a 2-propenyl group, a 1-butenyl group, a 2-butenyl group, a 1-pentenyl group, a 2-pentenyl group, a 1-hexenyl group, a 2-hexenyl group, and a 1-octenyl group.

The "alkynyl group" is the remaining atomic group in which one hydrogen atom bonded to $sp^1$ carbon atoms in alkyne is removed. The alkynyl group may have a substituent, and may be any of a linear alkynyl group, a branched alkynyl group, and a cyclic alkynyl group. Unless otherwise specified, without including the number of carbon atoms of the substituent, the number of carbon atoms of the alkynyl group is preferably 2 to 20, more preferably 2 to 15, and still more preferably 2 to 10 in the linear alkynyl group and the branched alkynyl group; without including the number of carbon atoms of the substituent, the number of carbon atoms of the alkynyl group is preferably 5 to 20, more preferably 6 to 15, and still more preferably 7 to 10 in the cyclic alkynyl group. Examples of the alkynyl group include an ethynyl group, a 1-propynyl group, a 2-propynyl group, a 1-butynyl group, a 2-butynyl group, a 1-pentynyl group, a 2-pentynyl group, a 1-hexynyl group, a 2-hexynyl group, and a 1-octynyl group.

The "amino group" may have a substituent, and is preferably an unsubstituted amino group and an amino group in which one or two hydrogens atom that the alkyl group has is substituted with one or two substituents selected from an alkyl group, an aryl group, an arylalkyl group, and a monovalent heterocyclic group (hereinafter, referred to as a "substituted amino group"). The substituent may further have a substituent (hereinafter, a substituent that a substituent having an organic group further has is referred to as a "secondary substituent" in some cases). Without including the number of carbon atoms of the secondary substituent, the number of carbon atoms of the substituted amino group is preferably 1 to 60, more preferably 2 to 48, and still more preferably 2 to 40.

Examples of the substituted amino group include a methylamino group, a dimethylamino group, an ethylamino group, a diethylamino group, a propylamino group, a dipropylamino group, an isopropylamino group, a diisopropylamino group, a butylamino group, an isobutylamino group, a sec-butylamino group, a tert-butylamino group, a pentylamino group, a hexylamino group, a heptylamino group, an octylamino group, a 2-ethylhexylamino group, a nonylamino group, a decylamino group, a 3,7-dimethyloctylamino group, a dodecylamino group, a cyclopentylamino group, a dicyclopentylamino group, a cyclohexylamino group, a dicyclohexylamino group, a ditrifluoromethylamino group, a phenylamino group, a diphenylamino group, a $C_1$ to $C_{12}$ alkoxyphenylamino group, a bis($C_1$ to $C_{12}$ alkoxyphenyl)amino group, a $C_1$ to $C_{12}$ alkylphenylamino group, a bis($C_1$ to $C_{12}$ alkylphenyl)amino group, a 1-naphthylamino group, a 2-naphthylamino group, a pentafluorophenylamino group, a pyridylamino group, a pyridazinylamino group, a pyrimidinylamino group, a pyrazinylamino group, a triazinylamino group, a phenyl-$C_1$ to $C_{12}$ alkylamino group, a $C_1$ to $C_{12}$ alkoxyphenyl-$C_1$ to $C_{12}$ alkylamino group, a di($C_1$ to $C_{12}$ alkoxyphenyl-$C_1$ to $C_{12}$ alkyl)amino group, a $C_1$ to $C_{12}$ alkylphenyl-$C_1$ to $C_{12}$ alkylamino group, a di($C_1$ to $C_{12}$ alkylphenyl-$C_1$ to $C_{12}$ alkyl) amino group, a 1-naphthyl-$C_1$ to $C_{12}$ alkylamino group, and a 2-naphthyl-$C_1$ to $C_{12}$ alkylamino group.

The "silyl group" may have a substituent, and is preferably an unsubstituted silyl group and a silyl group in which one to three hydrogen atoms that the silyl group has is substituted with one to three substituents selected from an alkyl group, an aryl group, an arylalkyl group, and a monovalent heterocyclic group (hereinafter, referred to as a "substituted silyl group"). The substituent may have a secondary substituent. Without including the number of carbon atoms of the secondary substituent, the number of carbon atoms of the substituted silyl group is preferably 1 to 60, more preferably 3 to 48, and still more preferably 3 to 40.

Examples of the substituted silyl group include a trimethylsilyl group, a triethylsilyl group, a tripropylsilyl group, a tri-isopropylsilyl group, a dimethyl-isopropylsilyl group, a diethyl-isopropylsilyl group, a tert-butyldimethylsilyl group, a pentyldimethylsilyl group, a hexyldimethylsilyl group, a heptyldimethylsilyl group, an octyldimethylsilyl group, a 2-ethylhexyl-dimethylsilyl group, a nonyldimethylsilyl group, a decyldimethylsilyl group, a 3,7-dimethyloctyl-dimethylsilyl group, a dodecyldimethylsilyl group, a phenyl-$C_1$ to $C_{12}$ alkylsilyl group, a $C_1$ to $C_{12}$ alkoxyphenyl-$C_1$ to $C_{12}$ alkylsilyl group, a $C_1$ to $C_{12}$ alkylphenyl-$C_1$ to $C_{12}$ alkylsilyl group, a 1-naphthyl-$C_1$ to $C_{12}$ alkylsilyl group, a 2-naphthyl-$C_1$ to $C_{12}$ alkylsilyl group, a phenyl-$C_1$ to $C_{12}$ alkyldimethylsilyl group, a triphenylsilyl group, a tri-p-xylylsilyl group, a tribenzylsilyl group, a diphenylmethylsilyl group, a tert-butyldiphenylsilyl group, and a dimethylphenylsilyl group.

Examples of the "acyl group" include groups represented by —C(=O)—$R^{44}$ ($R^{44}$ represents the alkyl group, the aryl group, or a monovalent heterocyclic group described later). The alkyl group, the aryl group, and the monovalent heterocyclic group in $R^{44}$ may have a substituent. Unless otherwise specified, without including the number of carbon atoms of the substituent, the number of carbon atoms of the acyl group is preferably 2 to 20, more preferably 2 to 18, and still more preferably 2 to 16. Examples of the acyl group include an acetyl group, a propionyl group, a butyryl group, an isobutyryl group, a pivaloyl group, and a benzoyl group. Examples of the acyl group having a substituent include an acyl group having a halogen atom as a substituent (such as a trifluoroacetyl group and a pentafluorobenzoyl group).

Examples of the "acyloxy group" include groups represented by —O—C(=O)—$R^{45}$ ($R^{45}$ represents the alkyl group, the aryl group, or a monovalent heterocyclic group described later). The alkyl group, the aryl group, and the monovalent heterocyclic group in $R^{45}$ may have a substituent. Unless otherwise specified, without including the number of carbon atoms of the substituent, the number of carbon atoms of the acyloxy group is preferably 2 to 20, more preferably 2 to 18, and still more preferably 2 to 16. Examples of the acyloxy group include an acetoxy group, a propionyloxy group, a butyryloxy group, an isobutyryloxy group, a pivaloyloxy group, and a benzoyloxy group. Examples of the acyloxy group having a substituent include an acyloxy group having a halogen atom as a substituent (such as a trifluoroacetyloxy group and a pentafluorobenzoyloxy group).

Examples of the "oxycarbonyl group" include groups represented by —C(=O)—O—$R^{45a}$ ($R^{45a}$ represents the alkyl group, the aryl group, or a monovalent heterocyclic group described later). The alkyl group, the aryl group, and the monovalent heterocyclic group in $R^{45a}$ may have a substituent. Unless otherwise specified, without including the number of carbon atoms of the substituent, the number of carbon atoms of the oxycarbonyl group is preferably 2 to 20, more preferably 2 to 18, and still more preferably 2 to 16.

The "monovalent heterocyclic group" is the remaining atomic group in which one hydrogen atom is removed from a heterocyclic compound. The monovalent heterocyclic group may have a substituent, and examples of the monovalent heterocyclic group include a monocyclic group, and a group having a condensation ring. Unless otherwise specified, without including the number of carbon atoms of the substituent, the number of carbon atoms in the monovalent heterocyclic group is preferably 4 to 60, more preferably 4 to 30, and still more preferably 4 to 20.

The heterocyclic compound designates compounds among organic compounds having a cyclic structure and the compounds including not only a carbon atom but also a hetero atom such as an oxygen atom, a sulfur atom, a nitrogen atom, a phosphorus atom, a boron atom, a silicon atom, a selenium atom, a tellurium atom, and an arsenic atom as the device that forms the ring.

As the monovalent heterocyclic group, monovalent aromatic heterocyclic groups are preferable. The monovalent aromatic heterocyclic group is the remaining atomic group in which one hydrogen atom is removed from an aromatic heterocyclic compound. Examples of the aromatic heterocyclic compound include compounds in which a heterocyclic ring itself containing a hetero atom demonstrates aromaticity, such as oxadiazole, thiadiazole, thiazole, oxazole, thiophene, pyrrole, phosphole, furan, pyridine, pyrazine, pyrimidine, triazine, pyridazin, quinoline, isoquinoline, carbazole, dibenzophosphole, dibenzofuran, and dibenzothiophene; and compounds in which a heterocyclic ring itself containing a hetero atom does not demonstrate aromaticity, but an aromatic ring is fused to the heterocycle, such as phenoxazine, phenothiazine, dibenzoborole, dibenzosilole, and benzopyran.

The "heterocycleoxy group" is a group represented by —O—$Ar^{13}$ ($Ar^{13}$ represents the monovalent heterocyclic group), and the monovalent heterocyclic group in $Ar^{13}$ may have a substituent. Unless otherwise specified, without including the number of carbon atoms of the substituent, the number of carbon atoms of the heterocycleoxy group is preferably 4 to 60, more preferably 4 to 30, and still more preferably 4 to 20. Examples of the heterocycleoxy group include a pyridyloxy group, a pyridazinyloxy group, a pyrimidinyloxy group, a pyrazinyloxy group, and a triazinyloxy group.

The "heterocyclethio group" is a group represented by —S—$Ar^{14}$ ($Ar^{14}$ represents the monovalent heterocyclic group), and the monovalent heterocyclic group in $Ar^{14}$ may have a substituent. Unless otherwise specified, without including the number of carbon atoms of the substituent, the number of carbon atoms of the heterocyclethio group is preferably 4 to 60, more preferably 4 to 30, and still more preferably 4 to 20. Examples of the heterocyclethio group include a pyridylthio group, a pyridazinylthio group, a pyrimidinylthio group, a pyrazinylthio group, and a triazinylthio group.

The "imine residue" means a residue in which a hydrogen atom in the formula is removed from an imine compound having a structure represented by at least one of the formula: H—N=C($R^{46}$)$_2$, and the formula: H—C($R^{47}$)=N—$R^{48}$. In the formulas, $R^{46}$, $R^{47}$, and $R^{48}$ each independently represent the alkyl group, the aryl group, the alkenyl group, the alkynyl group, or the monovalent heterocyclic group. The alkyl group, the aryl group, the alkenyl group, the alkynyl group, and the monovalent heterocyclic group in $R^{46}$, $R^{47}$ and $R^{48}$ may have a substituent. A plurality of $R^{46}$ present may be the same or different from each other, or may be linked to each other to form a cyclic structure. Examples of the imine residue include groups represented by the following structure:

[Chemical Formula 8]

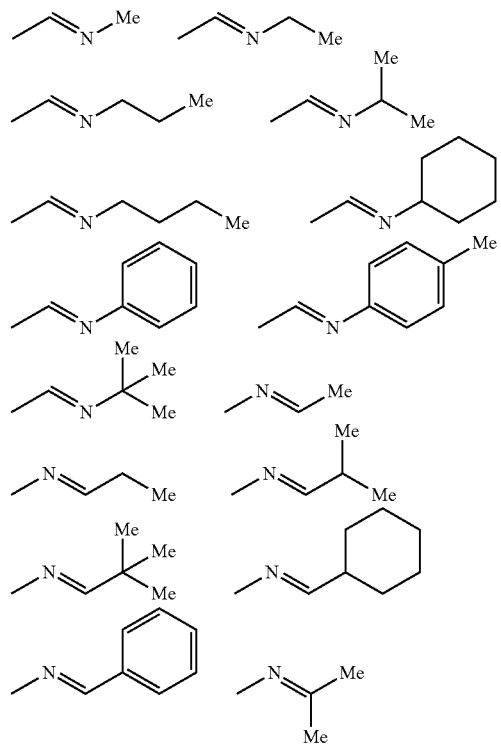

-continued

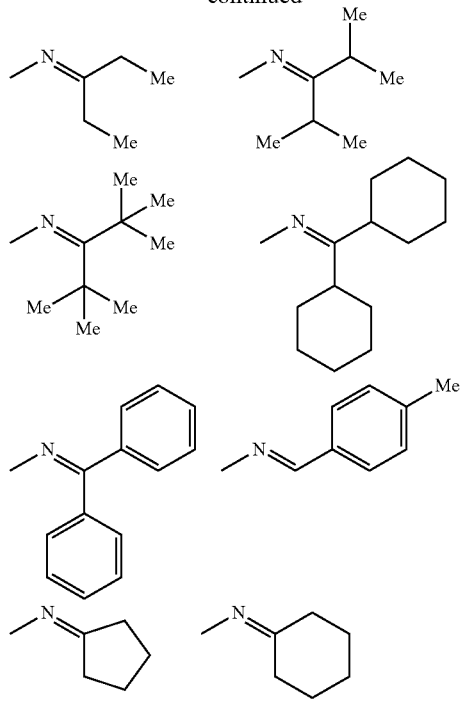

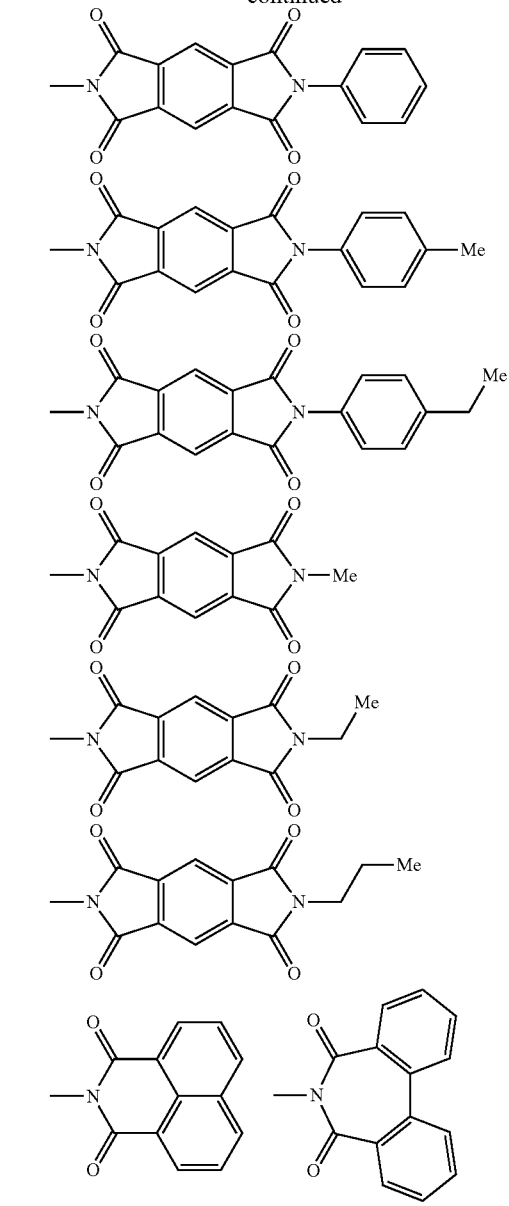

The "amide compound residue" means a residue in which a hydrogen atom in the formula is removed from an amide compound having a structure represented by at least one of the formula: H—N($R^{49}$)—C(=O)$R^{50}$ and the formula: H—C(=O)—N($R^{51}$)$_2$. In the formulas, $R^{49}$, $R^{50}$, and $R^{51}$ each independently represent the alkyl group, the aryl group, the alkenyl group, the alkynyl group, or the monovalent heterocyclic group. The alkyl group, the aryl group, the alkenyl group, the alkynyl group, and the monovalent heterocyclic group in $R^{49}$, $R^{50}$, and $R^{51}$ may have a substituent. A plurality of $R^{51}$ present may be the same or different from each other, and may be linked to each other to form a cyclic structure. Examples of the amide compound residue include formamide residues, acetoamide residues, propioamide residues, butyroamide residues, benzamide residues, trifluoroacetoamide residues, pentafluorobenzamide residues, diformamide residues, diacetoamide residues, dipropioamide residues, dibutyroamide residues, dibenzamide residues, ditrifluoroacetoamide residues, and dipentafluorobenzamide residues.

The "acid imide residue" means a residue obtained by removing one hydrogen atom bonded to a nitrogen atom from an acid imide. The number of carbon atoms of the acid imide residue is preferably 4 to 20, more preferably 4 to 18, and still more preferably 4 to 16. Examples of the acid imide residue include groups represented by the following structure:

[Chemical Formula 9]

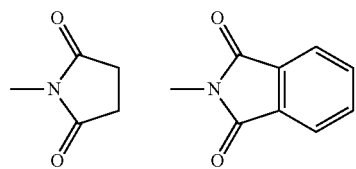

Examples of the "unsubstituted or substituted alkyl group" include unsubstituted alkyl groups and the alkyl groups having substituents above. Here, the substituent that the alkyl group has is preferably a substituent selected from an alkoxy group, an aryl group, an aryloxy group, a monovalent heterocyclic group, a heterocycleoxy group, and a halogen atom, unless otherwise specified.

Examples of the "unsubstituted or substituted alkoxy group" include unsubstituted alkoxy groups and the alkoxy groups having substituents above. Here, the substituent that the alkoxy group has is preferably a substituent selected from an alkoxy group, an aryl group, an aryloxy group, a monovalent heterocyclic group, a heterocycleoxy group, and a halogen atom, unless otherwise specified.

Examples of the "unsubstituted or substituted aryl group" include unsubstituted aryl groups and the aryl groups having the substituents. Here, the substituent that the aryl group has is preferably a substituent selected from an alkyl group, an alkoxy group, an aryl group, an aryloxy group, a monovalent heterocyclic group, a heterocycleoxy group, and a halogen atom unless otherwise specified.

Examples of the "unsubstituted or substituted aryloxy group" include unsubstituted aryloxy groups and aryloxy groups having the substituents above. Here, the substituent that the aryloxy group has is preferably a substituent selected from an alkyl group, an alkoxy group, an aryl group, an aryloxy group, a monovalent heterocyclic group, a heterocycleoxy group, and a halogen atom unless otherwise specified.

Examples of the "unsubstituted or substituted monovalent heterocyclic group" include unsubstituted monovalent heterocyclic groups and monovalent heterocyclic groups having the substituents above. Here, the substituent that the monovalent heterocyclic group has is preferably a substituent selected from an alkyl group, an alkoxy group, an aryl group, an aryloxy group, a monovalent heterocyclic group, a heterocycleoxy group, and a halogen atom unless otherwise specified.

Examples of the "unsubstituted or substituted arylene group" include unsubstituted arylene groups and arylene groups having the substituents above. Here, the substituent that the arylene group has is preferably a substituent selected from an alkyl group, an alkoxy group, an aryl group, an aryloxy group, a monovalent heterocyclic group, a heterocycleoxy group and a halogen atom unless otherwise specified.

The "arylene group" is the remaining atomic group in which two hydrogen atoms bonded to carbon atoms that form an aromatic ring are removed from an aromatic hydrocarbon. The arylene group may have a substituent, and groups having a benzene ring and groups having a condensation ring are included in the arylene group. Unless otherwise specified, without including the number of carbon atoms of the substituent, the number of carbon atoms of the arylene group is preferably 6 to 60, more preferably 6 to 48, and still more preferably 6 to 30.

Examples of the aromatic hydrocarbon include benzene, naphthalene, anthracene, phenanthrene, naphthacene, fluorene, pyrene, and perylene. Examples of the arylene group include phenylene groups such as a 1,4-phenylene group, a 1,3-phenylene group, and a 1,2-phenylene group; naphthalenediyl groups such as a 1,4-naphthalenediyl group, a 1,5-naphthalenediyl group, 2,6-naphthalenediyl group, and a 2,7-naphthalenediyl; anthracenediyl groups such as a 1,4-anthracenediyl group, a 1,5-anthracenediyl group, a 2,6-anthracenediyl group, and a 9,10-anthracenediyl group; phenanthrenediyl groups such as a 2,7-phenanthrenediyl group; naphthacenediyl groups such as a 1,7-naphthacenediyl group, a 2,8-naphthacenediyl group, and a 5,12-naphthacenediyl group; fluorenediyl groups such as a 2,7-fluorenediyl group and a 3,6-fluorenediyl group; pyrenediyl groups such as a 1,6-pyrenediyl group, a 1,8-pyrenediyl group, a 2,7-pyrenediyl group, and a 4,9-pyrenediyl group; and perylenediyl groups such as a 3,8-perylenediyl group, a 3,9-perylenediyl group, and a 3,10-perylenediyl group.

Examples of the "unsubstituted or substituted divalent heterocyclic group" include unsubstituted divalent heterocyclic groups and divalent heterocyclic groups having the substituents above. Here, the substituent that the divalent heterocyclic group has is preferably a substituent selected from an alkyl group, an alkoxy group, an aryl group, an aryloxy group, a monovalent heterocyclic group, a heterocycleoxy group, and a halogen atom unless otherwise specified.

The "divalent heterocyclic group" is the remaining atomic group in which two hydrogen atoms are removed from a heterocyclic compound. The divalent heterocyclic group may have a substituent, and monocyclic groups and groups having a condensation ring are included in the divalent heterocyclic group. Unless otherwise specified, without including the number of carbon atoms of the substituent, the number of carbon atoms of the divalent heterocyclic group is preferably 4 to 60, more preferably 4 to 30, and still more preferably 4 to 20.

As the divalent heterocyclic group, divalent aromatic heterocyclic groups are preferable. The divalent aromatic heterocyclic group is the remaining atomic group in which two hydrogen atoms are removed from an aromatic heterocyclic compound.

Examples of the divalent heterocyclic group include pyridinediyl groups such as a 2,5-pyridinediyl group and a 2,6-pyridinediyl group; quinolinediyl groups such as a 2,6-quinolinediyl group; isoquinolinediyl groups such as a 1,4-isoquinolinediyl group and a 1,5-isoquinolinediyl group; quinoxalinediyl groups such as a 5,8-quinoxalinediyl group; 2,1,3-benzothiadiazole groups such as a 2,1,3-benzothiadiazole-4,7-diyl group; benzothiazolediyl groups such as a 4,7-benzothiazolediyl group; dibenzosilolediyl groups such as a 2,7-dibenzosilolediyl group; dibenzofurandiyl groups such as a dibenzofuran-4,7-diyl group and a dibenzofuran-3,8-diyl group; and dibenzothiophenediyl groups such as a dibenzothiophene-4,7-diyl group and a dibenzothiophene-3,8-diyl group.

Examples of the "divalent group in which two or more same or different groups selected from arylene groups and divalent heterocyclic groups are linked" include divalent groups in which two groups selected from arylene groups and divalent heterocyclic groups are linked with a single bond such as a 2,7-biphenylylene group and a 3,6-biphenylylene group. The divalent group may have a substituent, and the substituent that the divalent group has is preferably a substituent selected from an alkyl group, an alkoxy group, an aryl group, an aryloxy group, a monovalent heterocyclic group, a heterocycleoxy group, and a halogen atom unless otherwise specified.

Hereinafter, suitable embodiments of the polymer compound, compound, composition, liquid composition, organic film, light-emitting device, surface lighting source, and display device according to the present invention will be described in detail.

(Polymer Compound)

The polymer compound according to the present embodiment has a first constitutional unit represented by the following formula (1). The polymer compound is useful in production of the light-emitting device whose luminance life is excellent because the polymer compound has this constitutional unit.

It is preferable that the polymer compound according to the present embodiment be a conjugated polymer compound. The polymer compound according to the present embodiment may further have a second constitutional unit represented by the following formula (2) and/or a third constitutional unit represented by the following formula (4). Such a polymer compound is more useful in production of the light-emitting device whose luminance life is excellent. Here, the "conjugated polymer compound" is a polymer compound in which a conjugated system expands on the main chain skeleton, and examples thereof include polyarylenes having an arylene group such as polyfluorene and polyphenylene as a constitutional unit; polyheteroarylene having a divalent heterocyclic group such as polythiophene and polydibenzofuran as a constitutional unit; polyarylenevinylene such as polyphenylenevinylene; and copolymers having these constitutional units in combination. The "conjugated polymer compound" may be a compound substantially conjugated even if a hetero atom or the like is included in the main chain in the constitutional unit; for example, the "conjugated polymer compound" may include a constitutional unit derived from triarylamine as the constitutional unit.

Hereinafter, the first constitutional unit, the second constitutional unit, and the third constitutional unit each will be described in detail.

(First Constitutional Unit)

The first constitutional unit is the constitutional unit represented by the following formula (1):

[Chemical Formula 10]

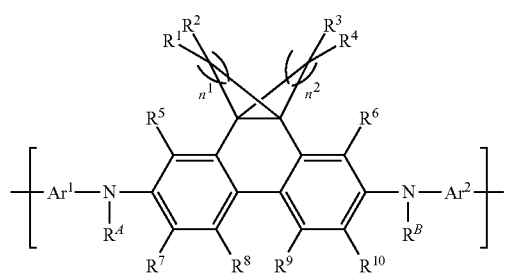

(1)

wherein $n^1$ and $n^2$ each independently represent an integer of 1 to 5; $R^1$, $R^2$, $R^3$, $R^4$, $R^5$, $R^6$, $R^7$, $R^8$, $R^9$ and $R^{10}$ each independently represent a hydrogen atom, an unsubstituted or substituted alkyl group, an unsubstituted or substituted alkoxy group, an unsubstituted or substituted aryl group, an unsubstituted or substituted aryloxy group, or an unsubstituted or substituted monovalent heterocyclic group; $R^A$ and $R^B$ each independently represent a hydrogen atom, an unsubstituted or substituted alkyl group, an unsubstituted or substituted aryl group, or an unsubstituted or substituted monovalent heterocyclic group; $Ar^1$ and $Ar^2$ each independently represent an "unsubstituted or substituted arylene group," an "unsubstituted or substituted divalent heterocyclic group," or a "divalent group in which two or more same or different groups selected from arylene groups and divalent heterocyclic groups are linked (the group may have a substituent)."

As $R^1$, $R^2$, $R^3$, and $R^4$, the hydrogen atom, the unsubstituted or substituted alkyl group, or the unsubstituted or substituted aryl group are preferable, or the hydrogen atom and the unsubstituted or substituted alkyl group are more preferable because synthesis of the monomer is easy, and the luminance life of the light-emitting device to be obtained is more excellent in the case where the polymer compound is used in production of the light-emitting device.

In the formula (1), when $n^1$ is an integer of 2 to 5, a plurality of $R^1$ present may be the same or different from each other, and a plurality of $R^2$ present may be the same or different from each other. When $n^2$ is an integer of 2 to 5, a plurality of $R^3$ present may be the same or different from each other, and a plurality of $R^4$ present may be the same or different from each other.

Among $R^1$, $R^2$, $R^3$, and $R^4$, adjacent groups may be linked to each other to form a cyclic structure. Among $R^7$, $R^8$, $R^9$, and $R^{10}$, adjacent groups may be linked to each other to form a cyclic structure.

$Ar^1$ and $R^A$ may be linked to each other to form a ring structure. $Ar^2$ and $R^B$ may be linked to each other to form a ring structure. Here, the expression "may be linked to each other to form a ring structure" indicates that $Ar^1$ and $R^A$ (or $Ar^2$ and $R^B$) may be bonded with a single bond or a group represented by —O—, —S—, —C(=O)—, —C(=O)—O—, —N($R^{15}$)—, —C(=O)—N($R^{15}$)—, or —C($R^{15}$)$_2$— ($R^{15}$ represents an unsubstituted or substituted alkyl group or an unsubstituted or substituted aryl group; when $R^{15}$ exists in plural, the plurality of $R^{15}$ may be the same or different from each other), to form a ring structure. Thereby, usually a 5- to 7-membered ring is formed.

It is preferable that the content of the first constitutional unit be 0.1 to 70 mol % of the total constitutional units, it is more preferable that the content of the first constitutional unit be 0.1 to 50 mol % of the total constitutional units, and it is still more preferable that the content of the first constitutional unit be 0.1 to 40 mol % of the total constitutional units because the luminance life of the light-emitting device to be obtained is more excellent in the case where the polymer compound is used in production of the light-emitting device.

In the first constitutional unit, for example, stereoisomerism can be produced when $n^1$ and/or $n^2$ is 2 or more and the first constitutional unit has a substituent, when $R^1$ and $R^2$ are different from each other, and when $R^3$ and $R^4$ are different from each other. As the first constitutional unit, the polymer compound may have only a constitutional unit having the same stereoisomerism, or may have a plurality of constitutional units having stereoisomerism different from each other. Examples of the stereoisomerism include diastereoisomers and enantiomers.

In the case where the dihydrophenanthrene skeleton portion of the first constitutional unit is represented by the formula (1-A), examples of the stereoisomerism are represented by the following formula (1-a), the formula (1-b), the formula (1-c), and the formula (1-d). In the following formulas, $R^a$ and $R^b$ each independently represent an alkyl group.

[Chemical Formula 11]

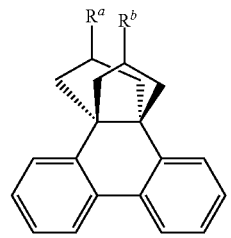

(1-A)

[Chemical Formula 12]

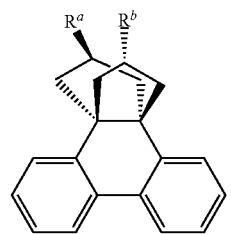

(1-a)

-continued

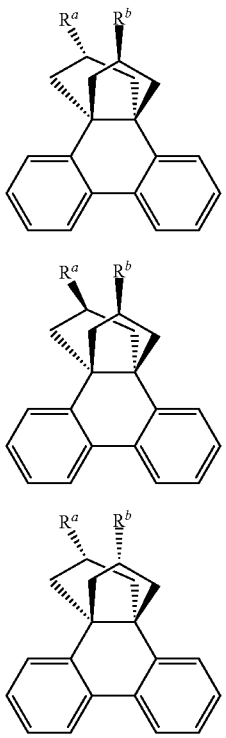

(1-b)

(1-c)

(1-d)

The constitutional unit represented by the formula (1-a), the constitutional unit represented by the formula (1-b), the constitutional unit represented by the formula (1-c) and the constitutional unit represented by the formula (1-d) are in the relationship of diastereoisomers.

In the formula (1), in the case where the group represented by $R^1$, $R^2$, $R^3$, $R^4$, $R^5$, $R^6$, $R^7$, $R^8$, $R^9$, and $R^{10}$ has a substituent, the substituent is preferably an alkyl group, an alkoxy group, an aryl group, an aryloxy group, an arylalkyl group, an arylalkoxy group, an arylalkenyl group, an arylalkynyl group, an amino group, a substituted amino group, a halogen atom, an acyl group, an acyloxy group, a monovalent heterocyclic group, a carboxyl group, a nitro group, and a cyano group, more preferably an alkyl group, an alkoxy group, an aryl group, an aryloxy group, an arylalkyl group, an arylalkoxy group, a substituted amino group, an acyl group, and a cyano group, and still more preferably an alkyl group, an alkoxy group, and an aryl group.

In the formula (1), $R^1$, $R^2$, $R^3$, and $R^4$ can be a hydrogen atom, an unsubstituted or substituted alkyl group, or an unsubstituted or substituted aryl group. Here, as the substituted alkyl group in $R^1$, $R^2$, $R^3$, and $R^4$, an arylalkyl group or an alkylarylalkyl group can be selected; as the substituted aryl group in $R^1$, $R^2$, $R^3$, and $R^4$, an alkylaryl group can be selected.

In the formula (1), $R^5$, $R^6$, $R^7$, $R^8$, $R^9$, and $R^{10}$ can be a hydrogen atom, an unsubstituted or substituted alkyl group, or an unsubstituted or substituted aryl group. Here, as the substituted alkyl group in $R^5$, $R^6$, $R^7$, $R^8$, $R^9$, and $R^{10}$, an arylalkyl group or an alkylarylalkyl group can be selected; as the substituted aryl group in $R^5$, $R^6$, $R^7$, $R^8$, $R^9$, and $R^{10}$, an alkylaryl group can be selected.

It is preferable that $R^A$ and $R^B$ be a substituted alkyl group, an unsubstituted or substituted aryl group, or an unsubstituted or substituted monovalent heterocyclic group; it is more preferable that $R^A$ and $R^B$ be an unsubstituted or substituted aryl group, or an unsubstituted or substituted monovalent heterocyclic group; and it is still more preferable that $R^A$ and $R^B$ be an unsubstituted or substituted aryl group because the stability of the polymer compound according to the present embodiment is good and the luminance life of the light-emitting device using the polymer compound is more excellent.

As $R^5$, $R^6$, $R^7$, and $R^{10}$, a hydrogen atom, an unsubstituted or substituted alkyl group, and an unsubstituted or substituted aryl group are preferable, and it is more preferable that at least two be a hydrogen atom because synthesis of the monomer is easy and the luminance life of the light-emitting device using the polymer compound is more excellent.

As $R^8$ and $R^9$, a hydrogen atom, an unsubstituted or substituted alkyl group, and an unsubstituted or substituted aryl group are preferable, and a hydrogen atom and an unsubstituted or substituted alkyl group are more preferable because the luminance life of the light-emitting device to be obtained is more excellent in the case where the polymer compound is used in production of the light-emitting device.

In the case where the group represented by $R^A$ and $R^B$ has a substituent in the formula (1), the substituent is preferably an alkyl group, an alkoxy group, an aryl group, an aryloxy group, an arylalkyl group, an arylalkoxy group, an arylalkenyl group, an arylalkynyl group, an amino group, a substituted amino group, a halogen atom, an acyl group, an acyloxy group, a monovalent heterocyclic group, a carboxyl group, a nitro group, and a cyano group, more preferably an alkyl group, an alkoxy group, an aryl group, an aryloxy group, an arylalkyl group, an arylalkoxy group, a substituted amino group, an acyl group, and a cyano group, and still more preferably an alkyl group, an alkoxy group, and an aryl group.

In the formula (1), the alkyl group in $R^A$ and $R^B$ is the same as the "alkyl group" described as the term commonly used; the alkyl group is preferably a $C_1$ to $C_{20}$ alkyl group. The alkyl group may have a substituent.

In the formula (1), the aryl group in $R^A$ and $R^B$ is the same "aryl group" described as the term commonly used; the aryl group is preferably a phenyl group, a 1-naphthyl group, a 2-naphthyl group, a 1-anthracenyl group, a 2-anthracenyl group, a 9-anthracenyl group, and a 2-fluorenyl. The aryl group may have a substituent.

In the formula (1), the monovalent heterocyclic group in $R^A$ and $R^B$ is the same "monovalent heterocyclic group" described as the term commonly used; the monovalent heterocyclic group is preferably a pyridyl group, a pyrimidyl group, a triazyl group, and a quinolyl group. The monovalent heterocyclic group may have a substituent.

In the case where the group represented by $Ar^1$ and $Ar^2$ has a substituent in the formula (1), examples of the substituent include an alkyl group, an alkoxy group, an aryl group, an aryloxy group, an arylalkyl group, an arylalkoxy group, an arylalkenyl group, an arylalkynyl group, an amino group, a substituted amino group, a halogen atom, an acyl group, an acyloxy group, a monovalent heterocyclic group, a carboxyl group, a nitro group, and a cyano group; the group is preferably an alkyl group, an alkoxy group, an aryl group, an aryloxy group, an arylalkyl group, an arylalkoxy group, a substituted amino group, an acyl group, and a cyano group, and more preferably an alkyl group, an alkoxy group, and an aryl group.

In the formula (1), as the group represented by $Ar^1$ and $Ar^2$, an unsubstituted or substituted arylene group and an unsubstituted or substituted divalent heterocyclic group are preferable.

In the formula (1), examples of the arylene group in $Ar^1$ and $Ar^2$ include a 1,2-phenylene group, a 1,3-phenylene group, a 1,4-phenylene group, a 1,4-naphthalenediyl group, a 2,6-naphthalenediyl group, a 2,7-naphthalenediyl group, a 2,6-anthracenediyl group, a 9,10-anthracenediyl group, a 2,7-phenanthrenediyl group, a 5,12-naphthacenediyl group, 2,7-fluorenediyl, a 3,6-fluorenediyl group, a 1,6-pyrenediyl group, a 2,7-pyrenediyl group, or a 3,8-perylenediyl group; the 1,4-phenylene group, 2,7-fluorenediyl, the 2,6-anthracenediyl group, the 9,10-anthracenediyl group, the 2,7-phenanthrenediyl group, and the 1,6-pyrenediyl group are more preferable, and these may have a substituent.

In the formula (1), examples of the divalent heterocyclic group in $Ar^1$ and $Ar^2$ include a 2,5-pyrrolediyl group, a dibenzofurandiyl group, a dibenzothiophenediyl group, a 2,1,3-benzothiadiazole-4,7-diyl group, a 3,7-phenoxazinediyl group, or a 3,6-carbazolediyl group; these may have a substituent.

In the formula (1), examples of the divalent group in which two or more same or different groups selected from arylene groups and divalent heterocyclic groups are linked in $Ar^1$ and $Ar^2$ include a group represented by the following formula (1a-1), (1a-2), (1a-3), (1a-4), (1a-5), (1a-6), or (1a-7); these may have a substituent.

[Chemical Formula 13]

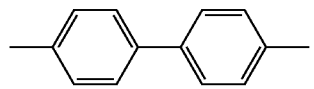
(1a-1)

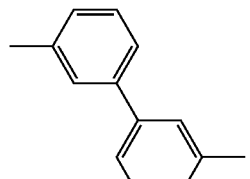
(1a-2)

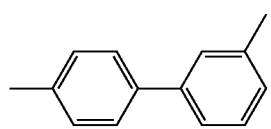
(1a-3)

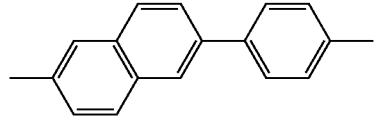
(1a-4)

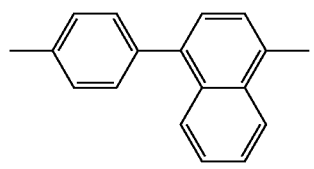
(1a-5)

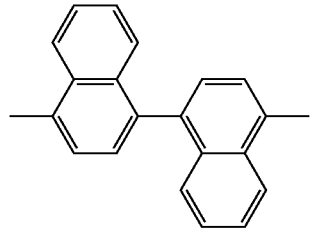
(1a-6)

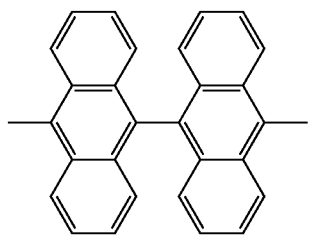
(1a-7)

In the formula (1), "among $R^1$, $R^2$, $R^3$, and $R^4$, adjacent groups may be linked to each other to form a cyclic structure" means that among $R^1$, $R^2$, $R^3$, and $R^4$, groups bonded to the same carbon atom may be linked to each other to form a cyclic structure, or when $n^1$ and/or $n^2$ is 2 or more, groups bonded to carbon atoms in adjacent positions may be linked to each other to form a cyclic structure.

In the formula (1), "among $R^7$, $R^8$, $R^9$, and $R^{10}$, adjacent groups may be linked to each other to form a cyclic structure" means that groups bonded to carbon atoms in adjacent positions may be linked to each other to form a cyclic structure, and for example, $R^8$ and $R^9$ may be linked to form a cyclic structure. Namely, the first constitutional unit can have a structure represented by, for example, the following formula (1b-1), (1b-2), (1b-3), (1b-4), (1b-5), or (1b-6):

[Chemical Formula 14]

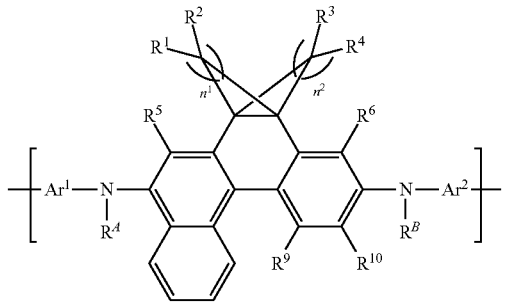
(1b-1)

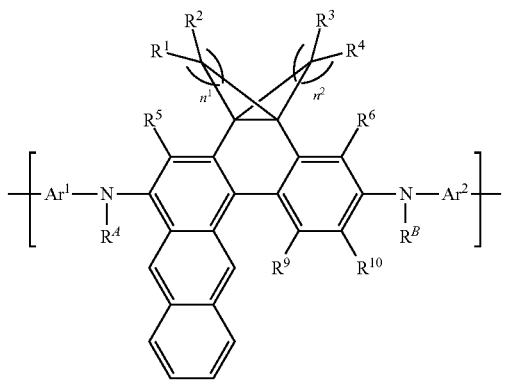
(1b-2)

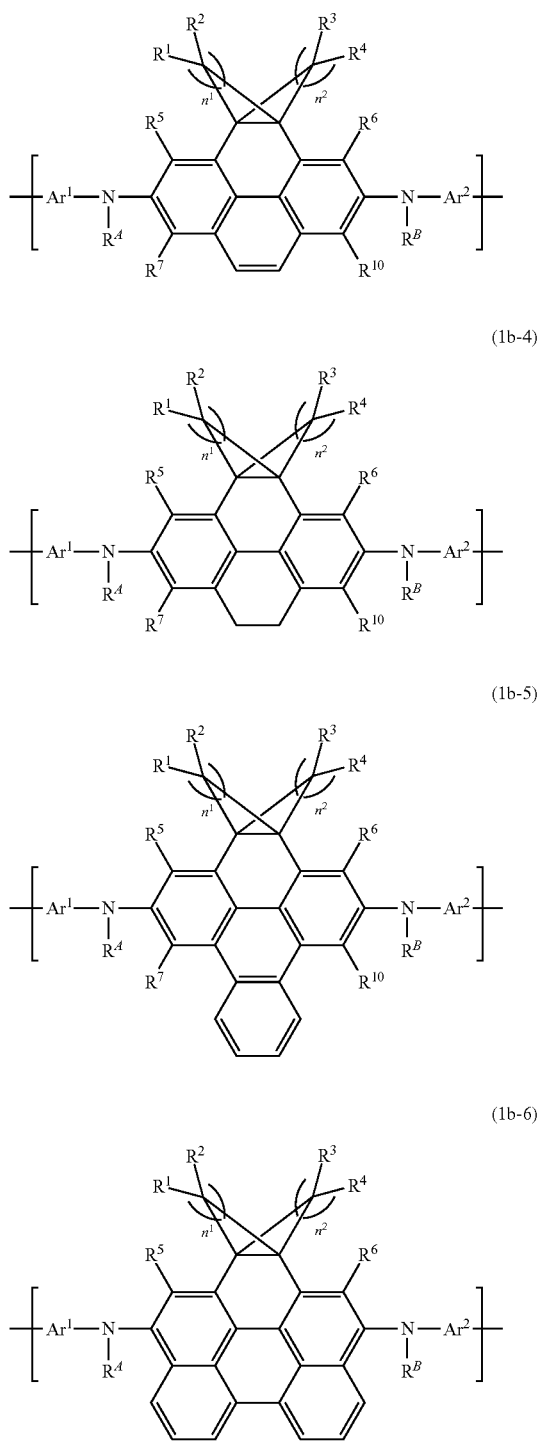

The structure represented by the formula (1b-1) and the structure represented by the formula (1b-2) are examples in which $R^7$ and $R^8$ in the formula (1) are linked to each other to form a cyclic structure. The structure represented by the formula (1b-3), the structure represented by the formula (1b-4), and the structure represented by the formula (1b-5) are examples in which $R^8$ and $R^9$ in the formula (1) are linked to each other to form a ring structure. The structure represented by the formula (1b-6) is an example in which $R^7$, $R^8$, $R^9$, and $R^{10}$ are linked to each other to form a ring structure.

The formed cyclic structure may have a substituent; the substituent is preferably an alkyl group, an alkoxy group, an aryl group, an aryloxy group, an arylalkyl group, an arylalkoxy group, an arylalkenyl group, an arylalkynyl group, an amino group, a substituted amino group, a halogen atom, an acyl group, an acyloxy group, a monovalent heterocyclic group, a carboxyl group, a nitro group, and a cyano group, more preferably an alkyl group, an alkoxy group, an aryl group, an aryloxy group, an arylalkyl group, an arylalkoxy group, a substituted amino group, and an acyl group, cyano group, and still more preferably an alkyl group, an alkoxy group, and an aryl group.

In the formula (1), because the luminance life of the light-emitting device using the polymer compound according to the present embodiment is more excellent, it is preferable that $n^1$ and $n^2$ be an integer of 3 to 5, it is more preferable that $n^1$ and $n^2$ be an integer of 3 or 4, and it is still more preferable that $n^1$ and $n^2$ be 3. $n^1$ and $n^2$ may be the same or different from each other; it is preferable that $n^1$ and $n^2$ be the same each other because production of the monomer is easy.

In the formula (1), the expression "$Ar^1$ and $R^A$ may be linked to each other to form a ring structure, and $Ar^2$ and $R^B$ may be linked to each other to form a ring structure" means that the first constitutional unit can have the structure represented by the following formula (1c-1), (1c-2), or (1c-3).

[Chemical Formula 15]

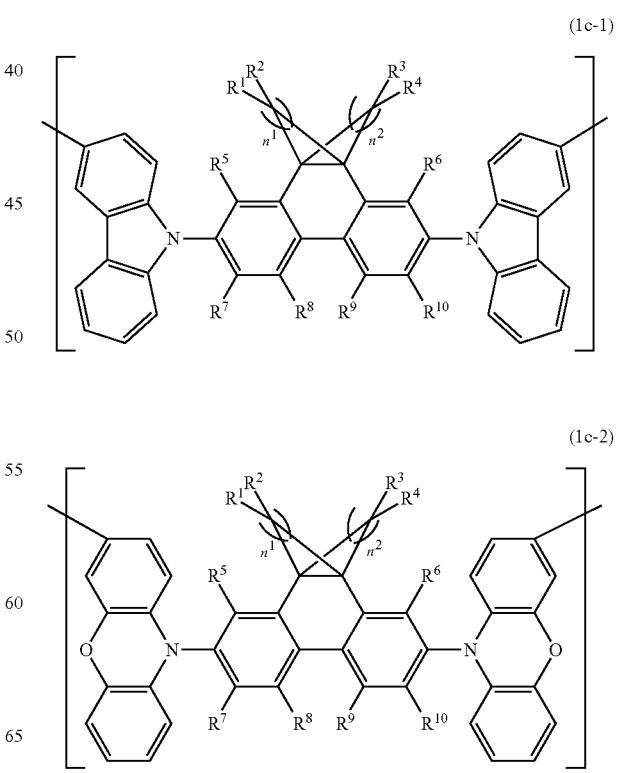

-continued (1c-3)

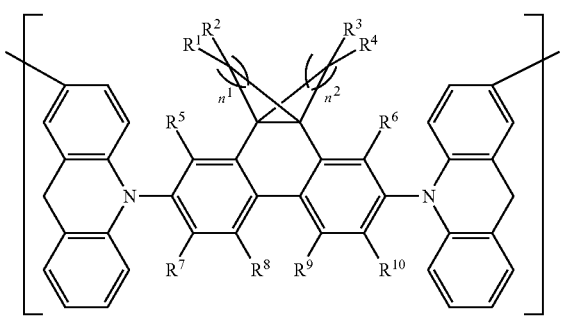

The formed ring structure may have a substituent; the substituent is preferably an alkyl group, an alkoxy group, an aryl group, an aryloxy group, an arylalkyl group, an arylalkoxy group, an arylalkenyl group, an arylalkynyl group, an amino group, a substituted amino group, a halogen atom, an acyl group, an acyloxy group, a monovalent heterocyclic group, a carboxyl group, a nitro group, and a cyano group, more preferably an alkyl group, an alkoxy group, an aryl group, an aryloxy group, an arylalkyl group, an arylalkoxy group, a substituted amino group, an acyl group, and a cyano group, and still more preferably an alkyl group, an alkoxy group, and an aryl group.

Examples of the first constitutional unit include constitutional units represented by the following formulas (1-1) to (1-21). Among the constitutional units represented by the formulas (1-1) to (1-21), the constitutional units represented by the formulas (1-1), (1-2), (1-3), (1-4), (1-6), (1-7), (1-8), (1-9), (1-11), (1-12), (1-13), (1-14), and (1-17) are preferable, the constitutional units represented by the formulas (1-1), (1-2), (1-3), (1-6), (1-7), (1-9), (1-11), and (1-14) are more preferable, and the constitutional units represented by the formulas (1-1), (1-2), (1-3), (1-6), (1-7), and (1-9) are still more preferable because the luminance life of the light-emitting device to be obtained is more excellent in the case where the polymer compound is used in production of the light-emitting device.

[Chemical Formula 16]

(1-1)

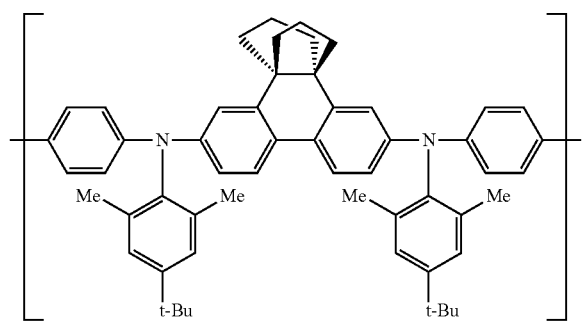

-continued (1-2)

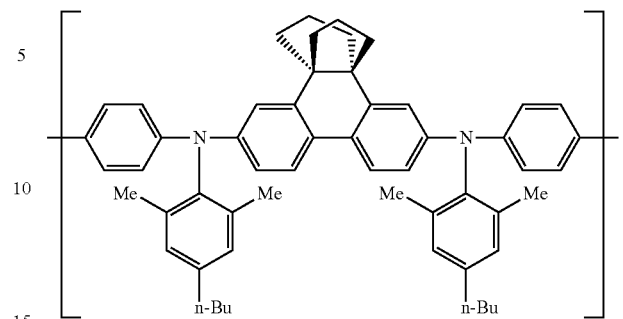

(1-3)

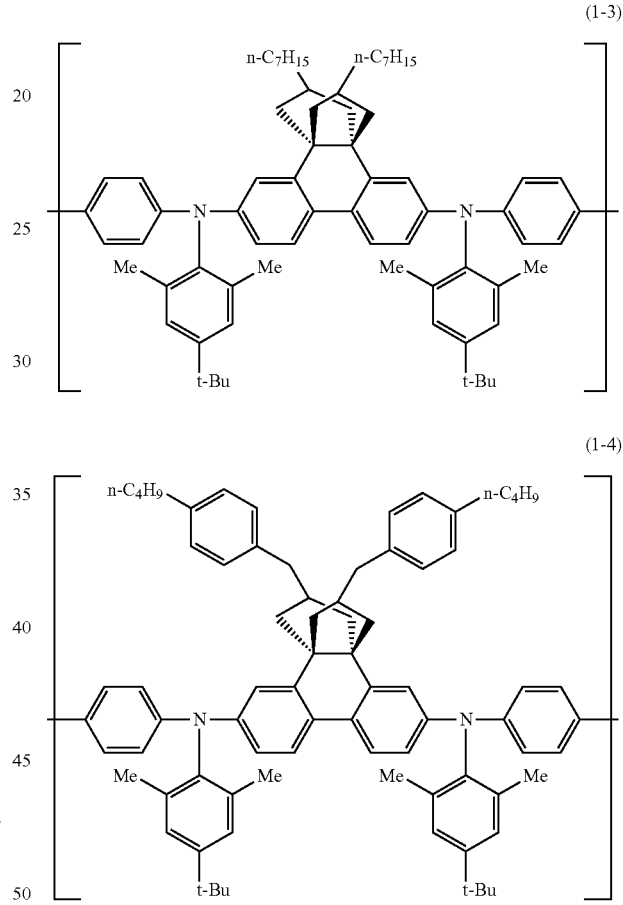

(1-4)

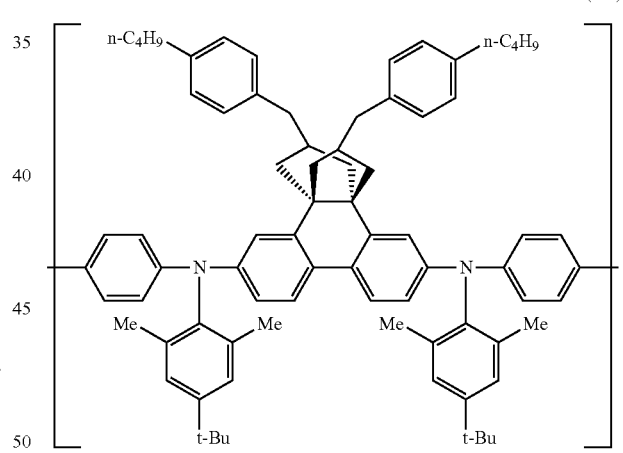

(1-5)

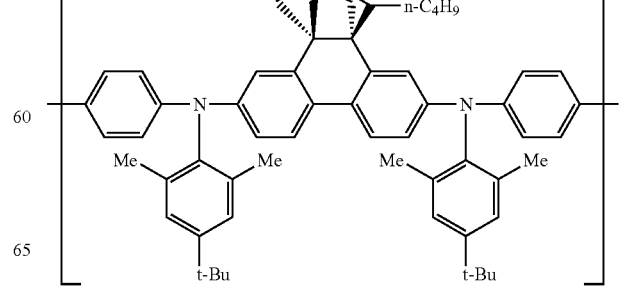

-continued
(1-6)
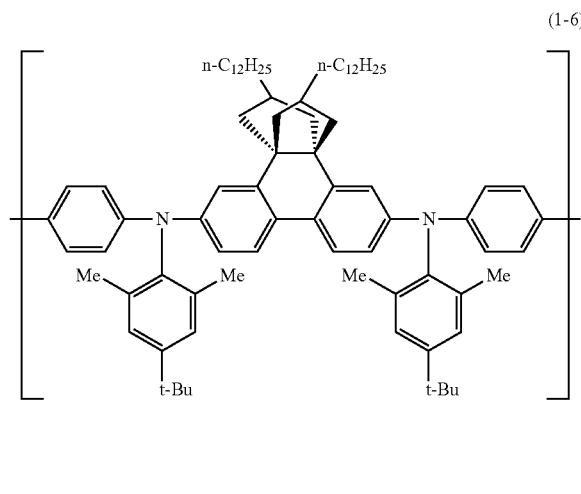
[Chemical Formula 17]
(1-7)
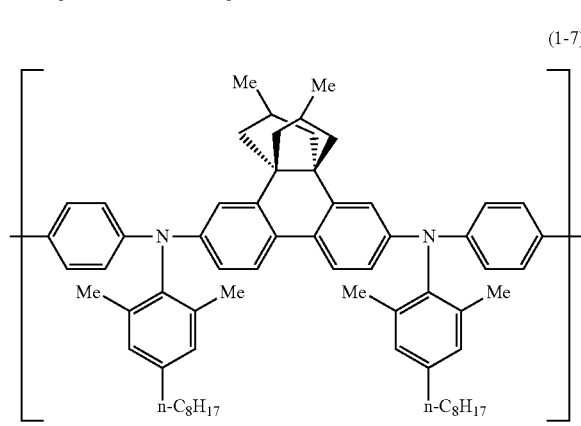
(1-8)
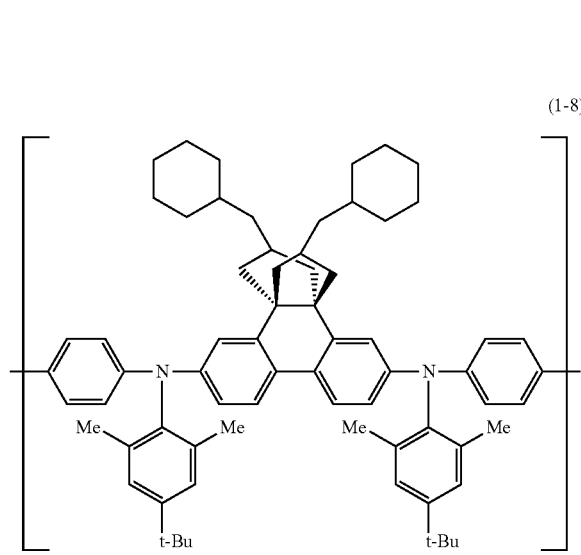
-continued
(1-9)
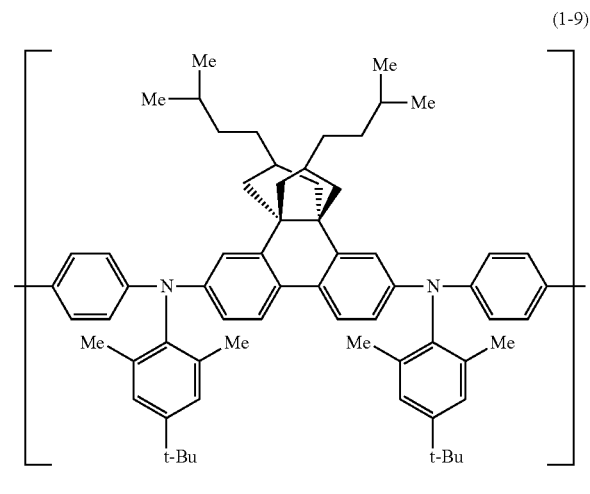
(1-10)
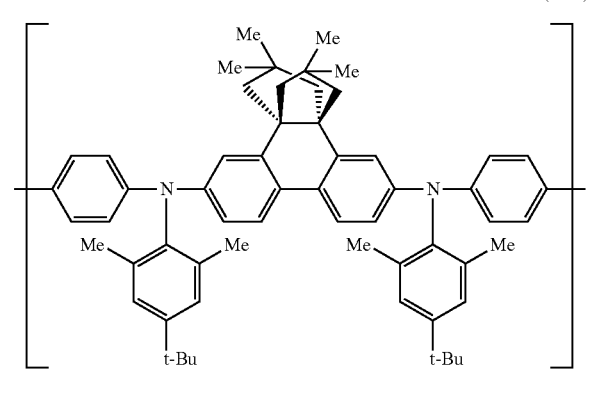
(1-11)
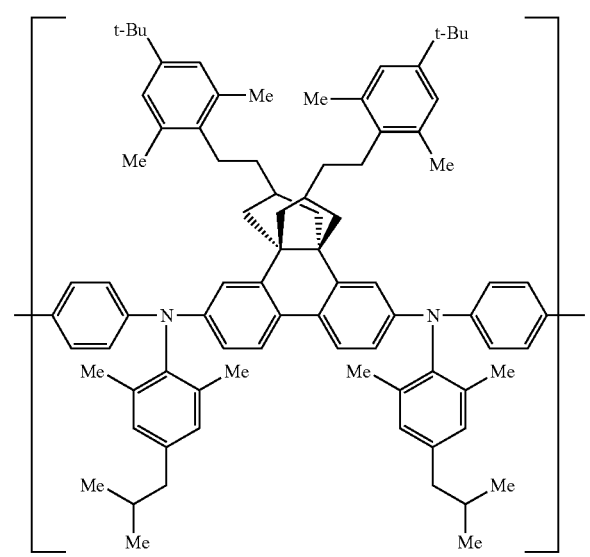

(1-12)
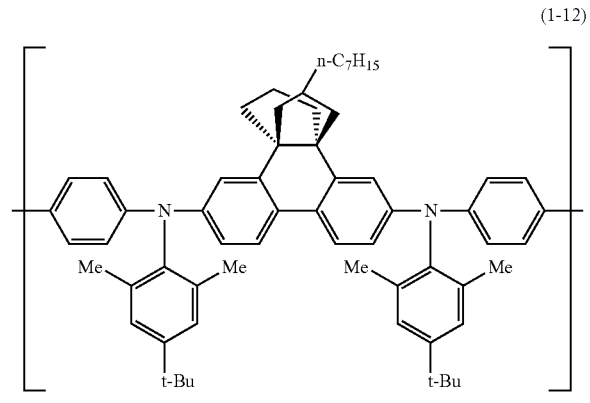
[Chemical Formula 18]
(1-13)
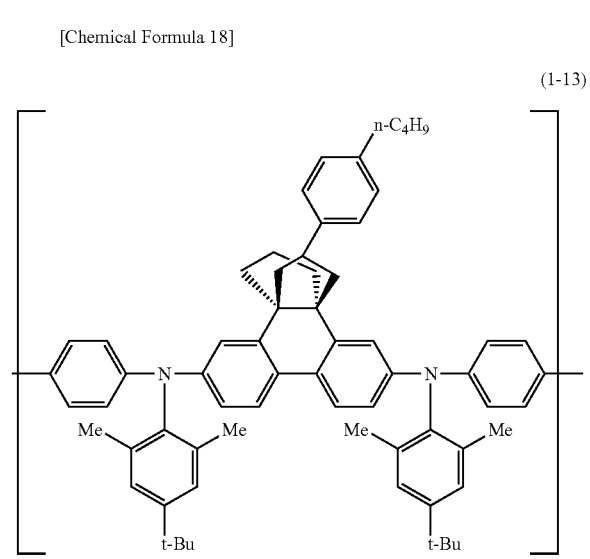
(1-14)
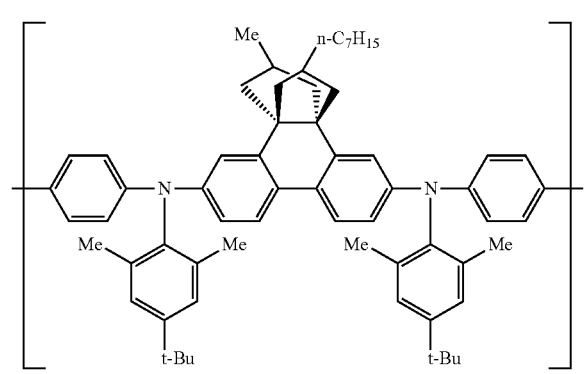
(1-15)
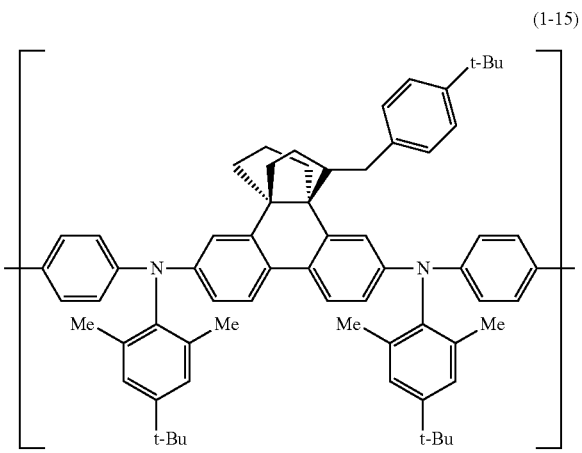
(1-16)
(1-17)
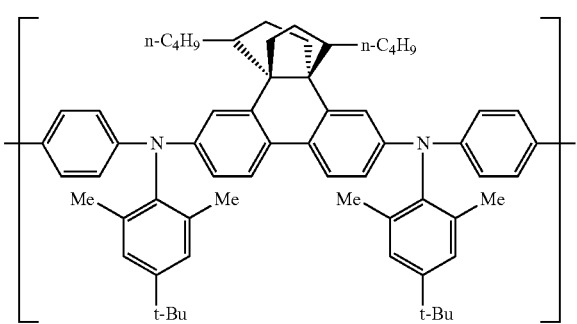
(1-18)

-continued

[Chemical Formula 19]

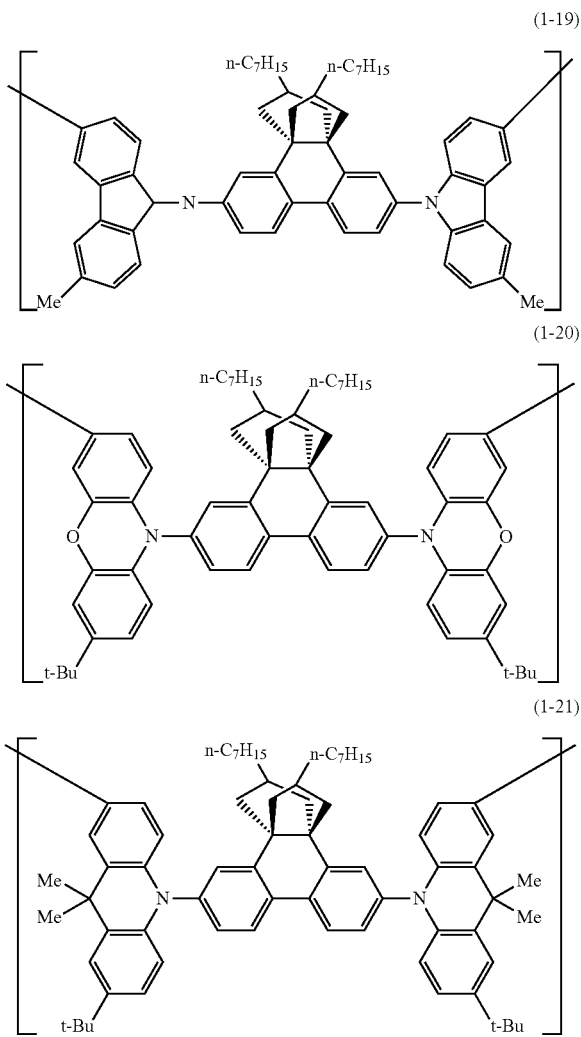

As the first constitutional unit, the polymer compound may have only one constitutional unit above, or may have a plurality of different constitutional units among the constitutional units above.

(Second Constitutional Unit)

The second constitutional unit is a constitutional unit represented by the following formula (2):

[Chemical Formula 20]

(2)

In the formula (2), Ar³ represents an unsubstituted or substituted arylene group, an unsubstituted or substituted divalent heterocyclic group, or a divalent group in which two or more same or different groups selected from arylene groups and divalent heterocyclic groups are linked (the group may have a substituent). The constitutional unit represented by the formula (2) is different from the group represented by the formula (5) described later.

In the case where the group represented by Ar³ in the formula (2) has a substituent, the substituent is preferably an alkyl group, an alkoxy group, an aryl group, an aryloxy group, an arylalkyl group, an arylalkoxy group, an arylalkenyl group, an arylalkynyl group, an amino group, a substituted amino group, a halogen atom, an acyl group, an acyloxy group, a monovalent heterocyclic group, a carboxyl group, a nitro group, and a cyano group, more preferably an alkyl group, an alkoxy group, an aryl group, an aryloxy group, an arylalkyl group, an arylalkoxy group, a substituted amino group, an acyl group, a cyano group, and still more preferably an alkyl group, an alkoxy group, and an aryl group.

In the formula (2), as the group represented by Ar³, an unsubstituted or substituted arylene group, and an unsubstituted or substituted divalent heterocyclic group are preferable.

In the formula (2), examples of the arylene group in Ar³ include a 1,2-phenylene group, a 1,3-phenylene group, a 1,4-phenylene group, a 1,4-naphthalenediyl group, a 2,6-naphthalenediyl group, a 2,7-naphthalenediyl group, a 2,6-anthracenediyl group, a 9,10-anthracenediyl group, a 2,7-phenanthrenediyl group, a 5,12-naphthacenediyl group, a 2,7-fluorenediyl group, a 3,6-fluorenediyl group, 1,6-pyrenediyl group, and a 3,8-perylenediyl group, and the arylene group may have the substituent above.

As Ar³ in the formula (2), a 1,3-phenylene group, a 1,4-phenylene group, a 2,6-naphthalenediyl group, a 2,7-naphthalenediyl group, a 2,6-anthracenediyl group, a 9,10-anthracenediyl group, a 2,7-phenanthrenediyl group, a 2,7-fluorenediyl group, and a 3,6-fluorenediyl group are preferable because the luminance life of the light-emitting device to be obtained is more excellent in the case where the polymer compound according to the present embodiment is used in production of the light-emitting device.

In the formula (2), examples of the divalent heterocyclic group in Ar³ include a 2,5-pyrrolediyl group, a 2,1,3-benzothiadiazole-4,7-diyl group, a dibenzofurandiyl group, and a dibenzothiophenediyl group, and the divalent heterocyclic group may have the substituent above.

In the formula (2), as the divalent group in which two or more same or different groups selected from arylene groups and divalent heterocyclic groups are linked in Ar³, a group represented by the above formula (1a-1), (1a-2), (1a-3), (1a-4), (1a-5), (1a-6), or (1a-7) can be selected, and the divalent group may have the substituent above.

Examples of the second constitutional unit include the constitutional units represented by the following formulas (2-1) to (2-36). Among the constitutional units represented by the formulas (2-1) to (2-36), the constitutional units represented by the formulas (2-1), (2-2), (2-3), (2-4), (2-5), (2-6), (2-7), (2-8), (2-9), (2-10), (2-11), (2-12), (2-13), (2-14), (2-21), (2-22), (2-23), (2-25), (2-27), (2-28), (2-30), (2-32), (2-33), (2-35), and (2-36) are preferable, the constitutional units represented by the formulas (2-1), (2-2), (2-3), (2-4), (2-5), (2-6), (2-7), (2-8), (2-9), (2-10), (2-11), (2-12), (2-13), (2-14), (2-28), and (2-30) are more preferable, and the constitutional units represented by the formulas (2-1), (2-2), (2-4), (2-5), (2-12), (2-13), (2-14), and (2-30) are still more preferable because the luminance life of the light-emitting device to be obtained is more excellent in the case where the polymer compound is used in production of the light-emitting device.

[Chemical Formula 21]
(2-1)
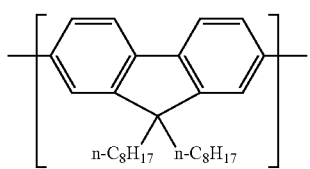
(2-2)
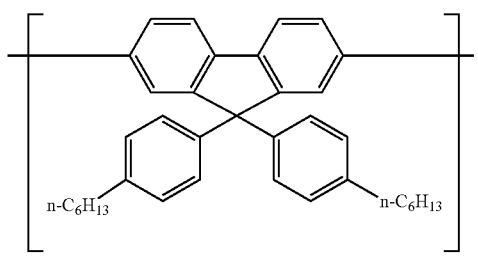
(2-3)
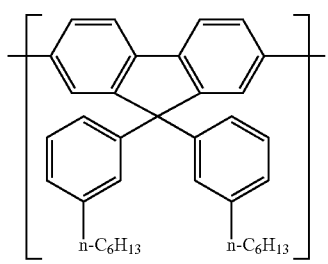
(2-4)
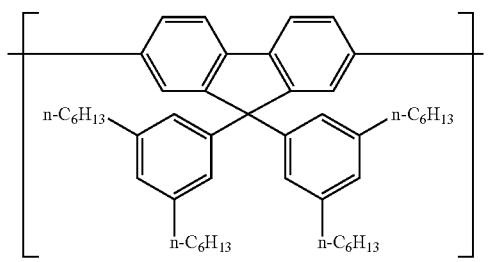
(2-5)
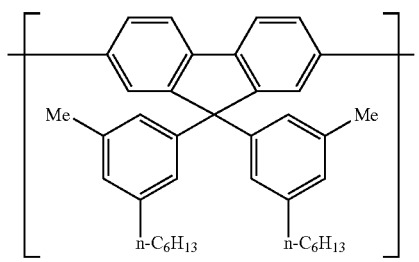
(2-6)
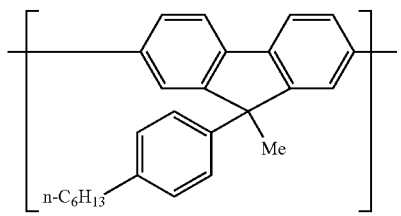
(2-7)
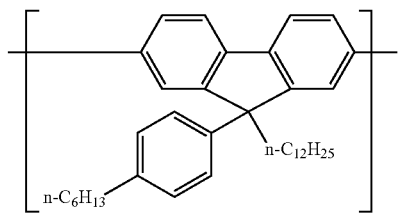
(2-8)
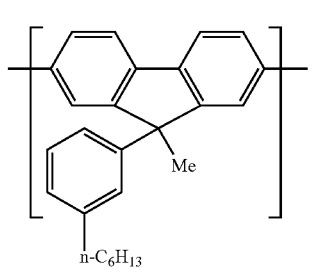
[Chemical Formula 22]
(2-9)
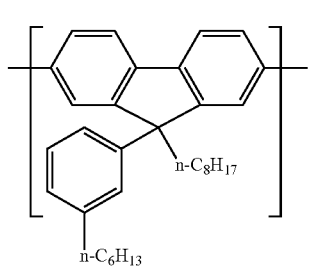
(2-10)
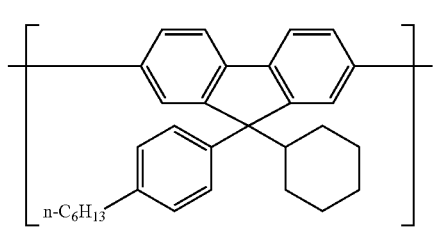
(2-11)
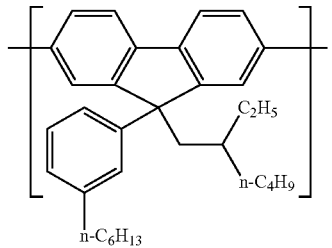
(2-12)
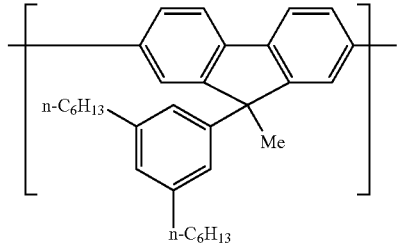

(2-13) 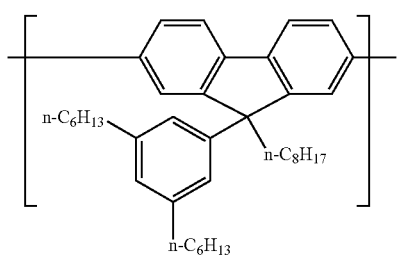
(2-14) 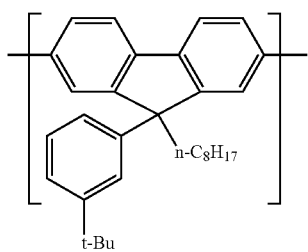
(2-15) 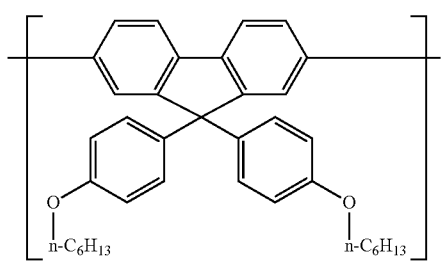
(2-16) 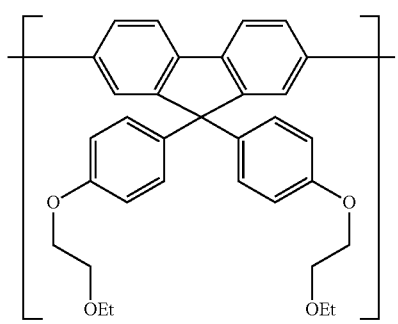
[Chemical Formula 23]
(2-17) 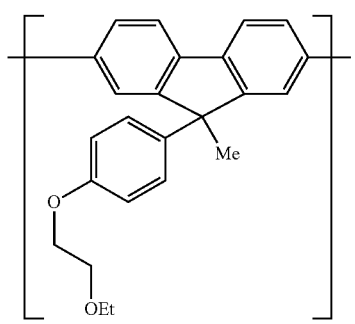
(2-18) 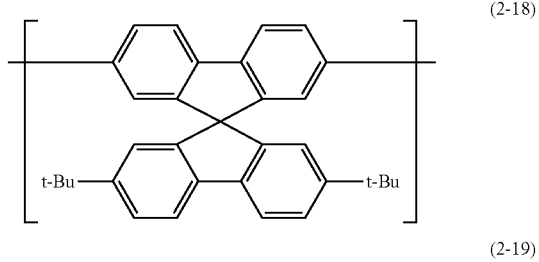
(2-19) 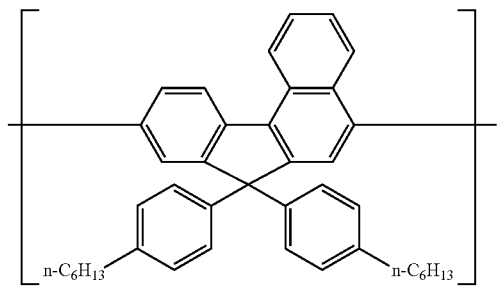
(2-20) 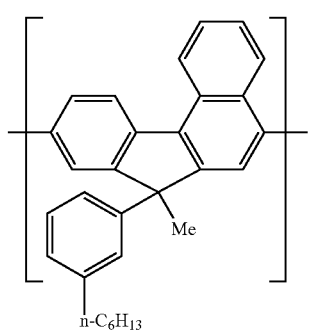
(2-21) 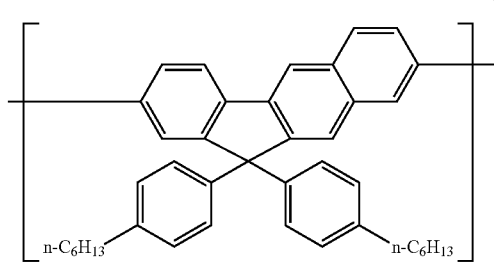
(2-22) 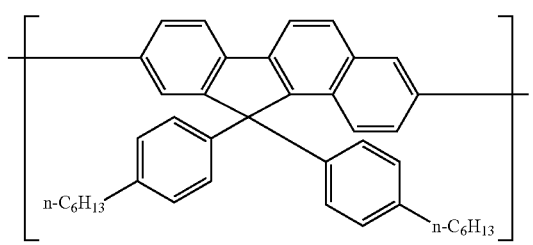
(2-23) 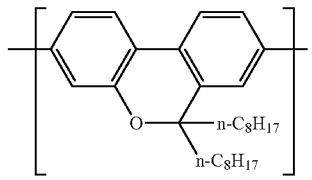

[Chemical Formula 24]
(2-24)
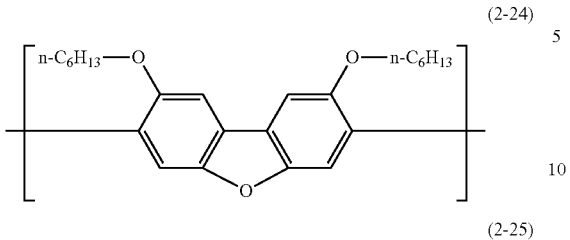
(2-25)
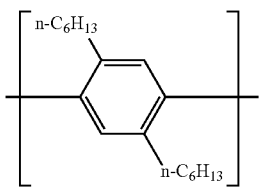
(2-26)
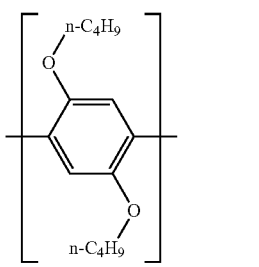
(2-27)
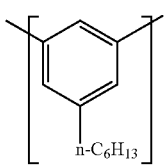
(2-28)
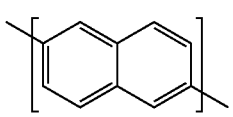
(2-29)
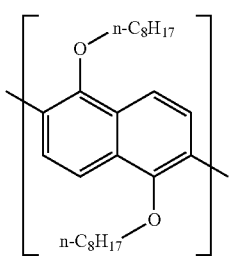
(2-30)
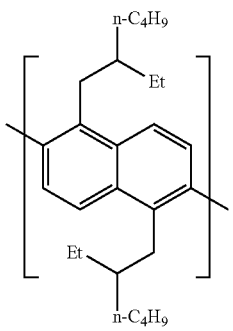
(2-31)
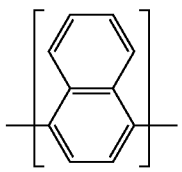
(2-32)
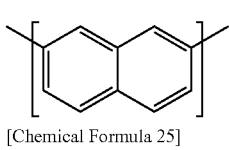
[Chemical Formula 25]
(2-33)
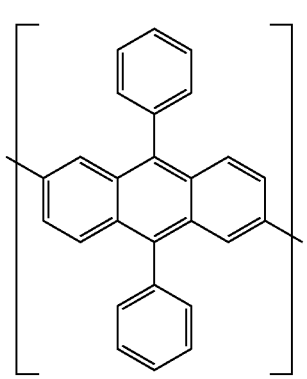
(2-34)
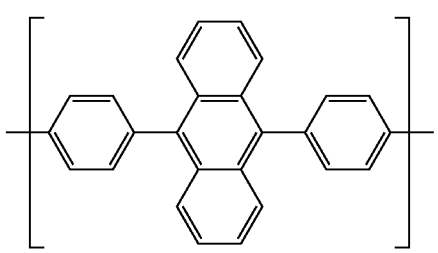
(2-35)
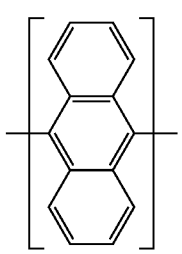
(2-36)
As the second constitutional unit, the constitutional unit represented by the following formula (3) (constitutional unit including the group represented by the following formula (3')) is also preferable:

[Chemical Formula 26]

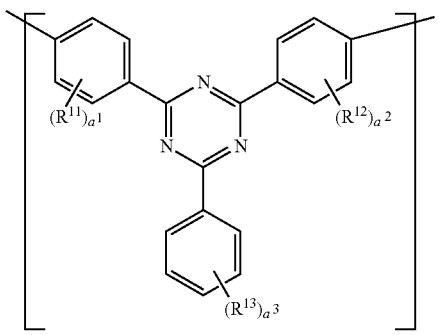

(3)

[Chemical Formula 27]

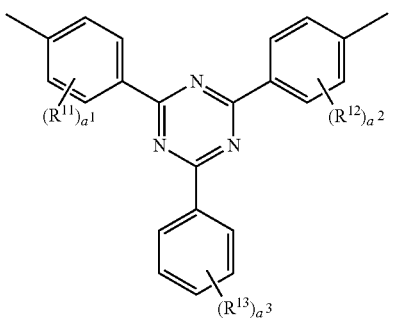

(3')

In the formula (3) and the formula (3'), $a^1$ and $a^2$ each independently represent an integer of 0 to 4; $a^3$ represents an integer of 0 to 5. $R^{11}$, $R^{12}$, and $R^{13}$ each independently represent an unsubstituted or substituted alkyl group, an unsubstituted or substituted alkoxy group, an unsubstituted or substituted aryl group, an unsubstituted or substituted aryloxy group, an unsubstituted or substituted monovalent heterocyclic group, an unsubstituted or substituted alkoxycarbonyl group, an unsubstituted or substituted silyl group, a halogen atom, a $R^{13}$, carboxyl group, or a cyano group. When $R^{11}$, $R^{12}$, $R^{13}$, and $R^{14}$ exist in plural, the plurality of $R^{11}$, $R^{12}$, $R^{13}$, or $R^{14}$ may be the same or different from each other.

In the formula (3) and the formula (3'), it is preferable that $a^1$ and $a^2$ be an integer of 0 to 2, and $a^3$ be an integer of 1 to 3 because the luminance life of the light-emitting device using the polymer compound according to the present embodiment is more excellent.

In the formula (3) and the formula (3'), in the case where the group represented by $R^{11}$, $R^{12}$, and $R^{13}$ has a substituent, the substituent is preferably an alkyl group, an alkoxy group, an aryl group, an aryloxy group, an arylalkyl group, an arylalkoxy group, an arylalkenyl group, an arylalkynyl group, an amino group, a substituted amino group, a halogen atom, an acyl group, an acyloxy group, a monovalent heterocyclic group, a carboxyl group, a nitro group, and a cyano group, more preferably an alkyl group, an alkoxy group, an aryl group, an aryloxy group, an arylalkyl group, an arylalkoxy group, a substituted amino group, an acyl group, a cyano group, and still more preferably an alkyl group, an alkoxy group, and an aryl group.

In the formula (3) and the formula (3'), examples of $R^{11}$, $R^{12}$, and $R^{13}$ include an unsubstituted or substituted alkyl group, an unsubstituted or substituted alkoxy group, and an unsubstituted or substituted aryl group. Here, examples of the substituted alkyl group in $R^{11}$, $R^{12}$, and $R^{13}$ include an arylalkyl group or an alkylarylalkyl group. Examples of the substituted alkoxy group in $R^{11}$, $R^{12}$, and $R^{13}$ include an arylalkoxy group and an alkoxy group substituted with an alkoxy group. Examples of the substituted aryl group in $R^{11}$, $R^{12}$, and $R^{13}$ include an alkyl aryl group.

It is preferable that $R^{11}$, $R^{12}$, and $R^{13}$ be an unsubstituted or substituted alkyl group, or an unsubstituted or substituted aryl group because the luminance life of the light-emitting device using the polymer compound according to the present embodiment is more excellent.

It is preferable that as the second constitutional unit, the polymer compound have a constitutional unit consisting of an unsubstituted or substituted fluorenediyl group, and it is more preferable that as the third constitutional unit, the polymer compound have a constitutional unit consisting of an unsubstituted or substituted 2,7-fluorenediyl group.

It is preferable that as the second constitutional unit, the polymer compound have a constitutional unit consisting of at least one group selected from the group consisting of an unsubstituted or substituted phenylene group, an unsubstituted or substituted naphthalenediyl group, an unsubstituted or substituted anthracenediyl group, and the group represented by the above formula (3').

It is preferable that the content (total content) of the second constitutional unit be 0.1 to 99.9 mol % of the total constitutional units, it is more preferable that the content (total content) of the third constitutional unit be 30 to 99.9 mol % of the total constitutional units, and it is still more preferable that the content (total content) of the third constitutional unit be 50 to 99.9 mol % of the total constitutional units because the luminance life of the light-emitting device to be obtained is more excellent in the case where the polymer compound is used in production of the light-emitting device.

As the second constitutional unit, the polymer compound may have only one constitutional unit above, or may have a plurality of different constitutional units among the constitutional units above. The polymer compound may have the first constitutional unit, the third constitutional unit described later, the constitutional unit including an unsubstituted or substituted fluorenediyl group, and the constitutional unit including an unsubstituted or substituted phenylene group.

The polymer compound may have the first constitutional unit, the third constitutional unit, the constitutional unit including an unsubstituted or substituted fluorenediyl group, and the constitutional unit including an unsubstituted or substituted naphthalenediyl group.

The polymer compound may have the first constitutional unit, the third constitutional unit, the constitutional unit including an unsubstituted or substituted fluorenediyl group, and the constitutional unit including an unsubstituted or substituted anthracenediyl group.

The polymer compound may have the first constitutional unit, the third constitutional unit, the constitutional unit including an unsubstituted or substituted fluorenediyl group, and the constitutional unit represented by the above formula (3).

(Third Constitutional Unit)

The third constitutional unit is a constitutional unit represented by the following formula (4):

[Chemical Formula 28]

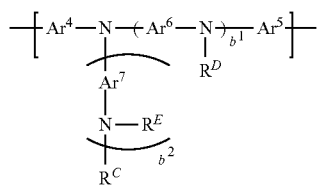

(4)

wherein $b^1$ and $b^2$ each independently represent 0 or 1; $Ar^4$, $Ar^5$, $Ar^6$, and $Ar^7$ each independently represent an unsubstituted or substituted arylene group, an unsubstituted or substituted divalent heterocyclic group, or a divalent group in which two or more same or different groups selected from arylene groups and divalent heterocyclic groups are linked (the group may have a substituent); $R^C$, $R^D$, and $R^E$ each independently represent a hydrogen atom, an unsubstituted or substituted alkyl group, an unsubstituted or substituted aryl group, or an unsubstituted or substituted monovalent heterocyclic group; $Ar^4$, $Ar^5$, $Ar^6$, and $Ar^7$ may be linked to each other to form a ring structure.

In the formula (4), it is more preferable that $b^1$ be 1 because the luminance life of the light-emitting device using the polymer compound according to the present embodiment is more excellent.

In the formula (4), it is preferable that $b^2$ be 0 because synthesis of the monomer is easy and the light emission efficiency of the light-emitting device using the polymer compound according to the present embodiment is more excellent.

In the formula (4), it is preferable that $R^C$, $R^D$, and $R^E$ be a substituted alkyl group, an unsubstituted or substituted aryl group, or an unsubstituted or substituted monovalent heterocyclic group, and it is more preferable that $R^C$, $R^D$, and $R^E$ be an unsubstituted or substituted aryl group because the stability of the polymer compound according to the present embodiment is good and the luminance life of the light-emitting device using the polymer compound is more excellent.

In the case where the groups represented by $Ar^4$, $Ar^5$, $Ar^6$, and $Ar^7$ have a substituent in the formula (4), examples of the substituent include an alkyl group, an alkoxy group, an aryl group, an aryloxy group, an arylalkyl group, an arylalkoxy group, an arylalkenyl group, an arylalkynyl group, an amino group, a substituted amino group, a halogen atom, an acyl group, an acyloxy group, a monovalent heterocyclic group, a carboxyl group, a nitro group, and a cyano group; the substituent is preferably an alkyl group, an alkoxy group, an aryl group, an aryloxy group, an arylalkyl group, an arylalkoxy group, a substituted amino group, acyl group, and a cyano group, and more preferably an alkyl group, an alkoxy group, and an aryl group.

In the formula (4), it is preferable that the groups represented by $Ar^4$, $Ar^5$, $Ar^6$, and $Ar^7$ be an unsubstituted or substituted arylene group or an unsubstituted or substituted divalent heterocyclic group, and particularly an unsubstituted or substituted arylene group because the stability of the polymer compound according to the present embodiment is good and the luminance life of the light-emitting device using the polymer compound is more excellent.

In the formula (4), examples of the arylene group in $Ar^4$, $Ar^5$, $Ar^6$, and $Ar^7$ include a 1,2-phenylene group, a 1,3-phenylene group, a 1,4-phenylene group, a 1,4-naphthalenediyl group, a 2,6-naphthalenediyl group, a 2,7-naphthalenediyl group, a 2,6-anthracenediyl group, a 9,10-anthracenediyl group, a 2,7-phenanthrenediyl group, a 5,12-naphthacenediyl group, a 2,7-fluorenediyl group, a 3,6-fluorenediyl group, a 1,6-pyrenediyl group, a 2,7-pyrenediyl group, or a 3,8-perylenediyl group; the 1,4-phenylene group, the 2,7-fluorenediyl group, the 2,6-anthracenediyl group, the 9,10-anthracenediyl group, the 2,7-phenanthrenediyl group, and the 1,6-pyrenediyl group are preferable; these may have a substituent.

In the formula (4), examples of the divalent heterocyclic group in the $Ar^4$, $Ar^5$, $Ar^6$, and $Ar^7$ include a 2,5-pyrrolediyl group, a dibenzofurandiyl group, a dibenzothiophenediyl group, and a 2,1,3-benzothiadiazole-4,7-diyl group; these may have a substituent. The divalent heterocyclic group represented by $Ar^4$, $Ar^5$, $Ar^6$, and $Ar^7$ is different from the group represented by the formula (5).

In the formula (4), examples of the divalent group in which two or more same or different groups selected from arylene groups and divalent heterocyclic groups are linked in $Ar^4$, $Ar^5$, $Ar^6$, and $Ar^7$ include a group represented by the above formula (1a-1), (1a-2), (1a-3), (1a-4), (1a-5), (1a-6), or (1a-7); the group represented by the above formula (1a-1) is preferable; these may have a substituent.

In the case where the groups represented by $R^C$, $R^D$, and $R^E$ have a substituent in the formula (4), the substituent is preferably an alkyl group, an alkoxy group, an aryl group, an aryloxy group, an arylalkyl group, an arylalkoxy group, an arylalkenyl group, an arylalkynyl group, an amino group, a substituted amino group, a halogen atom, an acyl group, an acyloxy group, a monovalent heterocyclic group, a carboxyl group, a nitro group, and a cyano group, more preferably an alkyl group, an alkoxy group, an aryl group, an aryloxy group, an arylalkyl group, an arylalkoxy group, a substituted amino group, acyl group, and a cyano group, and still more preferably an alkyl group, an alkoxy group, and an aryl group.

In the formula (4), the alkyl group in $R^C$, $R^D$, and $R^E$ is the same "alkyl group" described as the term commonly used; the alkyl group is preferably a $C_1$ to $C_{20}$ alkyl group; these may have a substituent.

In the formula (4), the aryl group in $R^C$, $R^D$, and $R^E$ is the same "aryl group" described as the term commonly used; the aryl group is preferably a phenyl group, a 1-naphthyl group, a 2-naphthyl group, a 1-anthracenyl group, a 2-anthracenyl group, a 9-anthracenyl group, and a 2-fluorenyl group; these may have a substituent.

In the formula (4), the monovalent heterocyclic group in $R^C$, $R^D$, and $R^E$ is the same "monovalent heterocyclic group" described as the term commonly used; the monovalent heterocyclic group is preferably a pyridyl group, a pyrimidyl group, a triazyl group, and a quinolyl group; these may have a substituent.

Examples of the third constitutional unit include the constitutional units represented by the following formulas (3-a), (3-b), (3-c), and (3-d); because the luminance life of the light-emitting device using the polymer compound according to the present embodiment is more excellent, the constitutional units represented by the formulas (3-b), (3-c), and (3-d) are preferable, and the constitutional unit represented by the formula (3-c) is more preferable.

[Chemical Formula 29]

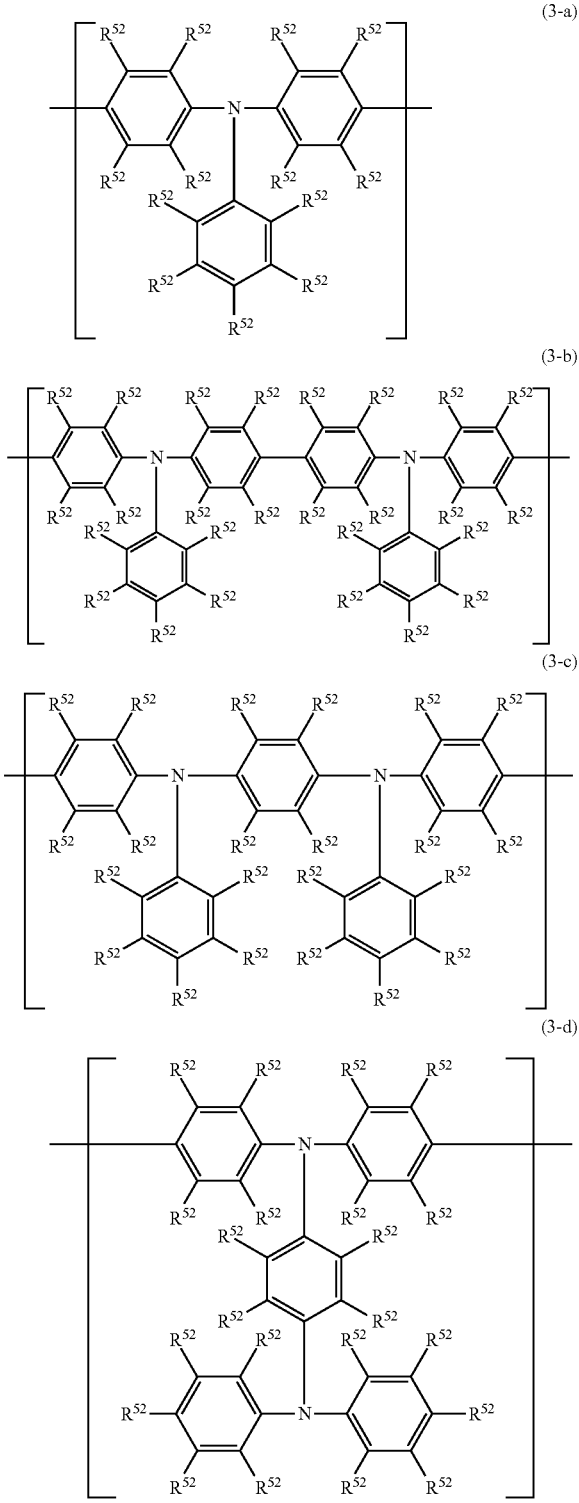

wherein $R^{52}$ represents a hydrogen atom, an alkyl group, an alkoxy group, an aryl group, an aryloxy group, an arylalkyl group, an arylalkoxy group, an arylalkenyl group, an arylalkynyl group, an amino group, a substituted amino group, a halogen atom, an acyl group, an acyloxy group, a monovalent heterocyclic group, a carboxyl group, a nitro group, or a cyano group. $R^{52}$ is preferably an alkyl group, an alkoxy group, an aryl group, an aryloxy group, an arylalkyl group, an arylalkoxy group, a substituted amino group, an acyl group, or a cyano group, and more preferably an alkyl group, an alkoxy group, or an aryl group. A plurality of $R^{52}$ present may be the same or different from each other. $R^{52}$ may form a ring with other $R^{52}$ instead of representing the group.

The third constitutional unit may be a constitutional unit represented by the following formula (2A):

[Chemical Formula 30]

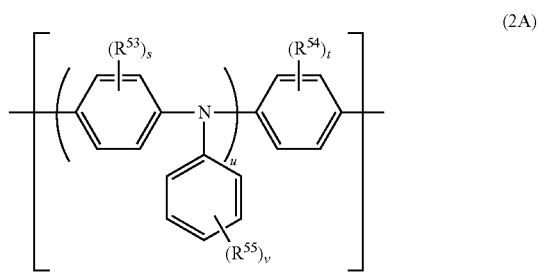

wherein s and t each independently represent an integer of 0 to 4; u is 1 or 2; v is an integer of 0 to 5; $R^{53}$, $R^{54}$, and $R^{55}$ each independently represent an alkyl group, an alkoxy group, an aryl group, an aryloxy group, an arylalkyl group, an arylalkoxy group, an arylalkenyl group, an arylalkynyl group, an amino group, a substituted amino group, a halogen atom, an acyl group, an acyloxy group, a monovalent heterocyclic group, a carboxyl group, a nitro group, or a cyano group; when $R^{53}$, $R^{54}$, and $R^{55}$ exist in plural, the plurality of $R^{53}$, $R^{54}$, or $R^{55}$ may be the same or different from each other; among the plurality of $R^{53}$ present, adjacent groups may be linked to each other to form a ring structure; and among the plurality of $R^{54}$ present, adjacent groups may be linked to each other to form a ring structure.

In the formula (2A), it is preferable that s and t each independently represent 0 to 2, u be 2, and v be 1 to 5 because the luminance life of the light-emitting device using the polymer compound according to the present embodiment is more excellent. v is more preferably 1 to 3.

In the formula (2A), it is preferable that $R^{53}$, $R^{54}$, and $R^{55}$ be an alkyl group, an alkoxy group, or an aryl group because the luminance life of the light-emitting device using the polymer compound according to the present embodiment is more excellent.

The third constitutional unit may be a constitutional unit represented by the following formula (5):

[Chemical Formula 31]

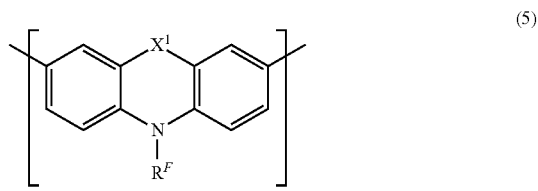

wherein $R^F$ represents a hydrogen atom, an unsubstituted or substituted alkyl group, an unsubstituted or substituted aryl group, or an unsubstituted or substituted monovalent heterocyclic group; $X^1$ represents a single bond, an oxygen atom, a sulfur atom, or a group represented by —C($R^{14}$)$_2$—; $R^{14}$ represents an unsubstituted or substituted alkyl group or an unsubstituted or substituted aryl group. A plurality of $R^{14}$ may be the same or different from each other.

It is preferable that $R^F$ be an unsubstituted or substituted alkyl group, an unsubstituted or substituted aryl group, or an unsubstituted or substituted monovalent heterocyclic group, it is more preferable that $R^F$ be an unsubstituted or substituted alkyl group or an unsubstituted or substituted aryl group, and it is still more preferable that $R^F$ be an unsubstituted or substituted aryl group because the stability of the polymer compound according to the present embodiment is good and the luminance life of the light-emitting device using the polymer compound is more excellent.

In the formula (5), it is preferable that $X^1$ be a single bond or an oxygen atom, and it is more preferable that $X^1$ be an oxygen atom because when the polymer compound is used in production of the light-emitting device, the luminance life of the light-emitting device to be obtained is more excellent.

In the case where the group represented by $R^F$ in the formula (5) has a substituent, the substituent is preferably an alkyl group, an alkoxy group, an aryl group, an aryloxy group, an arylalkyl group, an arylalkoxy group, an arylalkenyl group, an arylalkynyl group, an amino group, a substituted amino group, a halogen atom, an acyl group, an acyloxy group, a monovalent heterocyclic group, a carboxyl group, a nitro group, or a cyano group, more preferably an alkyl group, an alkoxy group, an aryl group, an aryloxy group, an arylalkyl group, an arylalkoxy group, a substituted amino group, an acyl group, or a cyano group, and still more preferably an alkyl group, an alkoxy group, or an aryl group.

In the formula (5), the alkyl group in $R^F$ is the same "alkyl group" described as the term commonly used; the alkyl group is preferably a $C_1$ to $C_{20}$ alkyl group; these may have a substituent.

In the formula (5), the aryl group in $R^F$ is the same "aryl group" described as the term commonly used; the aryl group is preferably a phenyl group, a 1-naphthyl group, a 2-naphthyl group, a 1-anthracenyl group, a 2-anthracenyl group, a 9-anthracenyl group, and a 2-fluorenyl group; these may have a substituent.

In the formula (5), the monovalent heterocyclic group in $R^F$ is the same "monovalent heterocyclic group" described as the term commonly used; the monovalent heterocyclic group is preferably a pyridyl group, a pyrimidyl group, a triazyl group, and a quinolyl group; these may have a substituent.

In the case where the group represented by $R^{14}$ in the formula (5) has a substituent, the substituent is preferably an alkyl group, an alkoxy group, an aryl group, an aryloxy group, an arylalkyl group, an arylalkoxy group, an arylalkenyl group, an arylalkynyl group, an amino group, a substituted amino group, a halogen atom, an acyl group, an acyloxy group, a monovalent heterocyclic group, a carboxyl group, a nitro group, or a cyano group, more preferably an alkyl group, an alkoxy group, an aryl group, an aryloxy group, an arylalkyl group, an arylalkoxy group, a substituted amino group, an acyl group, or a cyano group, and still more preferably an alkyl group, an alkoxy group, or an aryl group.

In the formula (5), the alkyl group in $R^{14}$ is the same "alkyl group" described as the term commonly used; the alkyl group is preferably a $C_1$ to $C_{20}$ alkyl group; these may have a substituent.

In the formula (5), the aryl group in $R^{14}$ is the same "aryl group" described as the term commonly used; the aryl group is preferably a phenyl group, a 1-naphthyl group, a 2-naphthyl group, a 1-anthracenyl group, a 2-anthracenyl group, a 9-anthracenyl group, and a 2-fluorenyl group; these may have a substituent.

Examples of the third constitutional unit include the constitutional units represented by the following formulas (3-1) to (3-12). Among the constitutional units represented by the following formulas (3-1) to (3-12), the constitutional units represented by the formulas (3-1), (3-2), (3-3), (3-4), (3-5), (3-6), (3-7), (3-8), (3-9), (3-10), and (3-12) are preferable, the constitutional units represented by the formulas (3-1), (3-2), (3-4), (3-5), (3-6), (3-7), (3-8), (3-9), and (3-10) are more preferable, and the constitutional units represented by the formulas (3-2), (3-4), (3-8), and (3-9) are still more preferable because the luminance life of the light-emitting device to be obtained is more excellent in the case where the polymer compound is used in production of the light-emitting device.

[Chemical Formula 32]

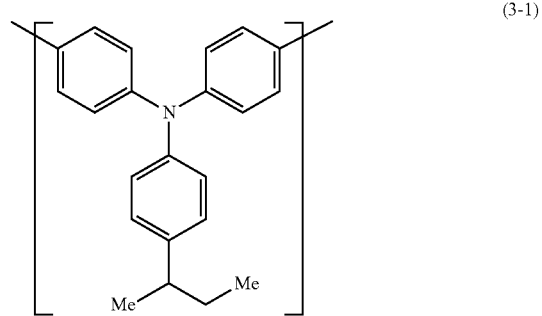

(3-1)

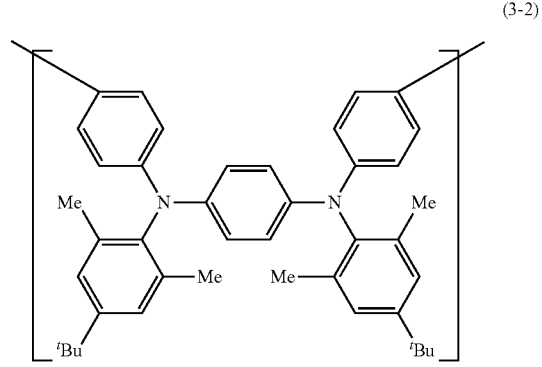

(3-2)

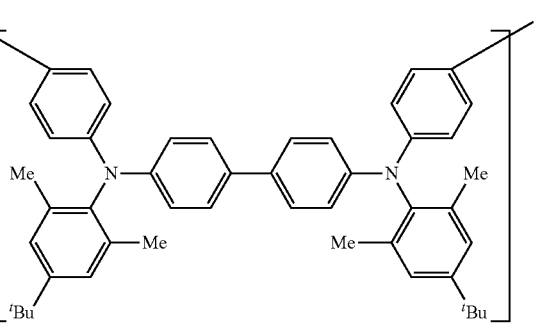

(3-3)

(3-4)
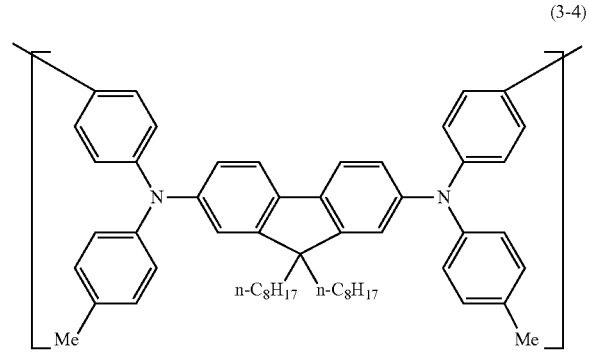
(3-5)
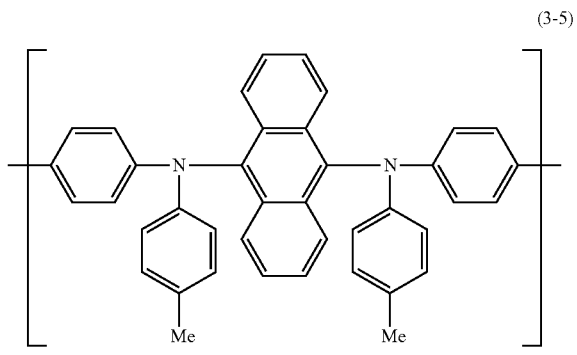
[Chemical Formula 33]
(3-6)
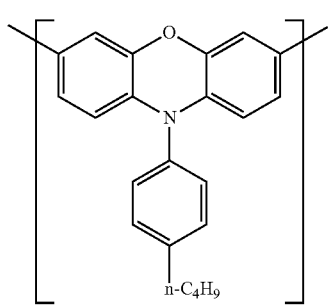
(3-7)
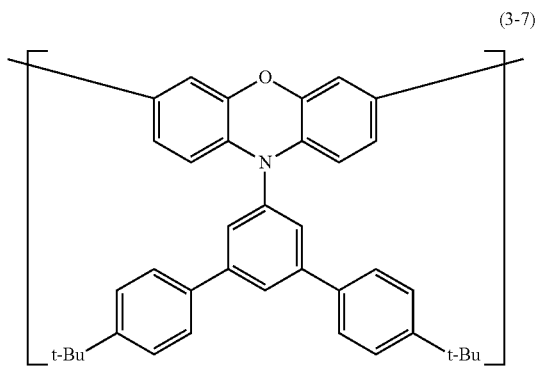
(3-8)
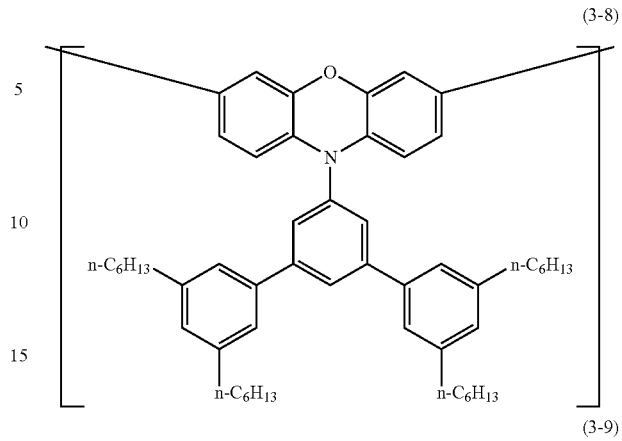
(3-9)
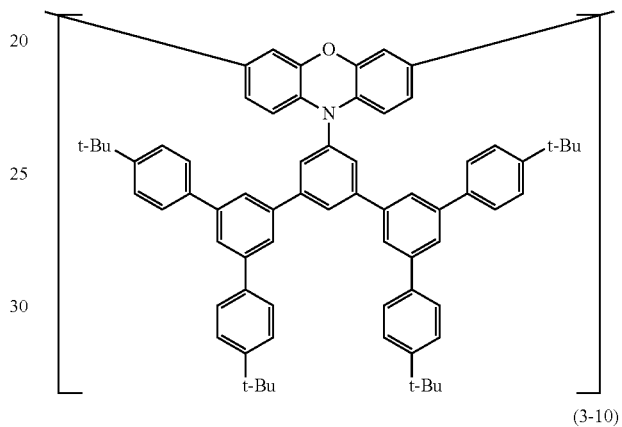
(3-10)
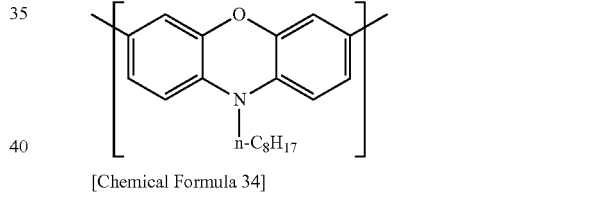
[Chemical Formula 34]
(3-11)
(3-12)
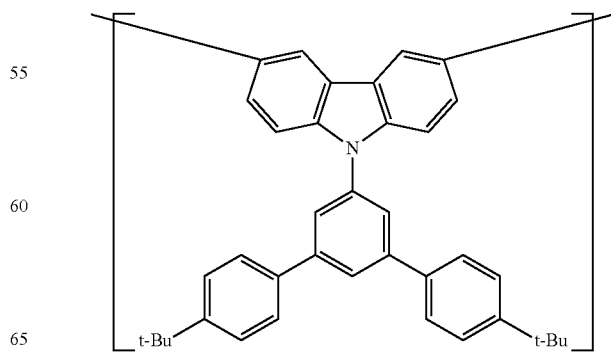

It is preferable that the content of the third constitutional unit be 0.1 to 70 mol % of all the constitutional units, it is more preferable that the content of the third constitutional unit be 0.1 to 50 mol % of all the constitutional units, and it is still more preferable that the content of the third constitutional unit be 0.1 to 40 mol % of all the constitutional units because the luminance life of the light-emitting device to be obtained is more excellent in the case where the polymer compound is used in production of the light-emitting device.

As the third constitutional unit, the polymer compound may have only one constitutional unit, or may have a plurality of different constitutional units among the constitutional units above.

Examples of a combination of the constitutional units in the polymer compound are shown below:

[Chemical Formula 35]

(P1)

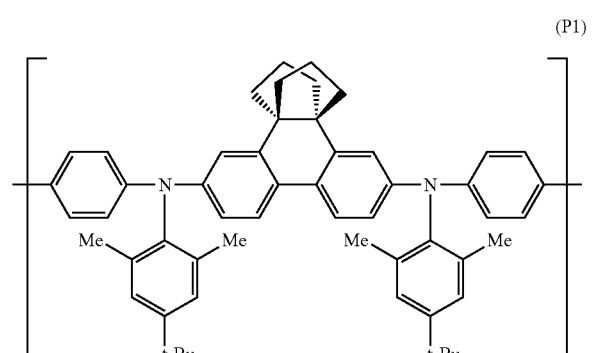

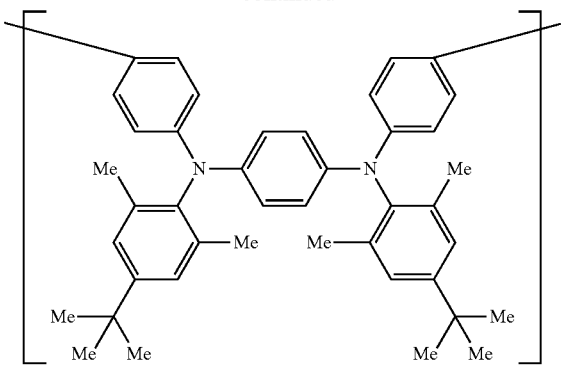

(P3)

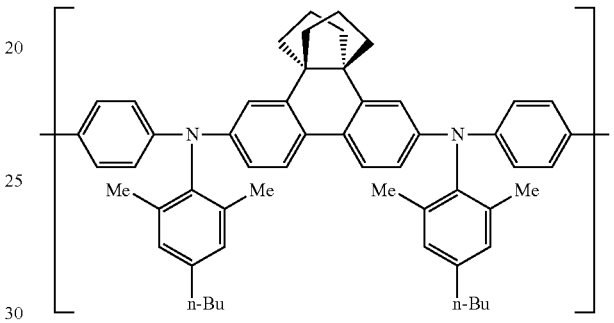

(P2)

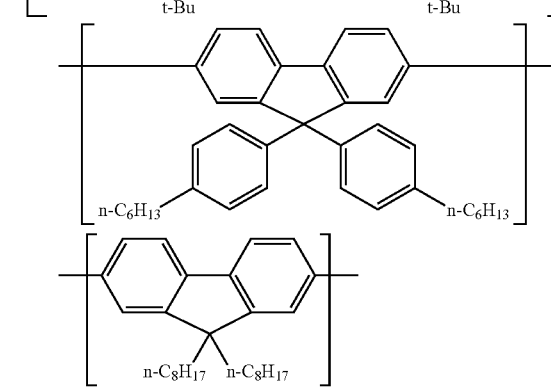

(P4)

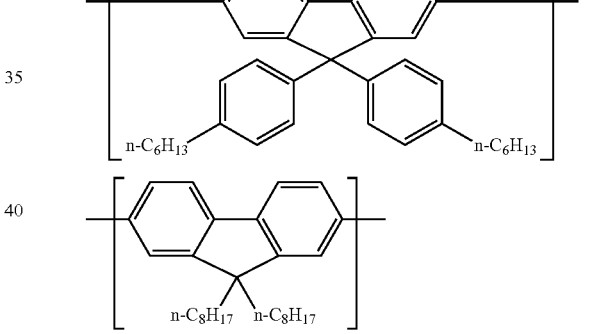

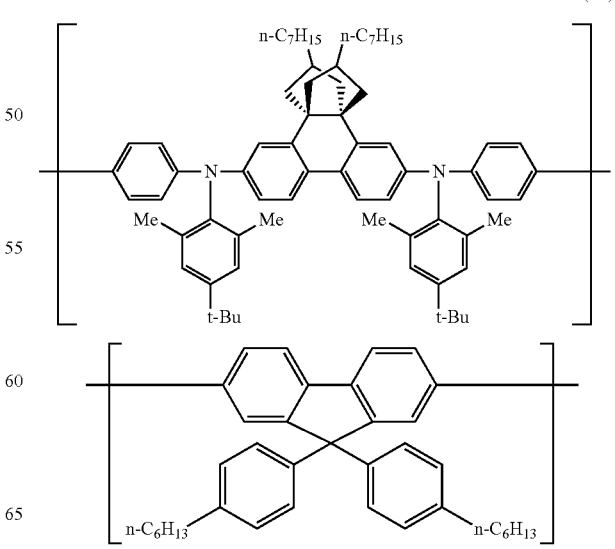

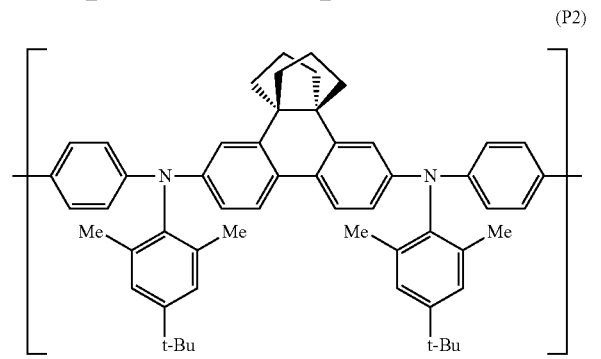

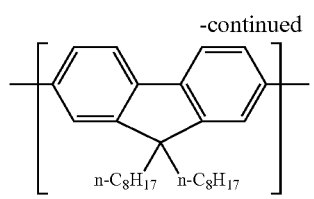
[Chemical Formula 36]
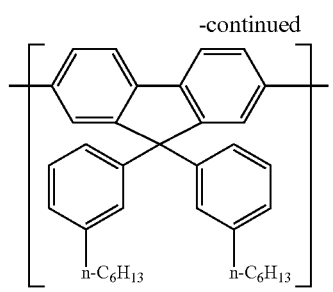
(P5)
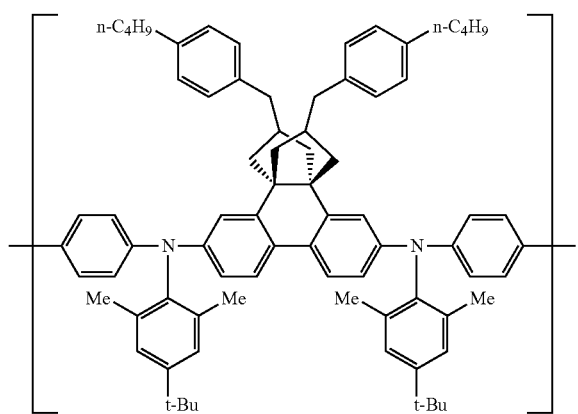
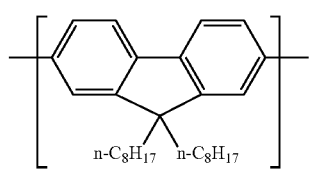
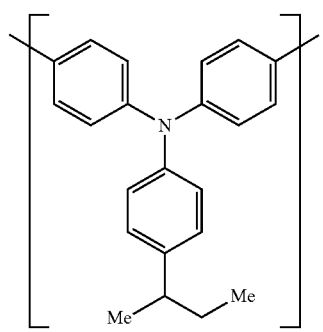
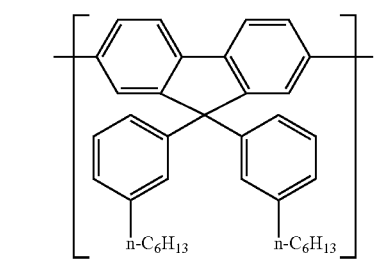
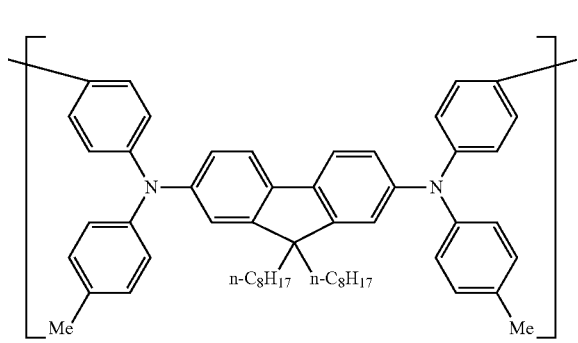
(P7)
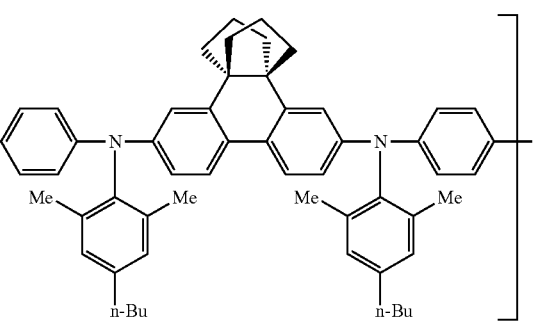
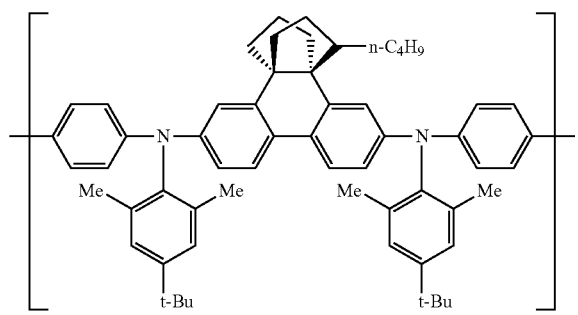
(P6)
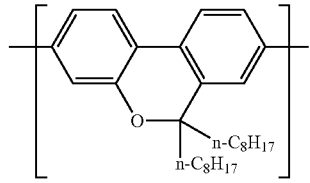
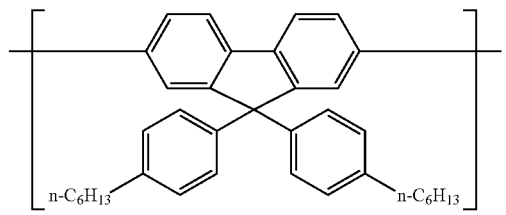

-continued
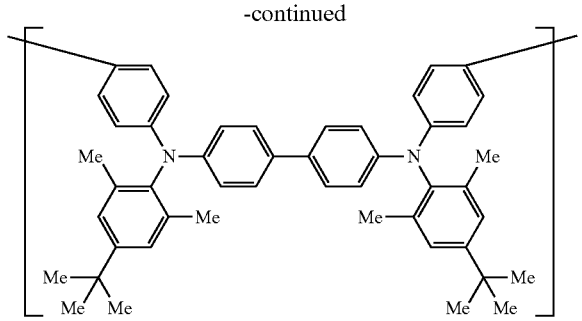
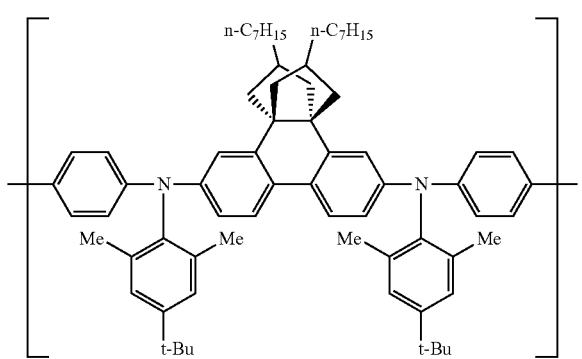
(P8)
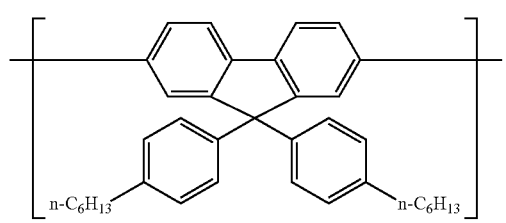
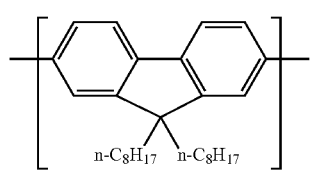
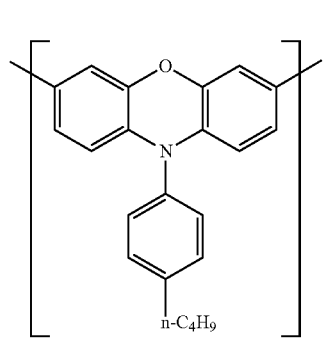
[Chemical Formula 37]
(P9)
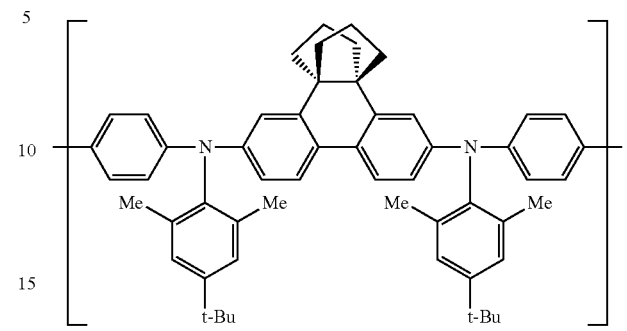
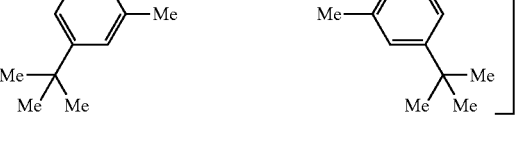
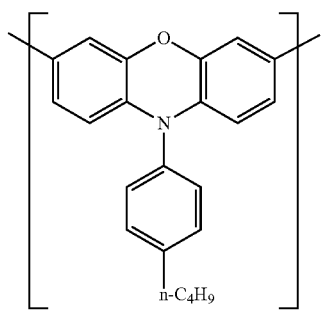
(P10)
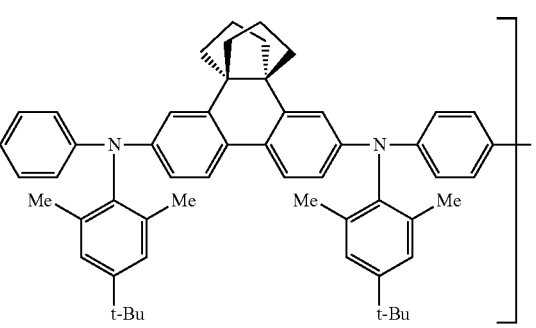

-continued
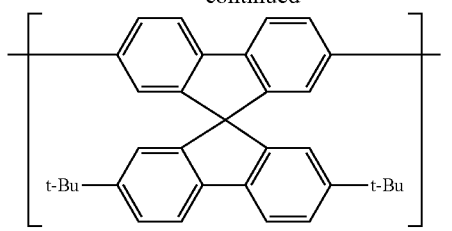
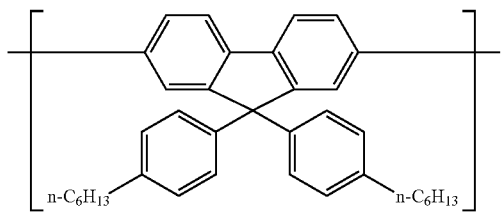
(P11)
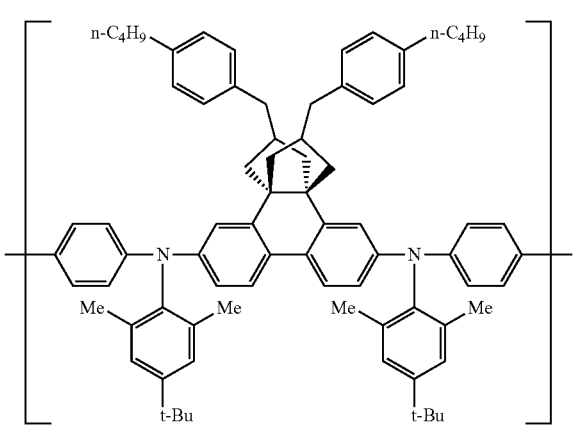
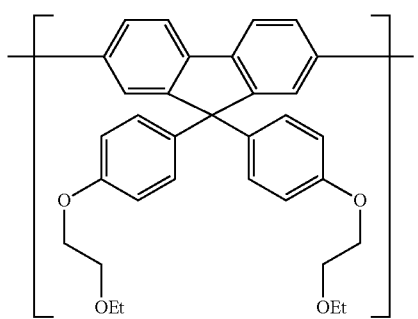
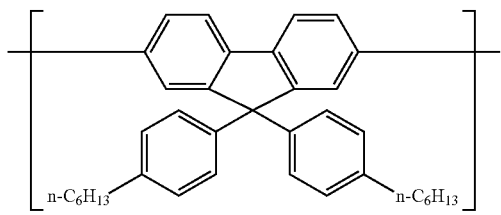
-continued
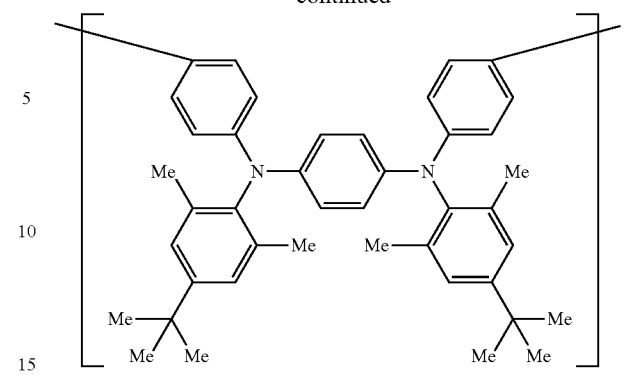
(P12)
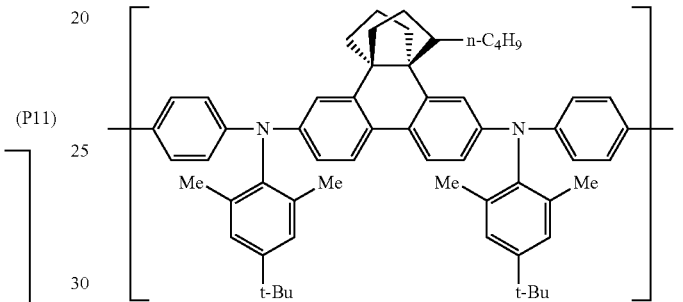
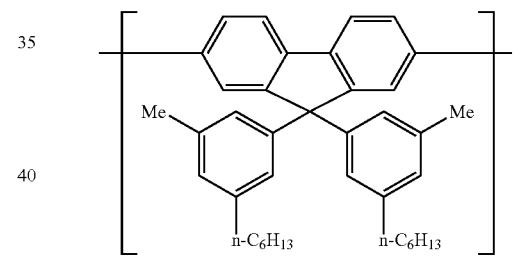
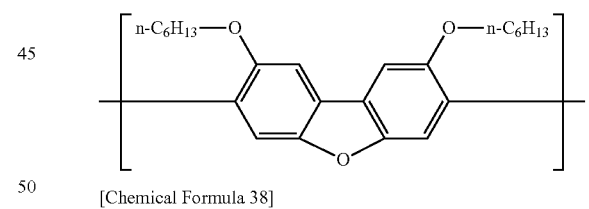
[Chemical Formula 38]
(P13)
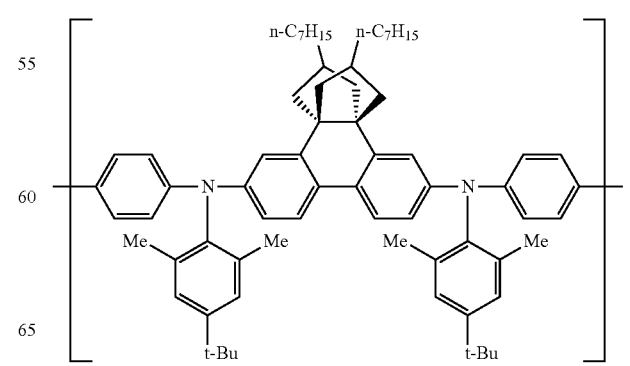

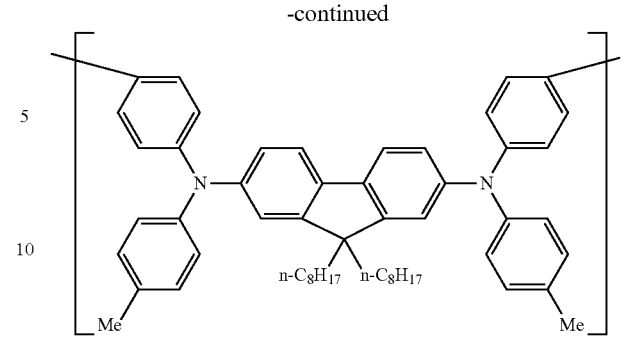
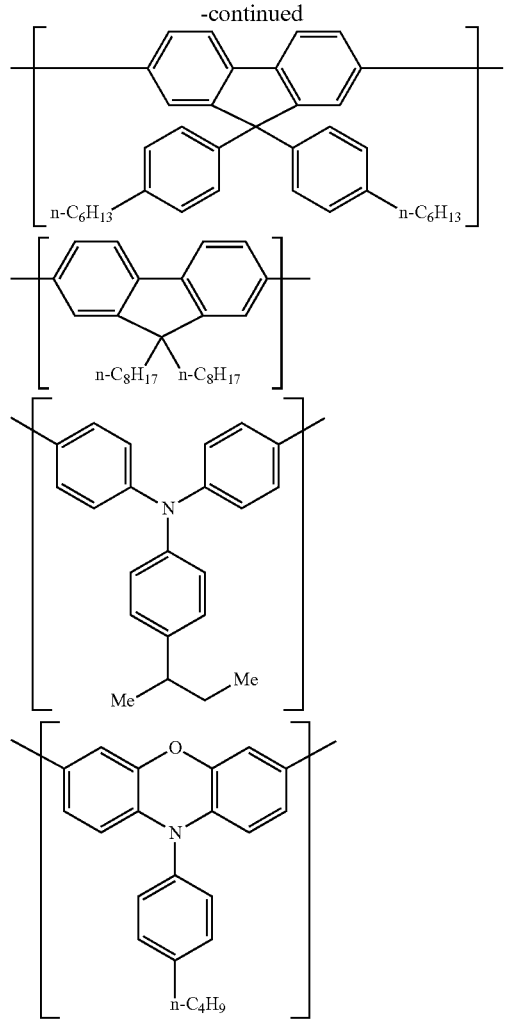
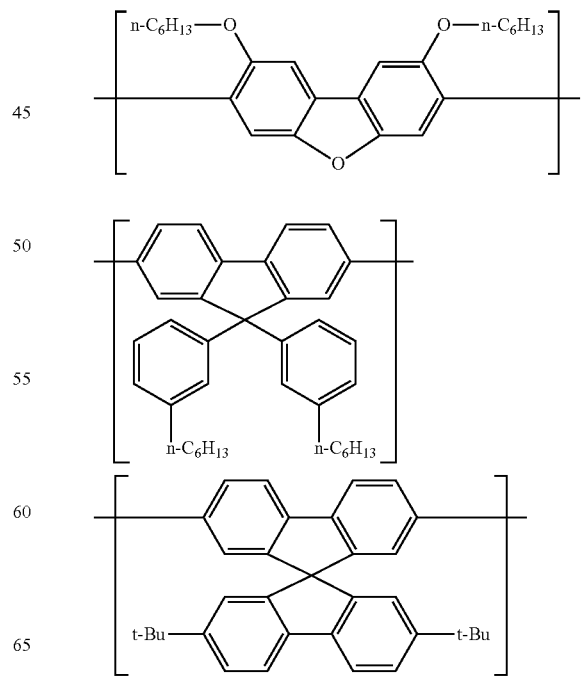

(P16)
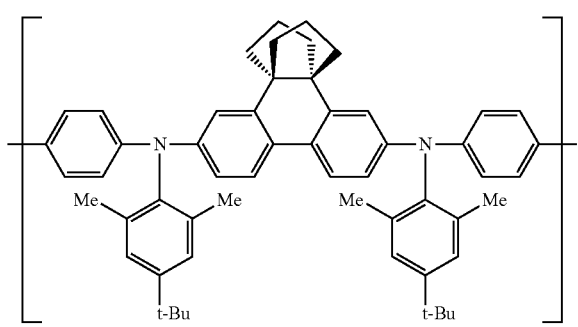
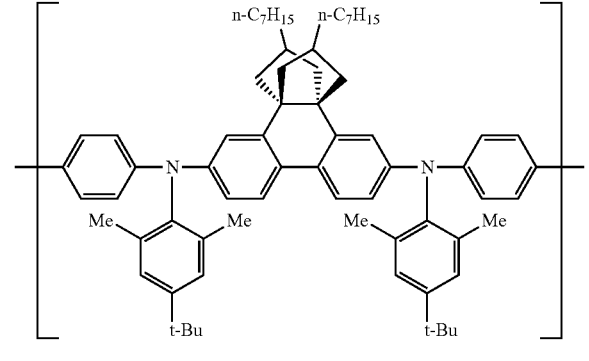
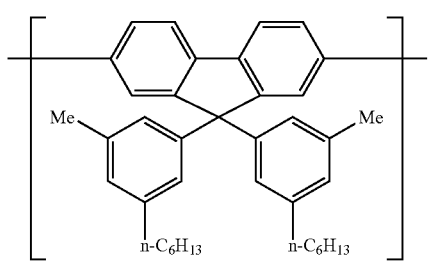
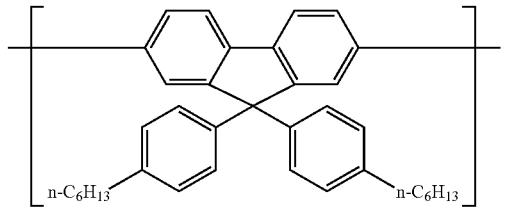
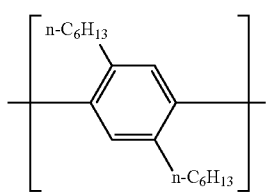
(P18)
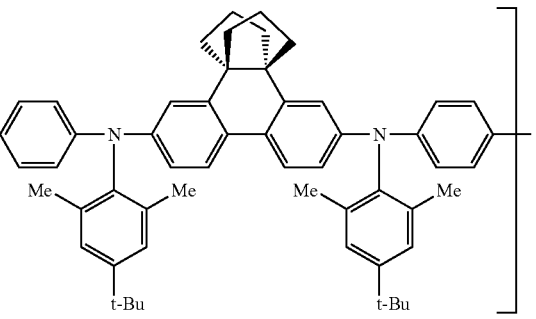
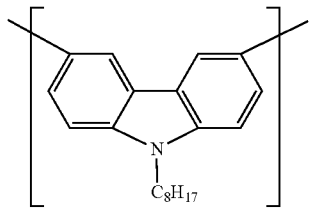
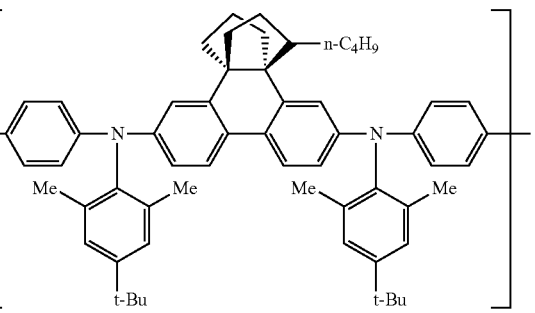
[Chemical Formula 39]
(P17)
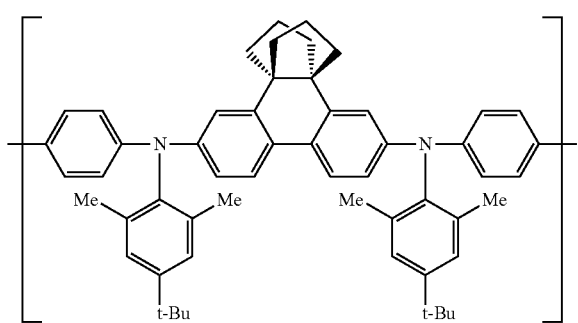
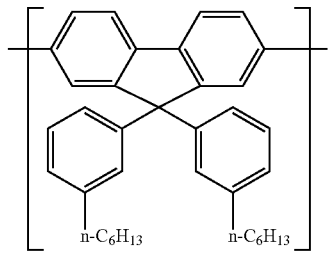

-continued
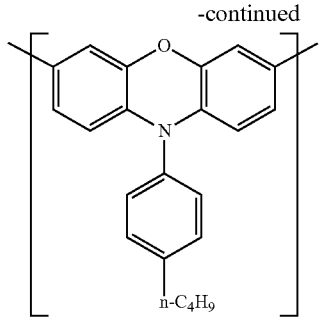
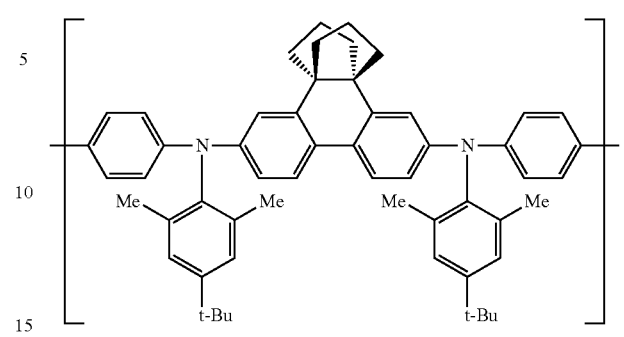
(P19)
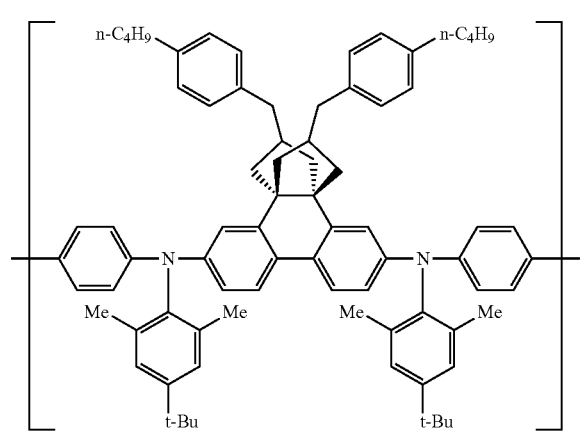
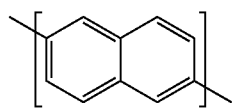
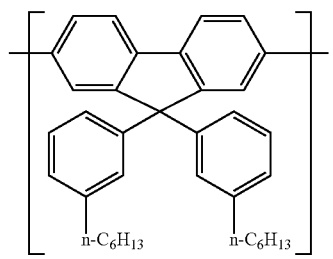
[Chemical Formula 40]
(P21)
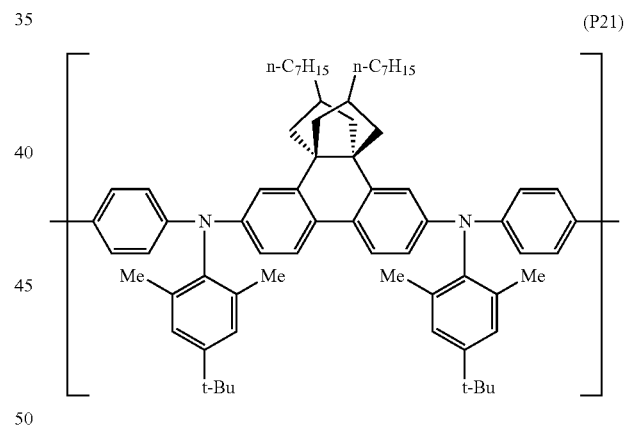
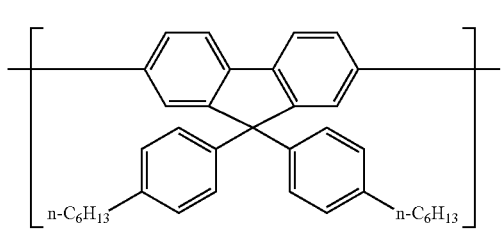
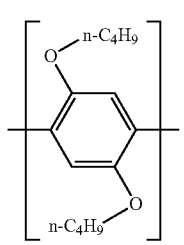
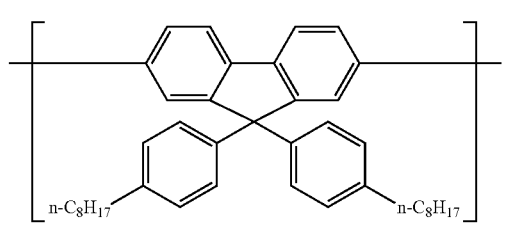
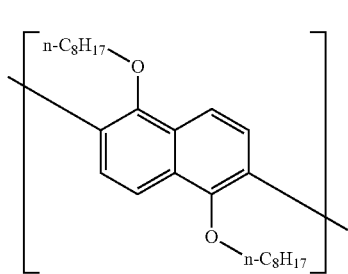
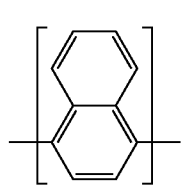

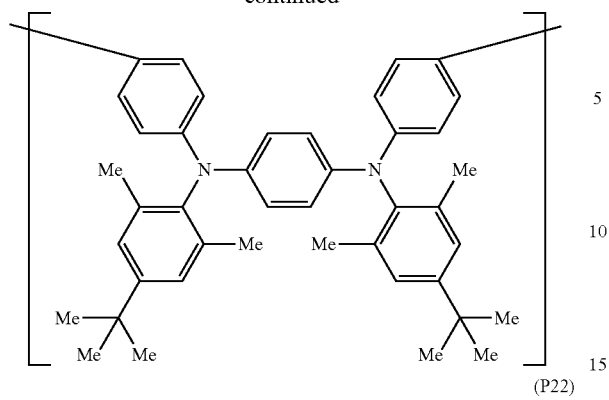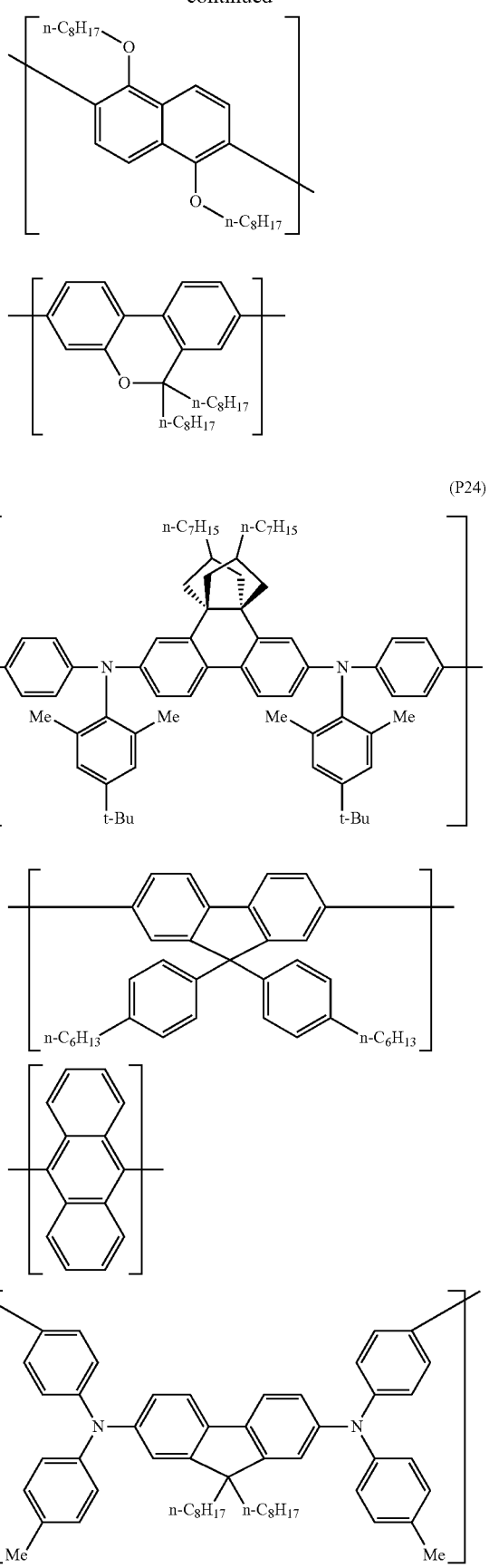

[Chemical Formula 41]
(P25)
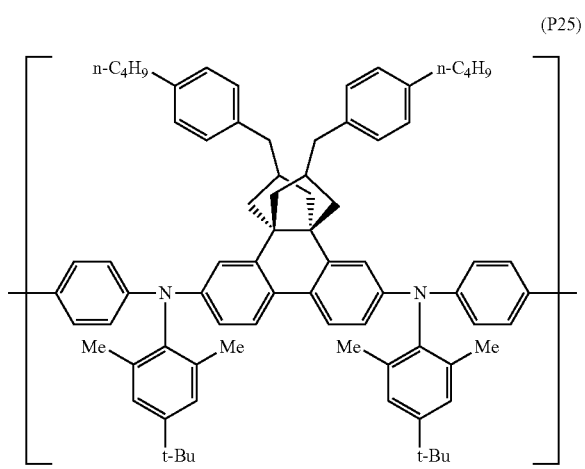
(P26)
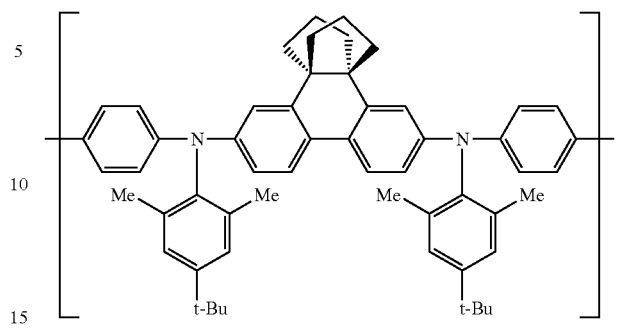
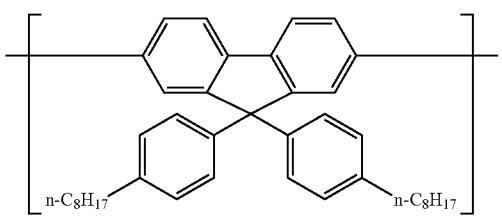
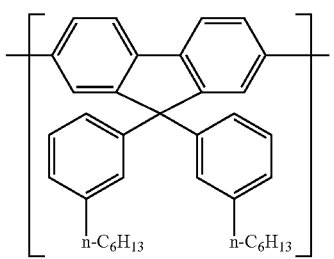
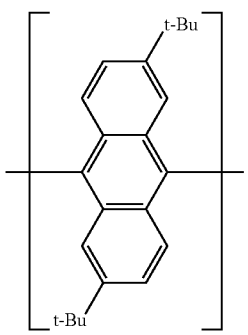
(P27)
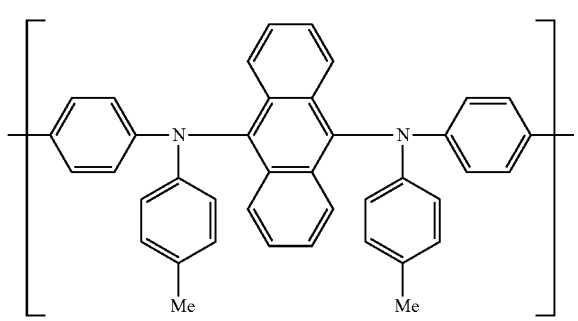
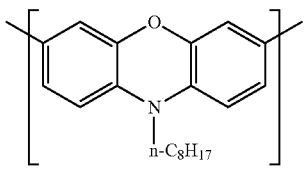
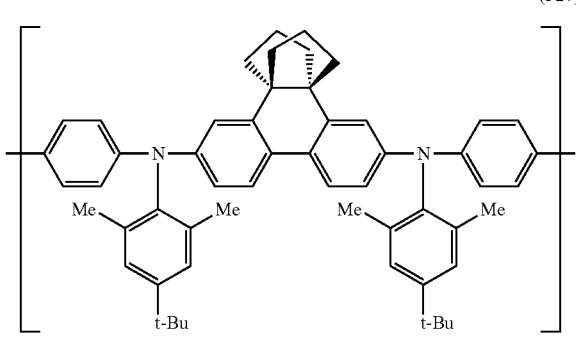
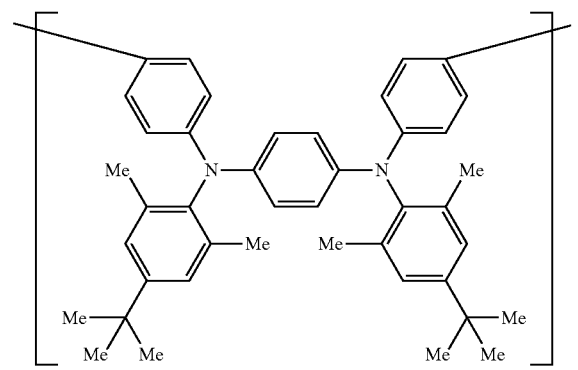
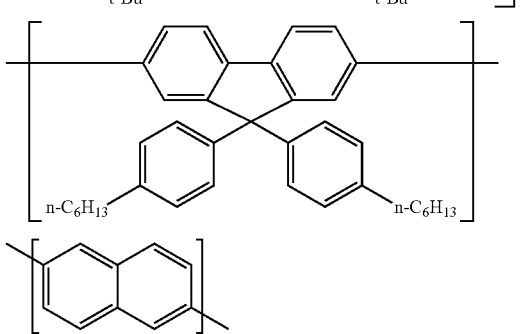
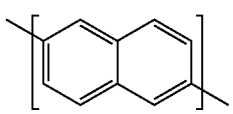

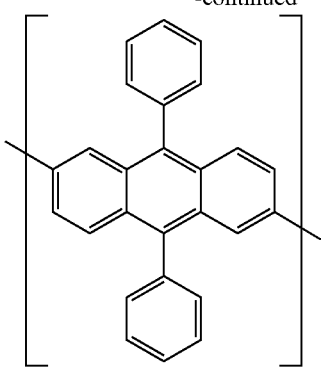
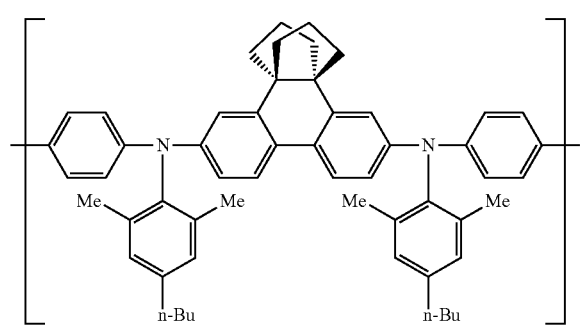
(P28)
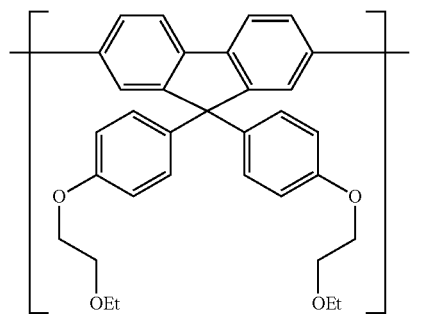
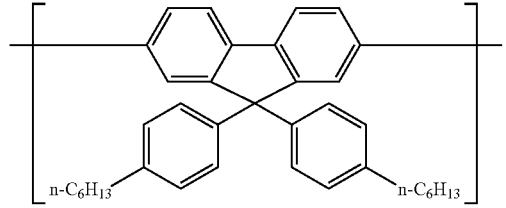
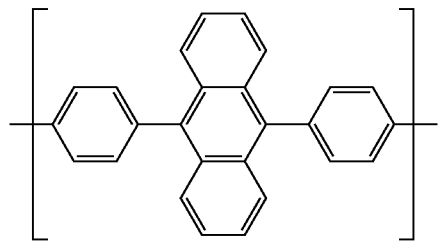
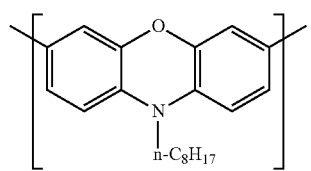
[Chemical Formula 42]
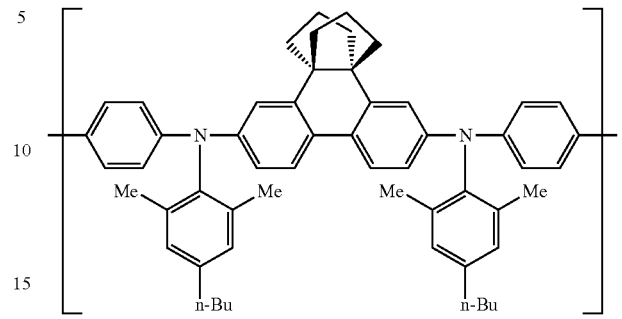
(P29)
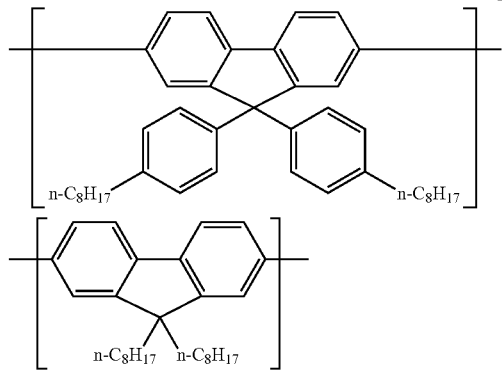
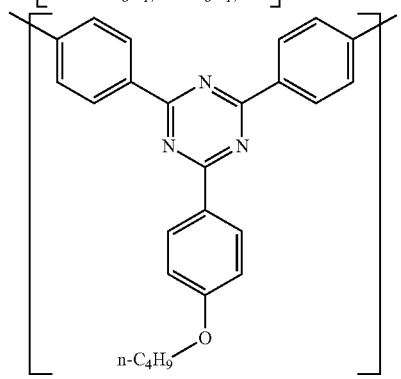
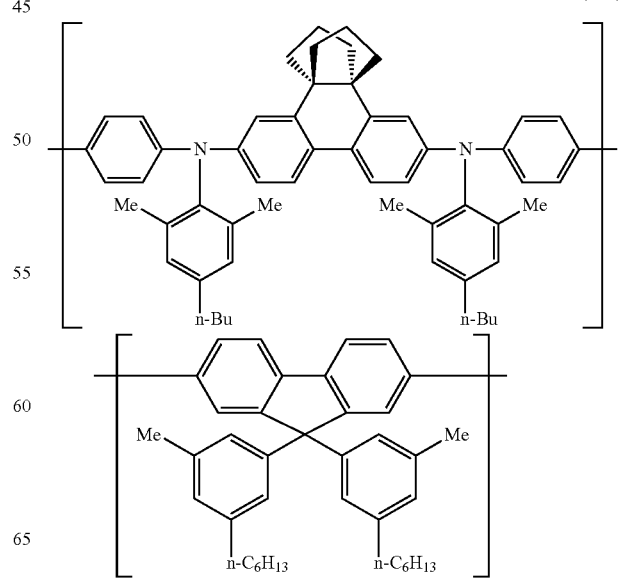
(P30)

69
-continued
70
-continued
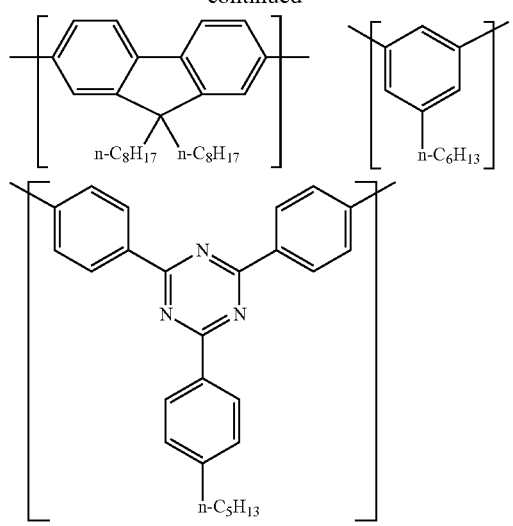
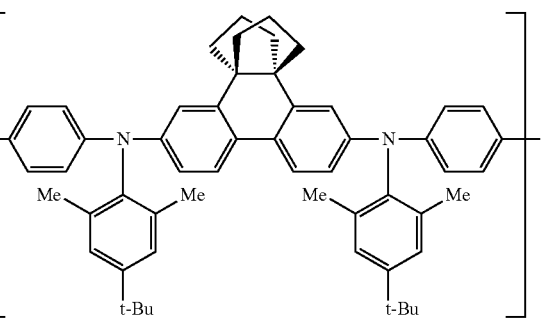
(P31)
(P32)
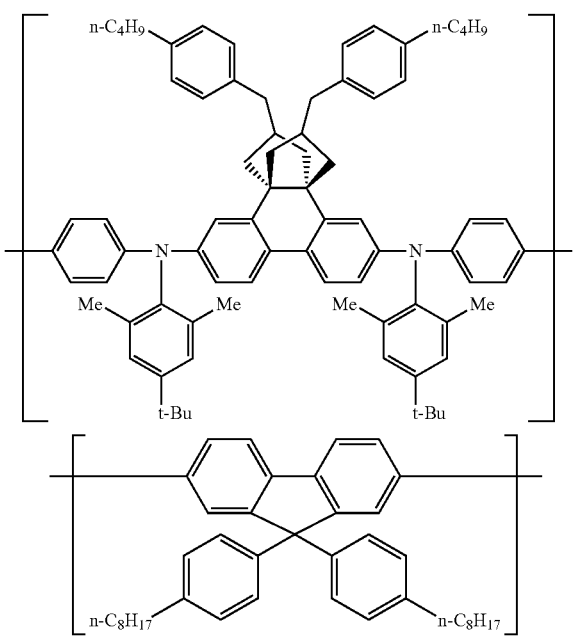
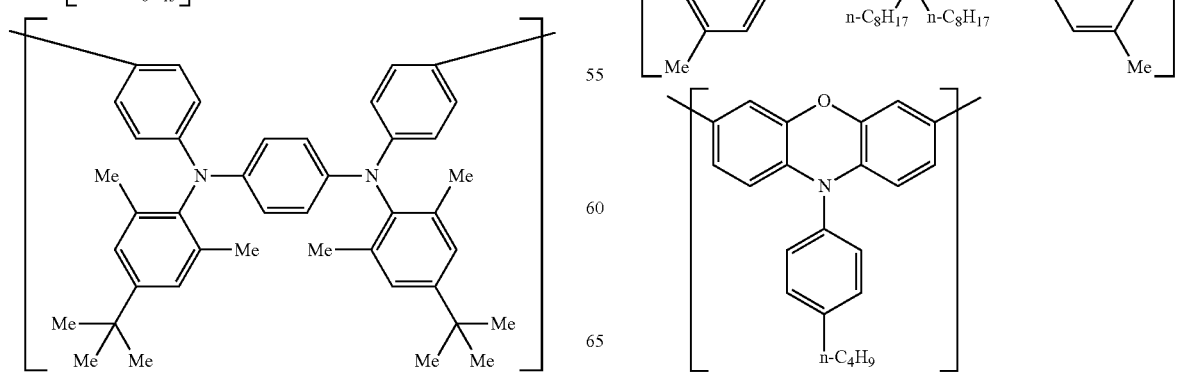

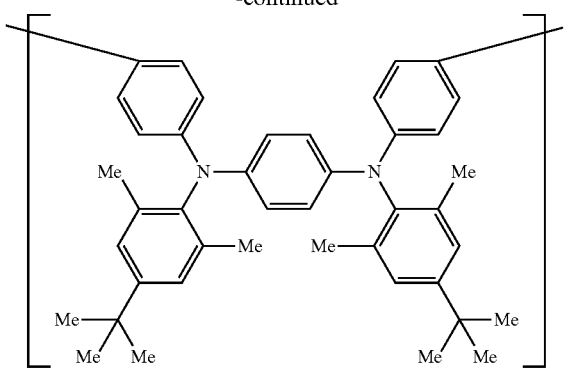
[Chemical Formula 43]
(P33)
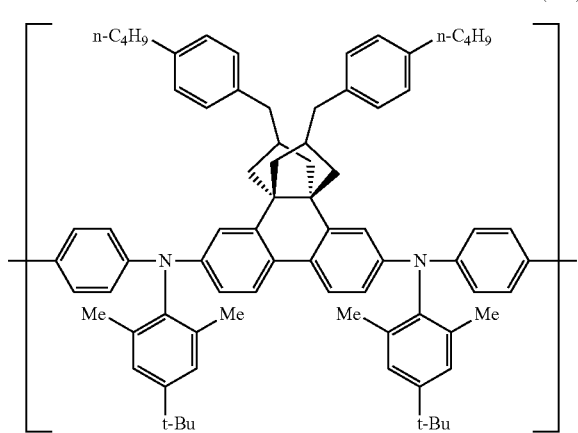
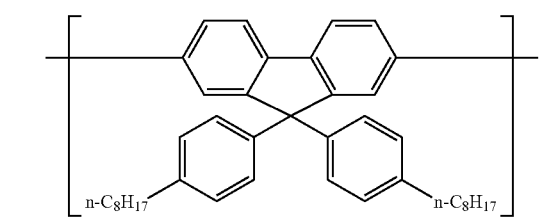
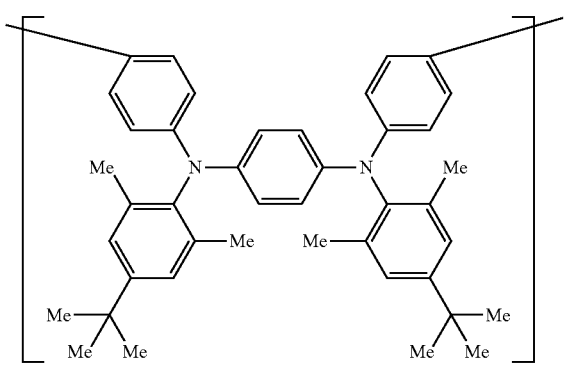
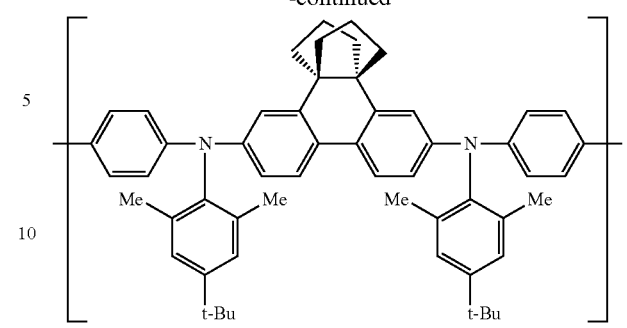
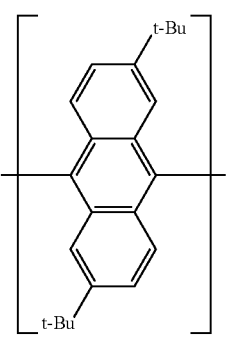
(P34)
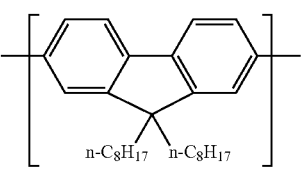
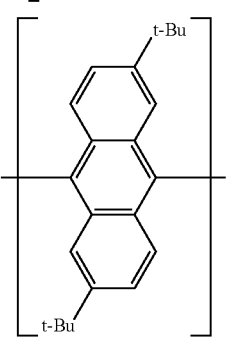

73
-continued
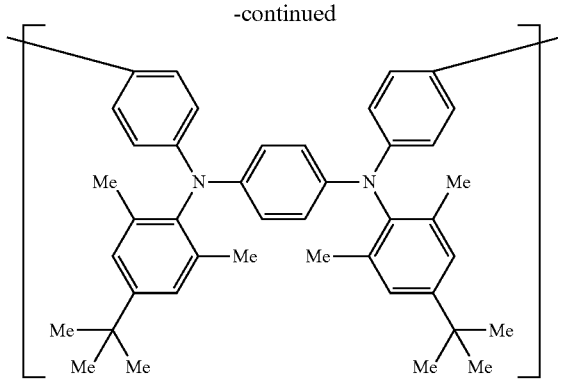
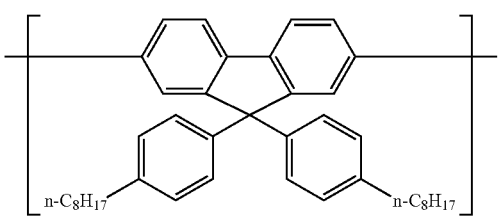
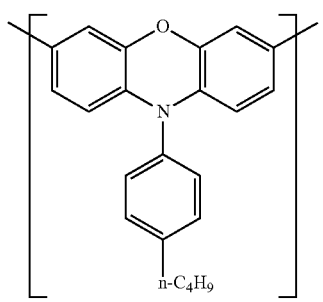
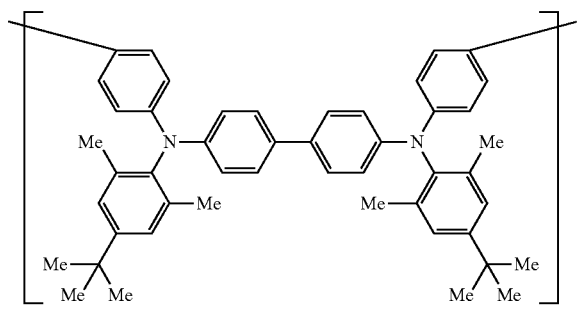
[Chemical Formula 44]
(P35)
74
-continued
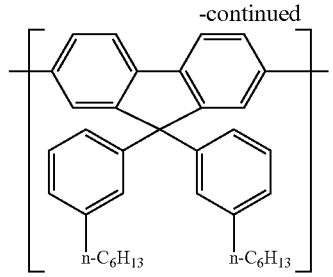
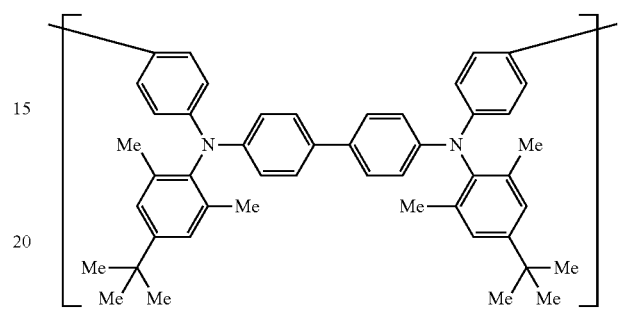
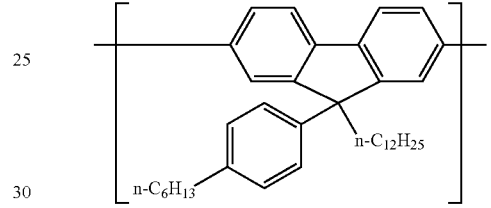
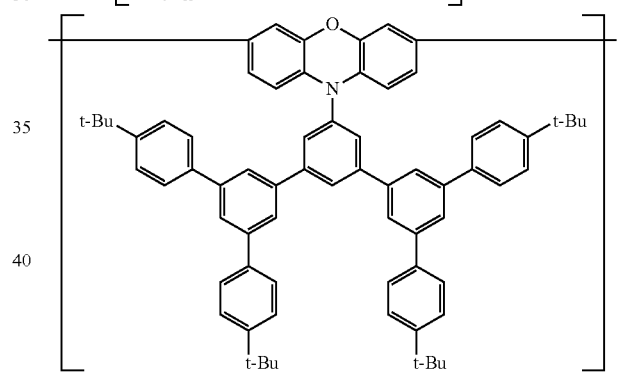
(P36)
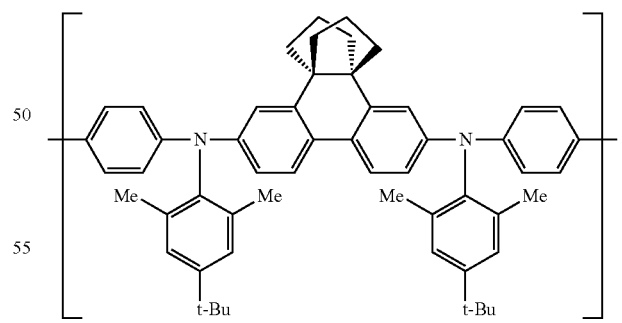

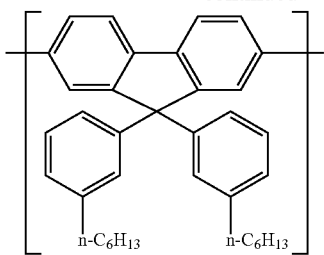
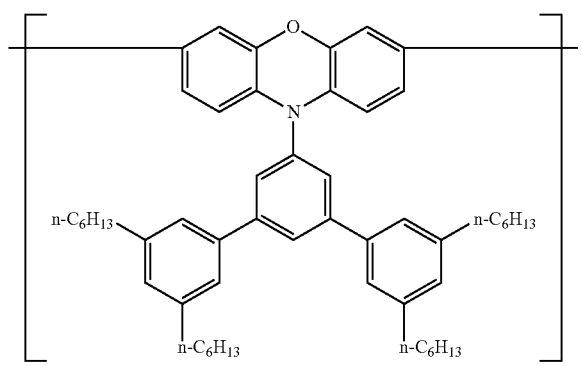
(P37)
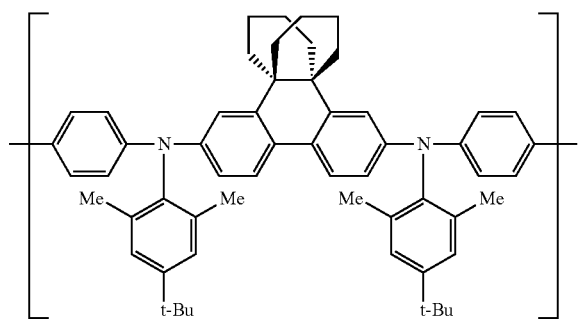
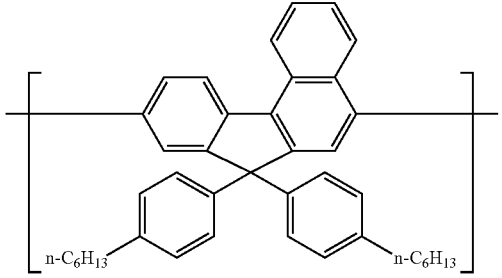
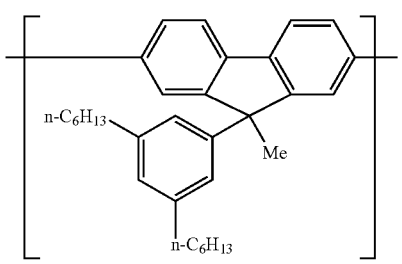
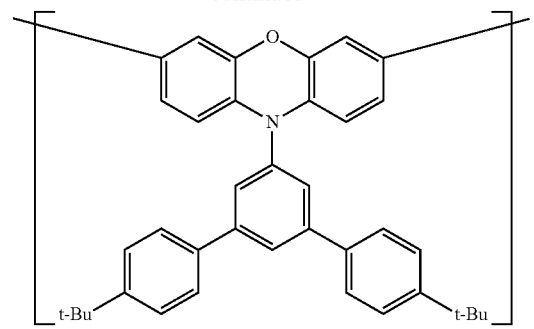
(P38)
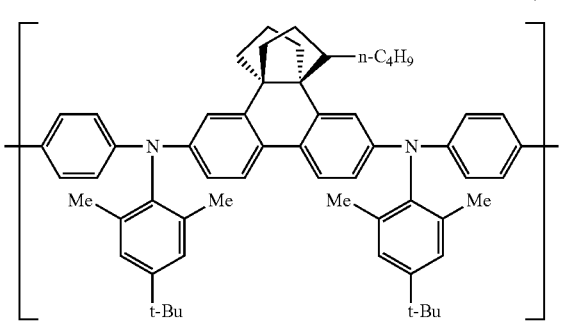
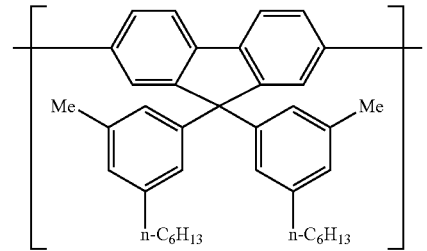
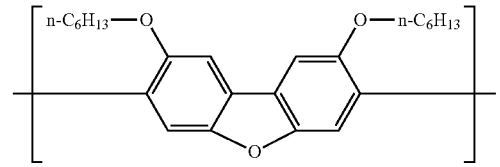
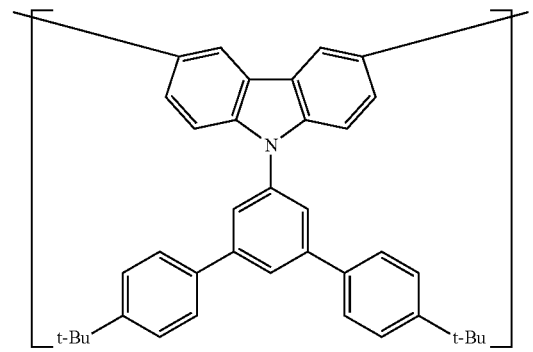

-continued
[Chemical Formula 45]
(P39)
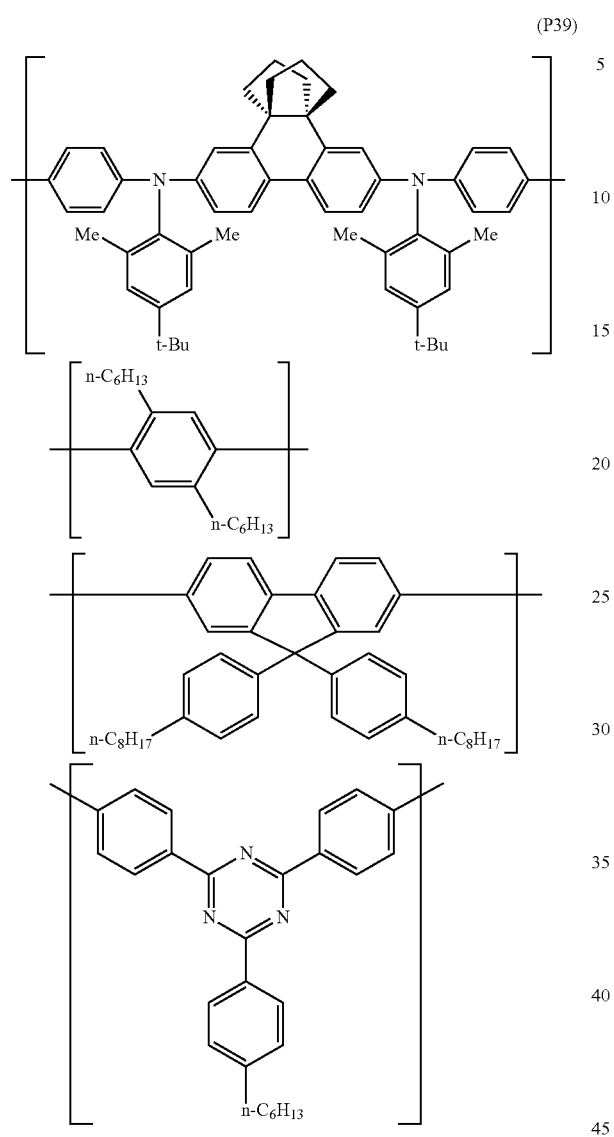
(P40)
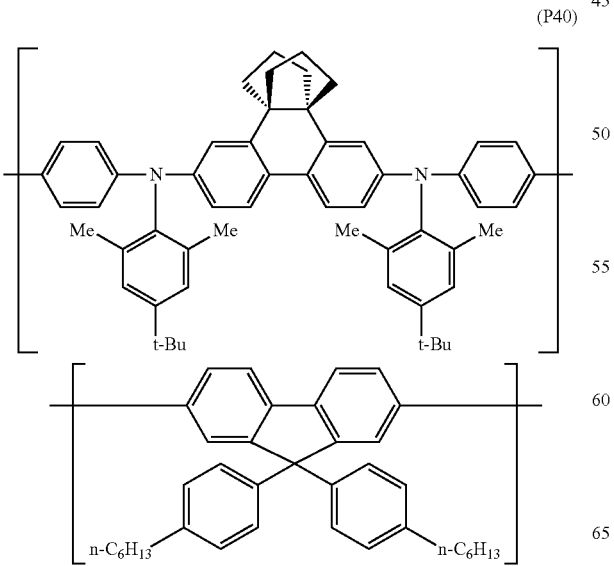
-continued
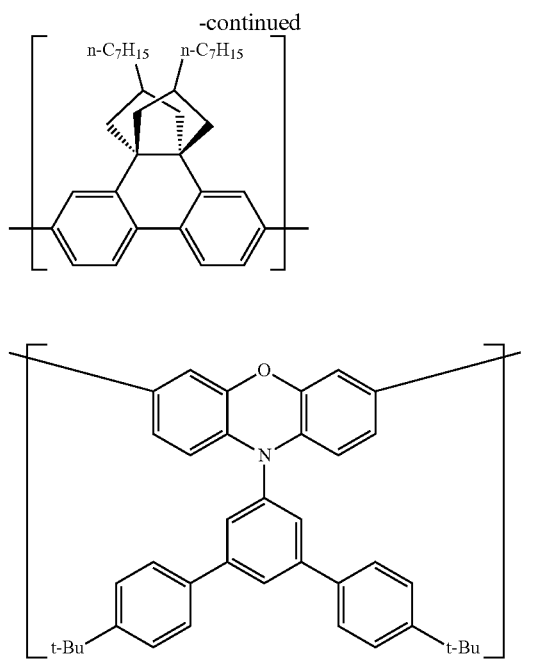
(P41)
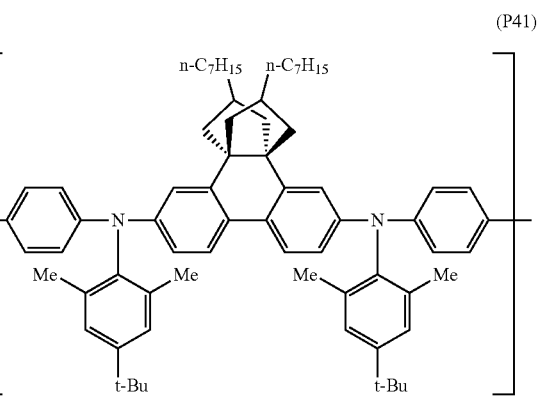
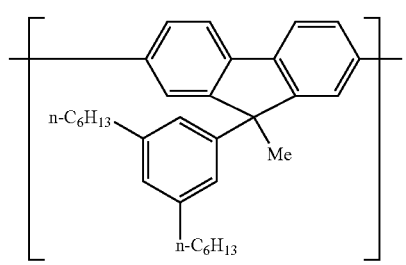
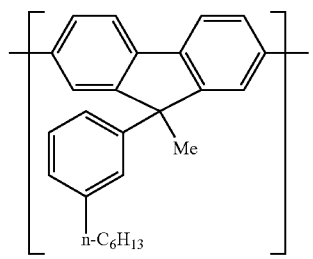

-continued
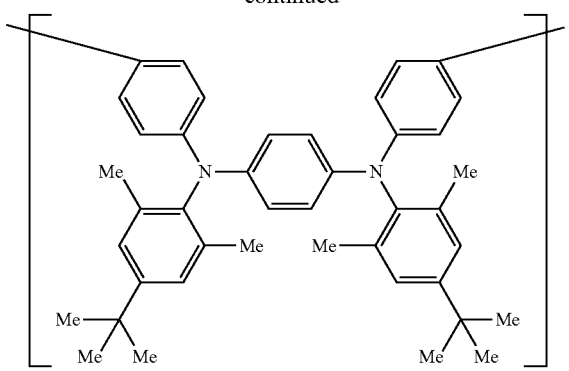
(P42)
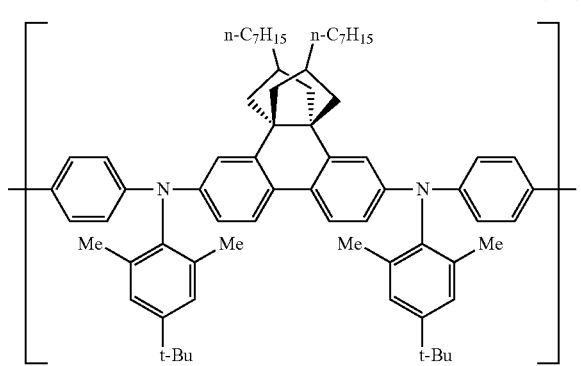
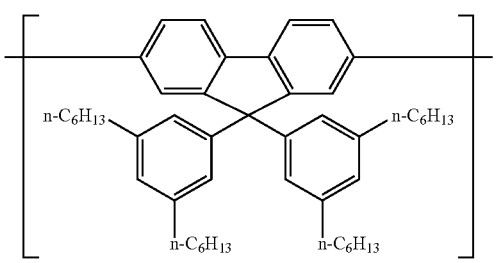
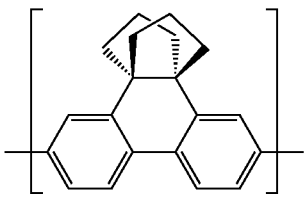
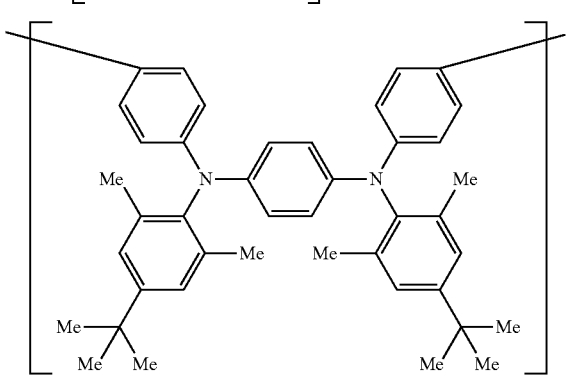
-continued
[Chemical Formula 46]
(P43)
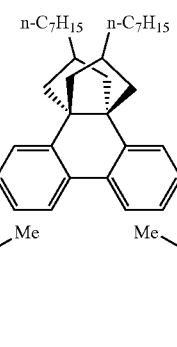
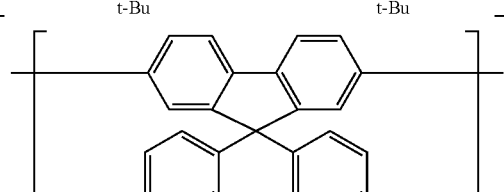
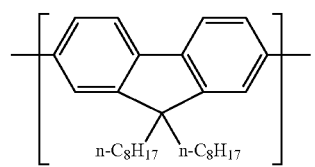
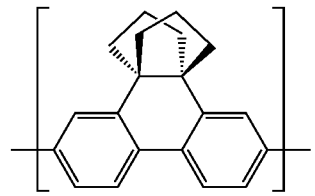
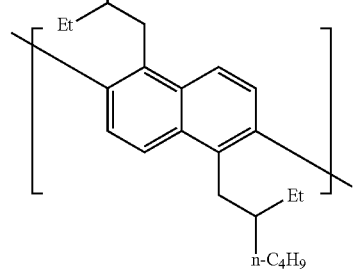
(P44)
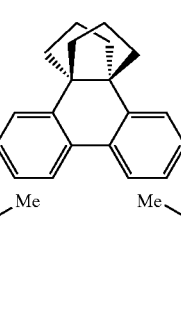

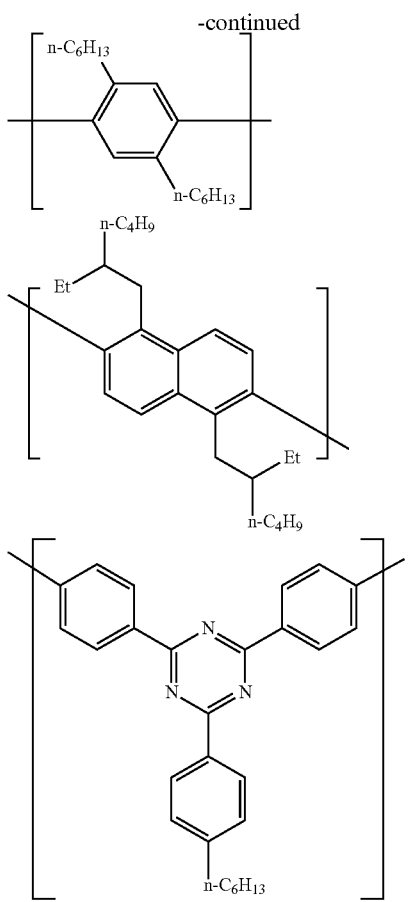

The polymer compound is synthesized by condensation polymerization of a monomer (1) that introduces the constitutional unit represented by the formula (1) with a monomer (X) that introduces a constitutional unit different from the constitutional unit, and when the number of the monomer (1) is $N_1$ and the number of the monomer (X) is $N_X$, it is preferable that $N_1$ and $N_X$ satisfy the following formula (I), and it is more preferable that $N_1$ and $N_X$ satisfy the following formula (II):

$$0.1 \leq N_1 \times 100/(N_1+N_X) \leq 50 \quad (I)$$

$$0.1 \leq N_1 \times 100/(N_1+N_X) \leq 40 \quad (II)$$

Examples of the monomer (1) include the compound represented by the formula (1M) described later. Examples of the monomer (X) include the compound represented by the formula (2M) and the compound represented by the formula (4M) described later.

If a polymerizable group remains as it is in the terminal group, the polymer compound according to the present embodiment has a possibility of reducing the light emission properties and life of the light-emitting device produced using the polymer compound. For this reason, it is preferable that the terminal group be a stable group (such as an aryl group and a monovalent heterocyclic group (particularly, a monovalent aromatic heterocyclic group)).

The polymer compound according to the present embodiment, when it is a copolymer, may be any copolymer; for example, the polymer compound according to the present embodiment may be any of block copolymers, random copolymers, alternating copolymers, and graft copolymers.

The polymer compound according to the present embodiment is useful as light-emitting materials, charge transport materials, and the like, and may be used in combination with other compound as a composition described later.

The polystyrene-equivalent number-average molecular weight (Mn) of the polymer compound according to the present embodiment measured by gel permeation chromatography (hereinafter, referred to as "GPC") is usually $1 \times 10^3$ to $1 \times 10^8$, and preferably $1 \times 10^4$ to $5 \times 10^6$. The polystyrene-equivalent weight-average molecular weight (Mw) of the polymer compound according to the present embodiment is usually $1 \times 10^3$ to $1 \times 10^8$, and preferably $1 \times 10^4$ to $1 \times 10^7$ because film forming properties are good and the luminance life of the light-emitting device to be obtained using the polymer compound is more excellent.

It is preferable that the glass transition temperature of the polymer compound according to the present embodiment be 70° C. or more because durability against various processes for producing the light-emitting device is high and the heat resistance of the light-emitting device is good.

The light-emitting device using the polymer compound is a high performance light-emitting device that can be derived with excellent luminance life. Accordingly, the light-emitting device is useful for backlights of liquid crystal displays, curved or flat light sources for lighting, segment display devices, dot matrix display devices, and the like. Further, the polymer compound according to the present embodiment can also be used as a dye for a laser, a material for an organic solar cell, an organic semiconductor for an organic transistor, a material for a conductive film such as conductive films and organic semiconductor films, and a light-emittable film material that emits fluorescence or phosphorescence.

(Method for Producing Polymer Compound)

In the case where the polymer compound is a copolymer, the polymer compound can be produced, for example, by condensation polymerizing the compound represented by the following formula (1M) (hereinafter, referred to as a "compound 1M" depending on cases) with other monomer (such as the compound represented by the following formula (2M) (hereinafter, referred to as a "compound 2M" depending on cases) and/or the compound represented by the following formula (4M) (hereinafter, referred to as a "compound 4M" depending on cases)).

In the case where the polymer compound is a homopolymer, the polymer compound can be produced, for example, by condensation polymerizing the compound 1M.

Herein, the compound 1M, the compound 2M, and a compound 4M are collectively referred to as the "monomer" in some cases.

[Chemical Formula 47]

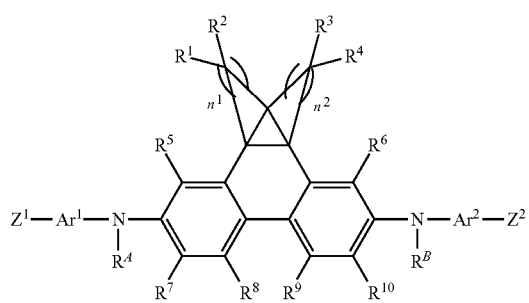

(1M)

[Chemical Formula 48]

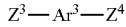
(2M)

[Chemical Formula 49]

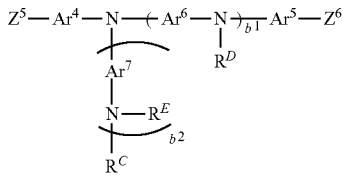
(4M)

In the formula (1M), $n^1$, $n^2$, $R^1$, $R^2$, $R^3$, $R^4$, $R^5$, $R^6$, $R^7$, $R^8$, $R^9$, $R^{10}$, $Ar^1$, $Ar^2$, $R^A$, and $R^B$ are the same as above; $Z^1$ and $Z^2$ each independently represent a group selected from the following substituent groups (the following substituent group A or the following substituent group B).

In the formula (2M), $Ar^3$ is the same as above; $Z^3$ and $Z^4$ represent a group selected from the following substituent group A or the following substituent group B.

In the formula (4M), $b^1$, $b^2$, $Ar^4$, $Ar^5$, $Ar^6$, $Ar^7$, $R^C$, $R^D$, and $R^E$ are the same as above; $Z^5$ and $Z^6$ represent a group selected from the following substituent group A or the substituent group B.

<Substituent Group A>

Groups represented by a chlorine atom, a bromine atom, an iodine atom, and —O—S(=O)$_2$R$^{41}$ (R$^{41}$ represents an alkyl group, or an aryl group which may be substituted by alkyl group, alkoxy group, nitro group, fluorine atom, or a cyano group).

<Substituent Group B>

Groups represented by —B(OR$^{42}$)$_2$ (R$^{42}$ represents a hydrogen atom or an alkyl group; and a plurality of R$^{42}$ present may be the same or different from each other and may be linked to each other to form a cyclic structure); groups represented by —BF$_4$Q$^1$ (Q$^1$ represents a monovalent cation selected from the group consisting of Li$^+$, Na$^+$, K$^+$, Rb$^+$, and Cs$^+$); groups represented by —MgY$^1$ (Y$^1$ represents a chlorine atom, a bromine atom, or an iodine atom); groups represented by —ZnY$^2$ (Y$^2$ represents a chlorine atom, a bromine atom, or an iodine atom); and groups represented by —Sn(R$^{43}$)$_3$ (R$^{43}$ represents a hydrogen atom or an alkyl group; and a plurality of R$^{43}$ present may be the same or different from each other and may be linked to each other to form a cyclic structure).

It is known that the compound having the group selected from the substituent group A and the compound having the group selected from the substituent group B are condensation polymerized by a known coupling reaction, and carbon atoms bonded to the groups are bonded. For this reason, if the compound A having two groups selected from the substituent group A and the compound B having two groups selected from the substituent group B are fed to the known coupling reaction, a condensation polymer of the compound A and the compound B can be obtained by condensation polymerization.

For example, in the case where $Z^1$ and $Z^2$ in the compound 1M are a group selected from the substituent group A, a group selected from the substituent group B can be selected as $Z^3$ and $Z^4$ (or $Z^5$ and $Z^6$) in the compound 2M (or the compound 4M). In the case where $Z^1$ and $Z^2$ in the compound 1M are a group selected from the substituent group B, a group selected from the substituent group A can be selected as $Z^3$ and $Z^4$ (or $Z^5$ and $Z^6$) in the compound 2M (or the compound 4M).

A condensation polymer can also be obtained, for example, by a method for polymerizing the compound having two groups selected from the substituent group A with an Ni(0) catalyst (Yamamoto polymerization) (Progress in Polymer Science, Vol. 17, pp. 1153 to 1205, 1992).

In such condensation polymerization, the first constitutional unit is introduced by the compound 1M, the second constitutional unit is introduced by the compound 2M, and the third constitutional unit is introduced by the compound 4M.

Examples of the condensation polymerization method include a method for polymerization using the Suzuki coupling reaction (Chem. Rev.), Vol. 95, pp. 2457-2483 (1995)), a method for polymerization using the Grignard reaction (Bull. Chem. Soc. Jpn., Vol. 51, p. 2091 (1978)), a method for polymerization using an Ni(0) catalyst (Progress in Polymer Science, Vol. 17, pp. 1153 to 1205, 1992), and a method using the Stille coupling reaction (European Polymer Journal), Vol. 41, pp. 2923-2933 (2005)). Among these, from the viewpoint of easy synthesis of raw materials and simple operation of the polymerization reaction, the method for polymerization using the Suzuki coupling reaction and the method for polymerization using an Ni(0) catalyst are preferable; considering easy control of the structure of the polymer compound, a method for polymerization using an aryl-aryl cross coupling reaction such as the Suzuki coupling reaction, the Grignard reaction, and the Stille coupling reaction is more preferable; the reaction using the polymerization by the Suzuki coupling reaction is particularly preferable.

Examples of the condensation polymerization method include a method of reacting the compounds above with a proper catalyst or base when necessary. In the case where the method for polymerization using the Suzuki coupling reaction is selected, in order to obtain the polymer compound having a desired molecular weight, the ratio of the total mole number of the group selected from substituent group B that each compound has to the total mole number of the group selected from the substituent group A that each compound has may be adjusted. Usually, it is preferable that the ratio of the latter mole number to the former mole number be 0.95 to 1.05, it is more preferable that the ratio of the latter mole number to the former mole number be 0.98 to 1.02, and it is still more preferable that the ratio of the latter mole number to the former mole number be 0.99 to 1.01.

It is preferable that the amount of the compound 1M to be used in the condensation polymerization be 0.1 to 70 mol % based on the total molar amount of the compound 1M and other monomer, it is more preferable that the amount of the compound 1M to be used in the condensation polymerization be 0.1 to 50 mol % based on the total molar amount of the compound 1M and other monomer, and it is still more preferable that the amount of the compound 1M to be used in the condensation polymerization be 0.1 to 40 mol % based on the total molar amount of the compound 1M and other monomer. In the case where the compound 2M is used in the condensation polymerization, it is preferable that the amount of the compound 2M to be used be 0.1 to 99.9 mol % based on the total molar amount of the compound 2M and the other monomer, it is more preferable that the amount of the compound 2M to be used be 30 to 99.9 mol % based on the total molar amount of the compound 2M and the other monomer, and it is still more preferable that the amount of the compound 2M to be used be 50 to 99.9 mol % based on the total molar amount of the compound 2M and the other monomer. In the case where the compound 4M is used in the condensation polymerization, it is preferable that the amount of the compound 4M be 0.1 to 70 mol % based on the total molar amount of the compound 4M and the other monomer, it is more preferable that the amount of the compound 4M be 0.1 to 50 mol % based on the total molar amount of the compound 4M and the other monomer, and it is still more preferable that the amount of the compound 4M be 0.1 to 40 mol % based on the total molar amount of the compound 4M and the other monomer. According to such condensation polymerization, a polymer compound that satisfies the above formula (I) can be obtained.

The monomer synthesized in advance and separated may be used, or the monomer may be synthesized during the reaction system and used as it is. In the case where the polymer compound to be obtained is used for the light-emitting device, the purity may affect the performance of the light-emitting device. For this reason, it is preferable that these monomers be refined by a method such as distillation, chromatography, sublimation refining, recrystallization or a combination thereof.

In the method of producing the polymer compound according to the present embodiment, it is preferable that the monomers be polymerized in the presence of a catalyst. In the case where polymerization is performed using the Suzuki coupling reaction, examples of the catalyst include transition metal complexes such as palladium complexes such as palladium[tetrakis(triphenylphosphine)], [tris(dibenzylideneacetone)]dipalladium, palladium acetate, and dichlorobistriphenylphosphinepalladium; and complexes in which a ligand such as triphenylphosphine, tri-tert-butylphosphine, and tricyclohexylphosphine is coordinated with these transition metal complexes.

In the case where the polymerization is performed using the Ni(0) catalyst, examples of the Ni(0) catalyst include transition metal complexes such as nickel complexes such as nickel[tetrakis(triphenylphosphine)], [1,3-bis(diphenylphosphino)propane]dichloronickel, [bis(1,4-cyclooctadiene)]nickel; and complexes in which a ligand such as triphenylphosphine, tri-tert-butylphosphine, tricyclohexylphosphine, diphenylphosphinopropane, a substituted or unsubstituted bupyridyl, and a substituted or unsubstituted phenanthroline is coordinated with these transition metal complexes.

The catalyst synthesized in advance may be used, or the catalyst prepared during the reaction system may be used as it is. These catalysts may be used alone or in combination.

The amount of the catalyst may be an effective amount as the catalyst; for example, the amount in terms of the mole number of the transition metal is usually 0.0001 to 300 mol %, preferably 0.001 to 50 mol %, and more preferably 0.01 to 20 mol % based on 100 mol % of the total of all the monomers in the polymerization reaction.

In the method for polymerization using the Suzuki coupling reaction, it is preferable that a base be used. Examples of the base include inorganic salt groups such as sodium carbonate, potassium carbonate, cesium carbonate, potassium fluoride, cesium fluoride, and tripotassium phosphate; and organic bases such as tetrabutylammonium fluoride, tetrabutylammonium chloride, tetrabutylammonium bromide, tetraethylammonium hydroxide, and tetrabutylammonium hydroxide.

The amount of the base is usually 50 to 2000 mol %, and preferably 100 to 1000 mol % based on 100 mol % of the total of all the monomers in the polymerization reaction.

The polymerization reaction may be performed in the absence of a solvent, or performed in the presence of a solvent; usually, the polymerization reaction is performed in the presence of an organic solvent. Here, examples of the organic solvent include toluene, xylene, mesitylene, tetrahydrofuran, 1,4-dioxane, dimethoxyethane, N,N-dimethylacetoamide, and N,N-dimethylformamide. Usually, in order to suppress a side reaction, it is desired that a solvent subjected to a deoxidation treatment be used. The organic solvents may be used alone or in combination.

It is preferable that the amount of the organic solvent to be used be an amount such that the total concentration of all the monomers in the polymerization reaction is 0.1 to 90% by weight, it is more preferable that the amount of the organic solvent to be used be an amount such that the total concentration of all the monomers in the polymerization reaction is 1 to 50% by weight, and it is still more preferable that the amount of the organic solvent to be used be an amount such that the total concentration of all the monomers in the polymerization reaction is 2 to 30% by weight.

The reaction temperature of the polymerization reaction is preferably −100 to 200° C., more preferably −80 to 150° C., and still more preferably 0 to 120° C. The reaction time is usually 1 hour or more, and preferably 2 to 500 hours.

In the polymerization reaction, to avoid remaining of the polymerizable group (such as $Z^1$, $Z^2$) at the terminal in the polymer compound according to the present embodiment, a compound represented by the following formula (1T) may be used as a chain-terminating agent. Thereby, a polymer compound whose terminal is the aryl group or monovalent heterocyclic group (particularly, the monovalent aromatic heterocyclic group) can be obtained.

$$Z^T\text{—}Ar^T \qquad (1T)$$

wherein $Ar^T$ represents an aryl group that may have a substituent or a monovalent heterocyclic group (particularly, a monovalent aromatic heterocyclic group) that may have a substituent; $Z^T$ represents the group selected from the substituent group A and the substituent group B above. Examples of the aryl group and the monovalent heterocyclic group (particularly, the monovalent aromatic heterocyclic group) in $Ar^T$ can include the aryl groups and monovalent heterocyclic groups (particularly, the monovalent aromatic heterocyclic groups) exemplified as $R^1$ above.

A post-treatment in the polymerization reaction can be performed by a known method; for example, a method of removing water-soluble impurities by separation of a solution, a method in which a precipitate obtained by adding the reaction solution after the polymerization reaction to a lower alcohol such as methanol is filtered and dried, and the like can be used alone or in combination.

In the case where the purity of the polymer compound according to the present embodiment is low, refining may be performed by the standard method such as recrystallization, reprecipitation, continuous extraction with a Soxhlet extractor, and column chromatography; in the case where the polymer compound according to the present embodiment is used for the light-emitting device, the purity may affect the performance of the light-emitting device such as light emission properties; for this reason, it is preferable that after the condensation polymerization, a purifying treatment such as reprecipitation refining and separation by chromatography be performed.

(Compound)

The compound according to the present embodiment is a compound represented by the following formula (1M):

[Chemical Formula 50]

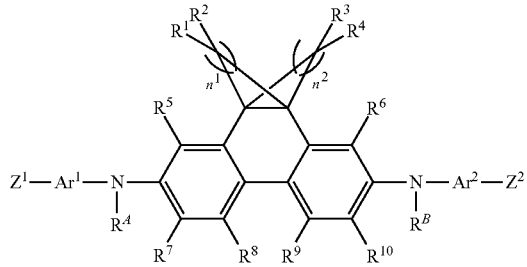

(1M)

wherein $n^1$, $n^2$, $R^2$, $R^3$, $R^4$, $R^5$, $R^6$, $R^7$, $R^8$, $R^9$, $R^{10}$, $Ar^1$, $Ar^2$, $R^A$, and $R^B$ are the same as above; $Z^1$ and $Z^2$ each independently represent a group selected from the substituent group (the substituent group A or substituent group B above).

For example, in the case where $n^1$ and/or $n^2$ is 2 or more in the formula (1M) and has a substituent, $R^1$ and $R^2$ are different from each other, and $R^3$ and $R^4$ are different from each other, a stereoisomer (diastereoisomer/enantiomer) can exist in the compound according to the present embodiment. The compound according to the present embodiment may be composed of only a single stereoisomer, or may be a mixture of different stereoisomers.

Hereinafter, a method of producing the compound represented by the formula (1M) will be described using an example in which $n^1$ and $n^2$ are 3. The compound represented by the formula (1M) can be produced by the methods according to the following Schemes 1 to 5.

[Scheme 1]

[Chemical Formula 51]

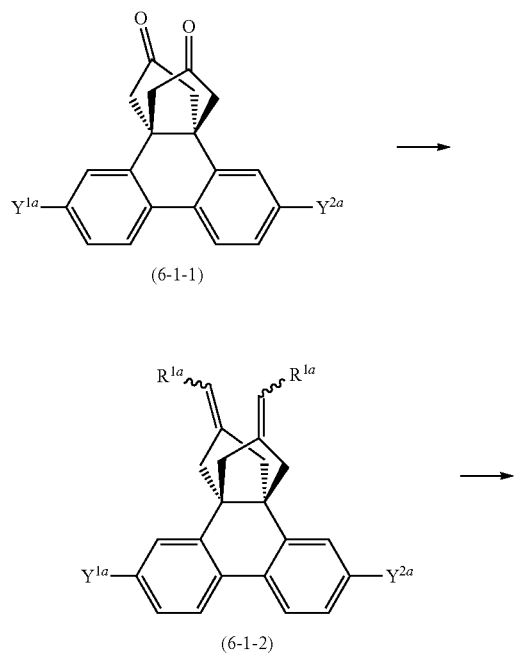

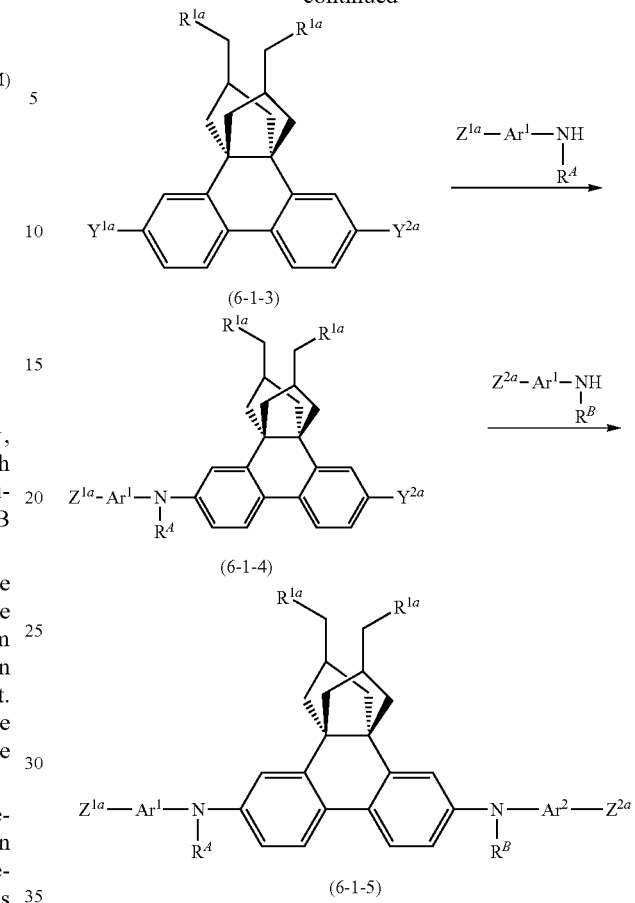

wherein the wavy line indicates that the compound having the wavy line is a geometric isomer mixture.

In Scheme 1, $Y^{1a}$ and $Y^{2a}$ each independently represent a hydrogen atom or a group selected from the substituent group A; $Z^{1a}$ and $Z^{2a}$ represent a hydrogen atom or a group selected from the substituent group A; $R^{1a}$ represents an unsubstituted or substituted alkyl group, an unsubstituted or substituted aryl group, or an unsubstituted or substituted monovalent heterocyclic group; $Ar^1$, $Ar^2$, $R^A$, and $R^B$ are the same as above; and a plurality of $R^{1a}$ present may be the same or different from each other.

In Scheme 1, first, by feeding the compound represented by the formula (6-1-1) (hereinafter, referred to as a "compound (6-1-1)." Hereinafter, the same is true of the compound represented by the formula (6-1-2)) to the Wittig reaction, the Horner-Wadsworth-Emmons reaction, or the like, a compound (6-1-2) is obtained. Next, by feeding the compound (6-1-2) to the reduction reaction, a compound (6-1-3) is obtained.

Here, in the case where $Y^{1a}$ and $Y^{2a}$ are a hydrogen atom, the compound (6-1-3) is fed to a reaction such as a bromination reaction, and $Y^{1a}$ and $Y^{2a}$ are converted into the group selected from the substituent group A.

Next, by a coupling reaction of the compound (6-1-3) with a predetermined amine compound, the compound (6-1-5) is obtained via the compound (6-1-4). In the case where the $Z^{1a}$ and $Z^{1b}$ in the compound (6-1-5) are a hydrogen atom, by feeding the compound (6-1-5) to a reaction such as a bromination reaction, the hydrogen atom can be converted to the group selected from the substituent group A. In the case where the $Z^{1a}$ and $Z^{1b}$ in the compound (6-1-5) are the group selected from the substituent group A, the group can be converted to the group selected from the substituent group B by a known reaction.

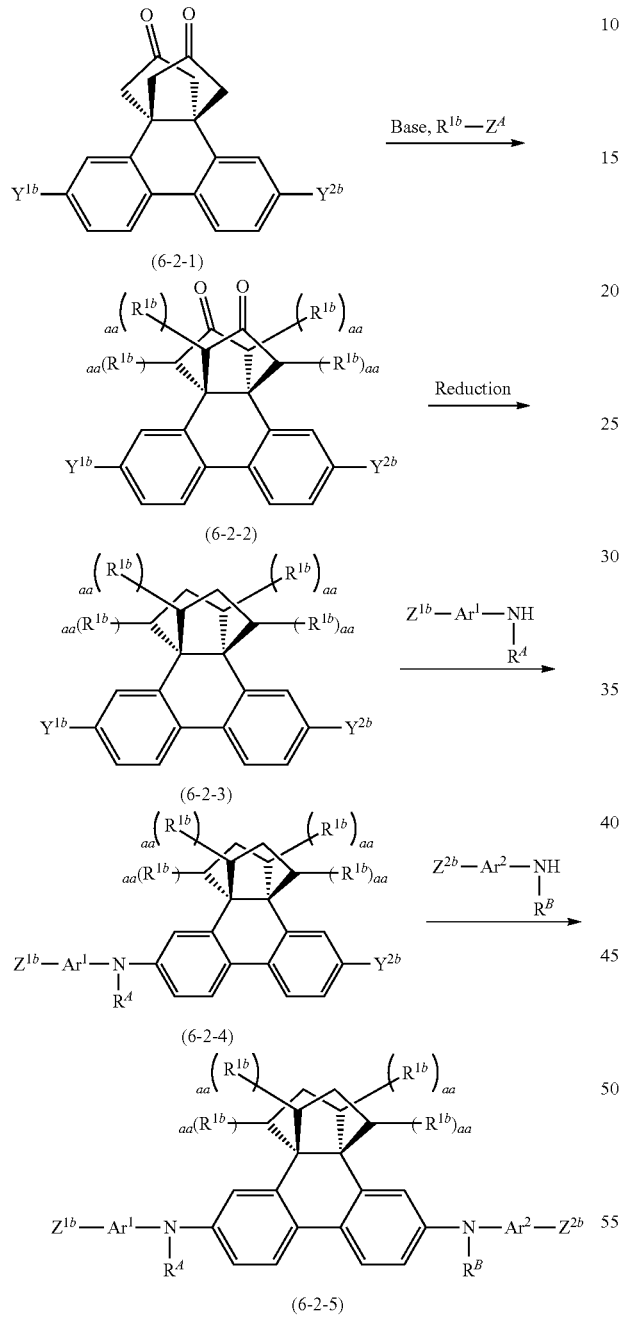

In Scheme 2, aa represents 0 or 1; $Y^{1b}$ and $Y^{2b}$ each independently represent a hydrogen atom or the group selected from the substituent group A; $Z^{1b}$ and $Z^{2b}$ each independently represent a hydrogen atom or the group selected from the substituent group A; $Z^A$ represents the group selected from the substituent group A; $R^{1b}$ represents an unsubstituted or substituted alkyl group, an unsubstituted or substituted aryl group, or an unsubstituted or substituted monovalent heterocyclic group. $Ar^1$, $Ar^2$, $R^A$, and $R^B$ are the same as above. A plurality of aa present may be the same or different from each other. In the case where a plurality of $R^{1b}$ are present, those may be the same or different.

In Scheme 2, first, in the presence of a base, a compound (6-2-2) is obtained by an addition reaction of the compound (6-2-1) and $R^{1b}$—$Z^A$. Next, by feeding the compound (6-2-2) to the reduction reaction, a compound (6-2-3) is obtained.

Here, in the case where $Y^{1b}$ and $Y^{2b}$ are a hydrogen atom, the compound (6-2-3) is fed to a reaction such as a bromination reaction, and $Y^{1b}$ and $Y^{2b}$ are converted into the group selected from the substituent group A.

Next, by a coupling reaction of the compound (6-2-3) with a predetermined amine compound, the compound (6-2-5) is obtained via the compound (6-2-4). In the case where $Z^{1b}$ and $Z^{2b}$ in the compound (6-2-5) are a hydrogen atom, by feeding the compound (6-2-5) to the reaction such as the bromination reaction, the hydrogen atom can be converted to the group selected from the substituent group A. In the case where $Z^{1b}$ and $Z^{2b}$ in the compound (6-2-5) are the group selected from the substituent group A, the group can be converted to the group selected from the substituent group B by a known reaction.

[Scheme 3]

[Chemical Formula 53]

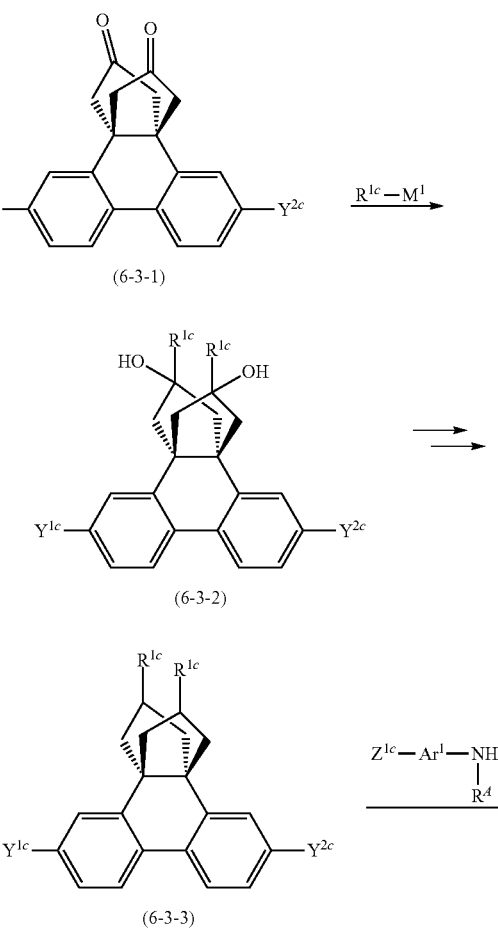

-continued

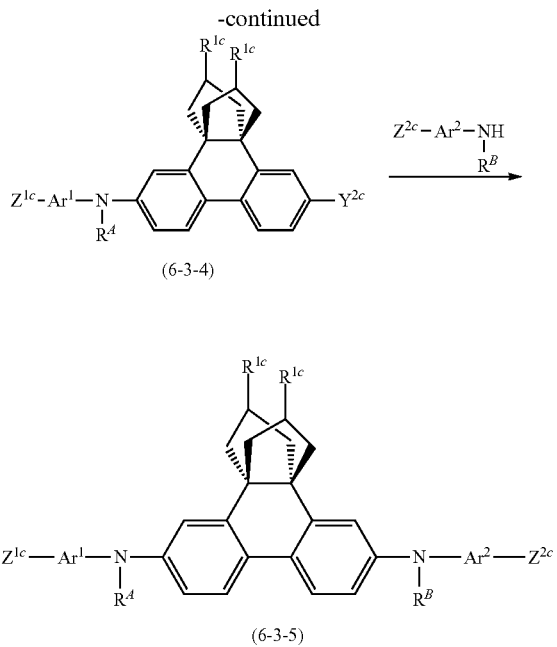

(6-3-4)

(6-3-5)

[Scheme 4]

[Chemical Formula 54]

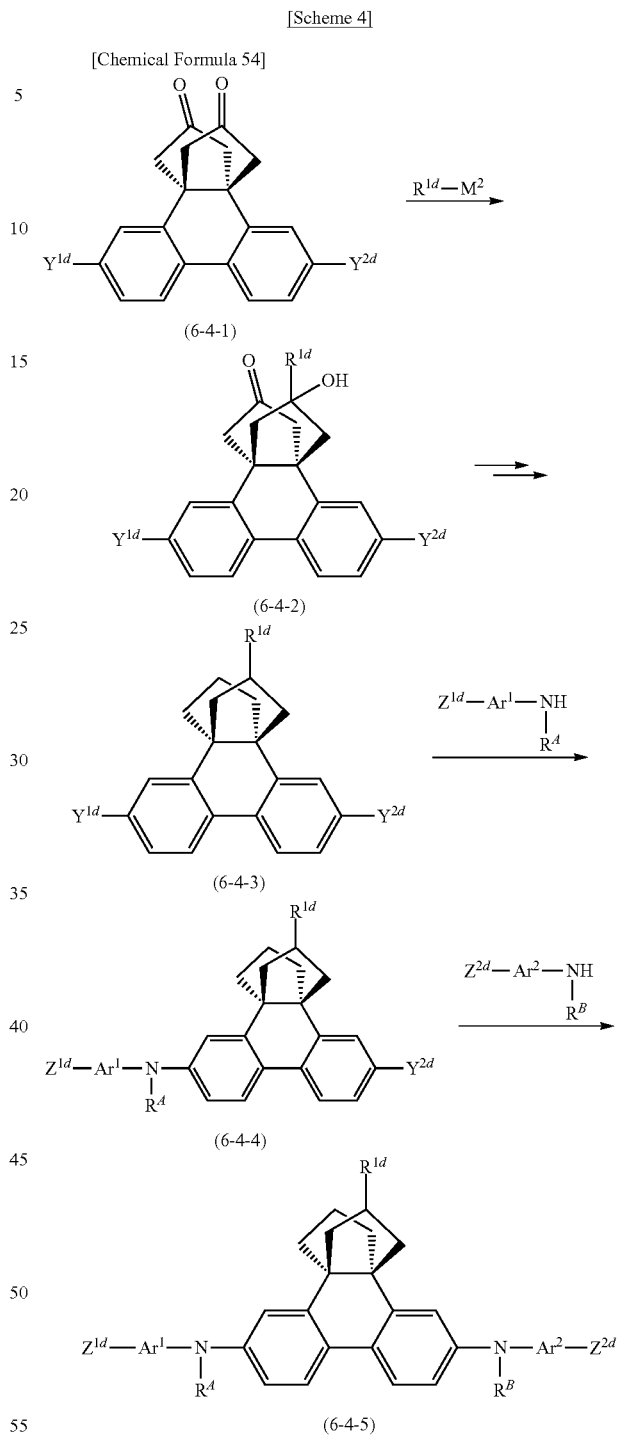

(6-4-1)

(6-4-2)

(6-4-3)

(6-4-4)

(6-4-5)

In Scheme 3, $Y^{1c}$ and $Y^{2c}$ each independently represent a hydrogen atom or a group selected from the substituent group A; $Z^{1c}$ and $Z^{2c}$ each independently represent a hydrogen atom or a group selected from the substituent group A; $R^{1c}$ represents an unsubstituted or substituted alkyl group, an unsubstituted or substituted aryl group, or an unsubstituted or substituted monovalent heterocyclic group; $M^1$ represents an alkali metal such as lithium and potassium or a group represented by $-M^H Z^H$, $Ar^1$, $Ar^2$, $R^A$, and $R^B$ are the same as above; $M^H$ represents Mg or Zn; $Z^H$ represents a halogen atom; and a plurality of $R^{1c}$ present may be the same or different from each other.

In Scheme 3, first, a compound (6-3-2) is obtained by a reaction of the compound (6-3-1) with $R^{1c}$-$M^1$. Next, a compound (6-3-3) is obtained by converting a hydroxyl group to a hydrogen atom in the compound (6-3-2) by a known reaction.

Here, in the case where $Y^{1c}$ and $Y^{2c}$ are a hydrogen atom, the compound (6-3-3) is fed to a reaction such as a bromination reaction, and $Y^{1c}$ and $Y^{2c}$ are converted into the group selected from the substituent group A.

Next, by a coupling reaction of the compound (6-3-3) with a predetermined amine compound, the compound (6-3-5) is obtained via the compound (6-3-4). In the case where $Z^{1c}$ and $Z^{2c}$ in the compound (6-3-5) are a hydrogen atom, by feeding the compound (6-3-5) to the reaction such as the bromination reaction, the hydrogen atom can be converted to the group selected from the substituent group A. In the case where $Z^{1c}$ and $Z^{2c}$ in the compound (6-3-5) are the group selected from the substituent group A, the group can be converted to the group selected from the substituent group B by a known reaction.

In Scheme 4, $Y^{1d}$ and $Y^{2d}$ each independently represent a hydrogen atom or a group selected from the substituent group A; $Z^{1d}$ and $Z^{2d}$ each independently represent a hydrogen atom or a group selected from the substituent group A; $R^{1d}$ represents an unsubstituted or substituted alkyl group, an unsubstituted or substituted aryl group, or an unsubstituted or substituted monovalent heterocyclic group; $M^2$ represents an alkali metal such as lithium and potassium or a group represented by $-M^H Z^H$; $M^H$ represents Mg or Zn; $Z^H$ represents a halogen atom.

In Scheme 4, first, a compound (6-4-2) is obtained by a reaction of the compound (6-4-1) with $R^{1d}$-$M^2$. Next, by feeding the compound (6-4-2) to the reduction reaction, a compound (6-4-3) is obtained.

Here, in the case where $Y^{1d}$ and $Y^{2d}$ are a hydrogen atom, the compound (6-4-3) is fed to a reaction such as a bromination reaction, and $Y^{1d}$ and $Y^{2d}$ are converted into the group selected from the substituent group A.

Next, by a coupling reaction of the compound (6-4-3) with a predetermined amine compound, the compound (6-4-5) is obtained via the compound (6-4-4). In the case where $Z^{1d}$ and $Z^{2d}$ in the compound (6-4-5) are a hydrogen atom, by feeding the compound (6-4-5) to the reaction such as the bromination reaction, the hydrogen atom can be converted to the group selected from the substituent group A. In the case where $Z^{1d}$ and $Z^{2d}$ in the compound (6-4-5) are the group selected from the substituent group A, the group can be converted to the group selected from the substituent group B by a known reaction.

[Scheme 5]

[Chemical Formula 55]

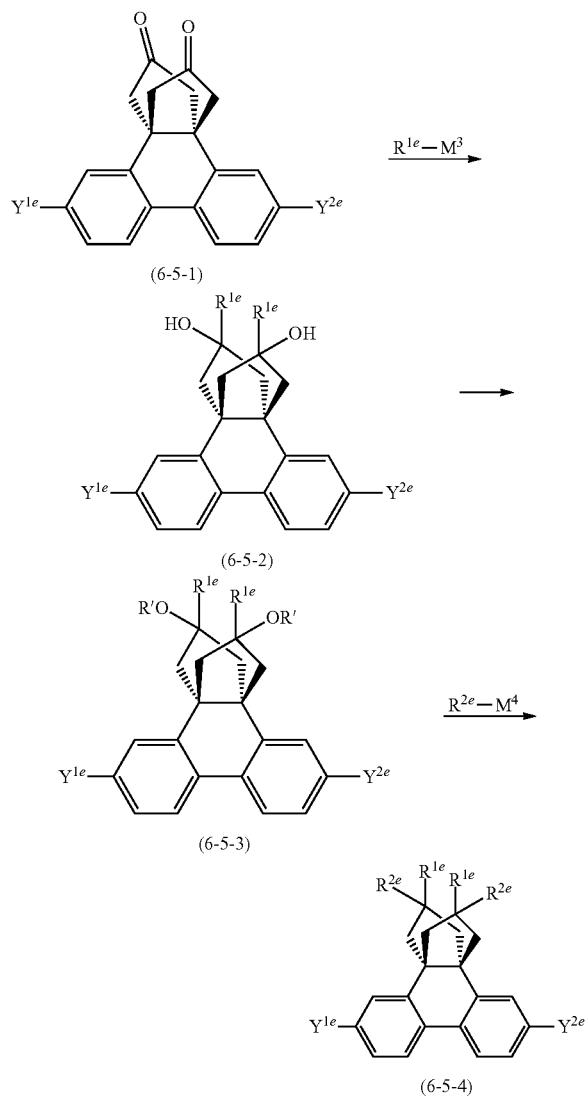

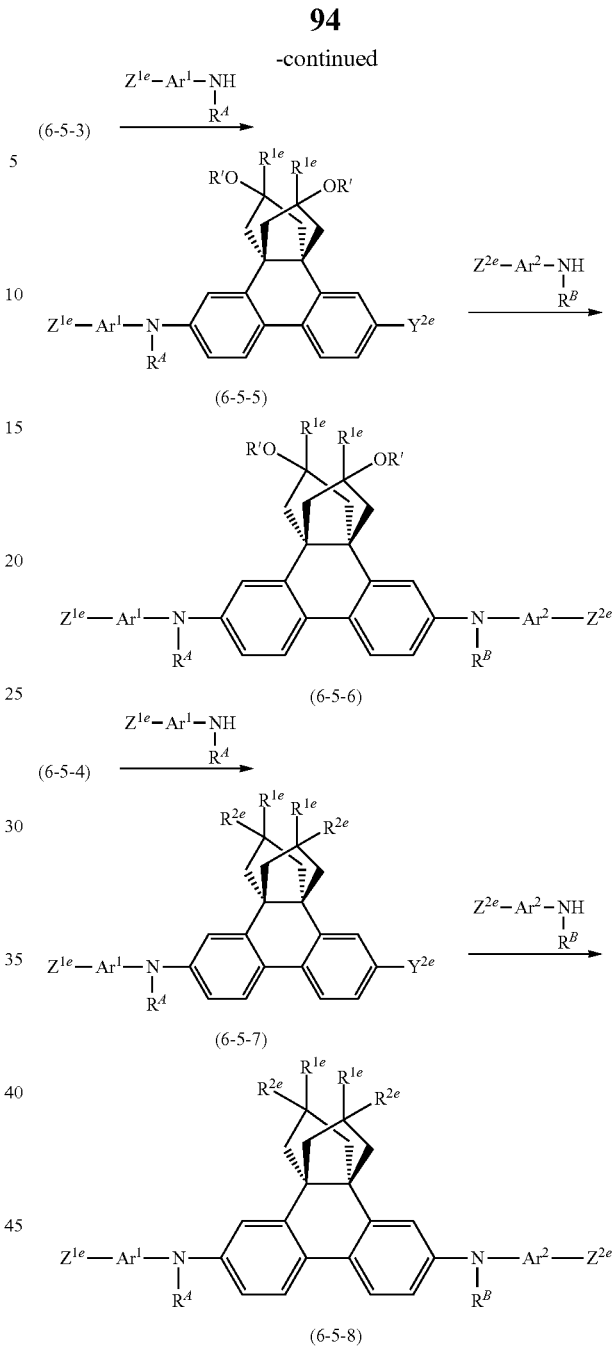

In Scheme 5, $Y^{1e}$ and $Y^{2e}$ each independently represent a hydrogen atom or the group selected from the substituent group A; $Z^{1e}$ and $Z^{2e}$ each independently represent a hydrogen atom or the group selected from the substituent group A; $R^{1e}$ and $R^{2e}$ each independently represent unsubstituted or substituted alkyl group, an unsubstituted or substituted aryl group or unsubstituted or substituted monovalent heterocyclic group; R' represents an unsubstituted or substituted alkyl group, an unsubstituted or substituted aryl group, or an unsubstituted or substituted monovalent heterocyclic group; $M^3$ and $M^4$ each independently represent alkali metal such as lithium and potassium or a group represented by -$M^H Z^H$; $M^H$ represents Mg or Zn; $Z^H$ represents a halogen atom. A plurality of $R^{1e}$ present may be the same or different, and a plurality of $R^{2e}$ present may be the same or different.

In Scheme 5, first, a compound (6-5-2) is obtained by a reaction of the compound (6-5-1) with $R^{1e}$-$M^3$. Next, by feeding the compound (6-5-2), to a reaction such as methanesulfonylation, a compound (6-5-3) having a leaving group is obtained. The compound (6-5-3) may be further reacted with $R^{2e}$-$M^4$; by the reaction, a compound (6-5-4) is obtained.

Here, in the case where $Y^{1e}$ and $Y^{2e}$ are a hydrogen atom, the compound (6-5-3) or the compound (6-5-4) is fed to a reaction such as a bromination reaction, and $Y^{1e}$ and $Y^{2e}$ are converted into the group selected from the substituent group A.

Next, by a coupling reaction of the compound (6-5-3) or the compound (6-5-4) with a predetermined amine compound, the compound (6-5-6) or the compound (6-5-8) is obtained. In the case where $Z^{1e}$ and $Z^{2e}$ in the compound (6-5-6) and the compound (6-5-8) are a hydrogen atom, by feeding the compound (6-5-6) and the compound (6-5-8) to the reaction such as the bromination reaction, the hydrogen atom can be converted to the group selected from the substituent group A. In the case where $Z^{1e}$ and $Z^{2e}$ in the compound (6-5-6) and the compound (6-5-8) are the group selected from the substituent group A, the group can be converted to the group selected from the substituent group B by a known reaction.

For example, compounds obtained by the methods described in J. Org. Chem. 2003, 68, 8715-8718 or the methods described in Journal of the Chemical Society, Perkin Transactions 1: Organic and Bio-Organic Chemistry (1997), (22), 3471-3478, or compounds obtained by feeding the compounds to the reaction such as the bromination reaction can be used as the compound (6-1-1), the compound (6-2-1), the compound (6-3-1), the compound (6-4-1), and the compound (6-5-1).

The compound having a stereoisomer can be synthesized by stereoselectively performing a hydrogenation reaction (hydrogenating reaction) in Scheme 1 above as the method for obtaining a specific stereoisomer. The specific stereoisomer can also be condensed and refined by preferential crystallization. Besides, after a stereoisomer mixture is synthesized, the specific stereoisomer can be separated and refined by chromatography.

(Composition)

The composition according to the present embodiment contains at least one selected from the group consisting of the polymer compound, a hole transport material, an electron transport material, and a light-emitting material. The composition can be suitably used in production of the light-emitting device, in the light-emitting device to be obtained, the luminance life is excellent.

Examples of the hole transport material include polyvinylcarbazole and derivatives thereof, polysilane and derivatives thereof, polysiloxane derivatives having an aromatic amine in the side chain or the main chain, pyrazoline derivatives, arylamine derivatives, stilbene derivatives, polyaniline and derivatives thereof, polythiophene and derivatives thereof, polypyrrole and derivatives thereof, poly(p-phenylenevinylene) and derivatives thereof, and poly(2,5-thienylenevinylene) and derivatives thereof. Besides, examples thereof include the hole transport materials described in Japanese Patent Application Laid-Open Nos. 63-70257, 63-175860, 2-135359, 2-135361, 2-209988, 3-37992, and 3-152184.

The content of the hole transport material is preferably 1 to 500 part by weight, more preferably 5 to 200 part by weight based on 100 part by weight of the polymer compound in the composition.

Examples of the electron transport material include oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, metal complexes of 8-hydroxyquinoline and derivatives thereof, polyquinoline and derivatives thereof, polyquinoxaline and derivatives thereof, polyfluorene and derivatives thereof, anthracene and derivatives thereof, and copolymers of anthracene and fluorene. Besides, examples thereof include the electron transport materials described in Japanese Patent Application Laid-Open Nos. 63-70257, 63-175860, 2-135359, 2-135361, 2-209988, 3-37992, and 3-152184.

The content of the electron transport material is preferably 1 to 500 part by weight, more preferably 5 to 200 part by weight based on 100 part by weight of the polymer compound in the composition.

Examples of the light-emitting material include low molecular fluorescence light-emitting materials and phosphorescence light-emitting materials. Examples of the light-emitting material include naphthalene derivatives; anthracene and derivatives thereof; copolymers of anthracene and fluorene; perylene and derivatives thereof; dyes such as polymethine dyes, xanthene dyes, coumarin dyes, and cyanine dyes; metal complexes having 8-hydroxyquinoline as a ligand; metal complexes having 8-hydroxyquinoline derivatives as a ligand; other fluorescent metal complexes; aromatic amines; tetraphenylcyclopentadiene and derivatives thereof; tetraphenylbutadiene and derivatives thereof; low molecular compound fluorescent materials such as stilbene low molecular compounds, silicon-containing aromatic low molecular compounds, oxazole low molecular compounds, furoxan low molecular compounds, thiazole low molecular compounds, tetraarylmethane low molecular compounds, thiadiazole low molecular compounds, pyrazole low molecular compounds, metacyclophane low molecular compounds, and acetylene low molecular compounds; metal complexes such as iridium complexes and platinum complexes; and triplet light emitting complexes. Besides, examples thereof include the light-emitting materials described in Japanese Patent Application Laid-Open Nos. 57-51781, 59-194393, and others.

Examples of the triplet light-emitting complex include iridium complexes in which iridium is the central metal, such as $Ir(ppy)_3$, $Btp_2Ir(acac)$, FIrpic, COM-1, COM-2, COM-3, COM-4, COM-5, COM-6, COM-7, COM-8, and ADS066GE available from American Dye Source, Inc.; platinum complexes in which platinum is the central metal, such as PtOEP; and europium complexes in which europium is the central metal, such as $Eu(TTA)_3phen$. These triplet light-emitting complexes are represented by the following formulas:

[Chemical Formula 56]
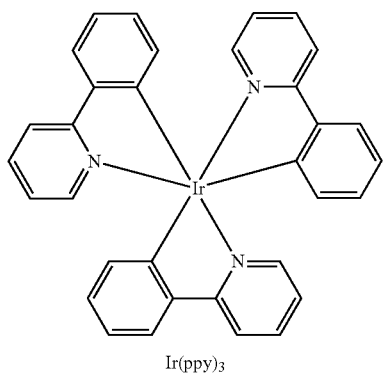
Ir(ppy)₃
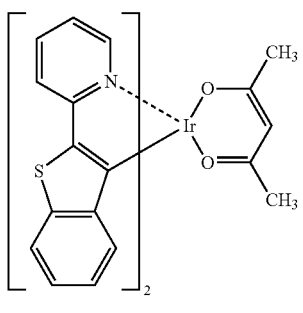
Btp₂Ir(acac)
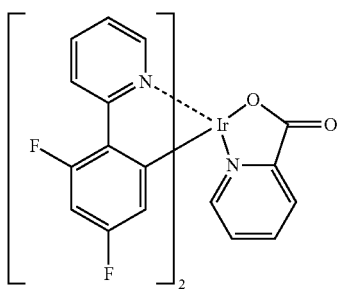
FIrpic
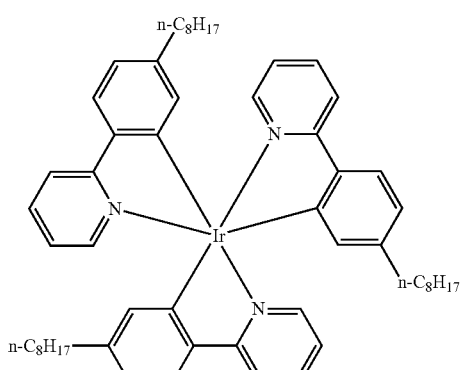
COM-1
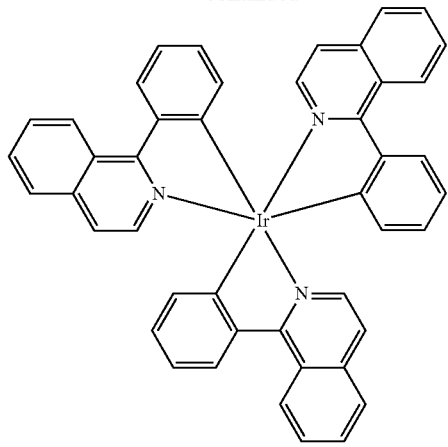
COM-2
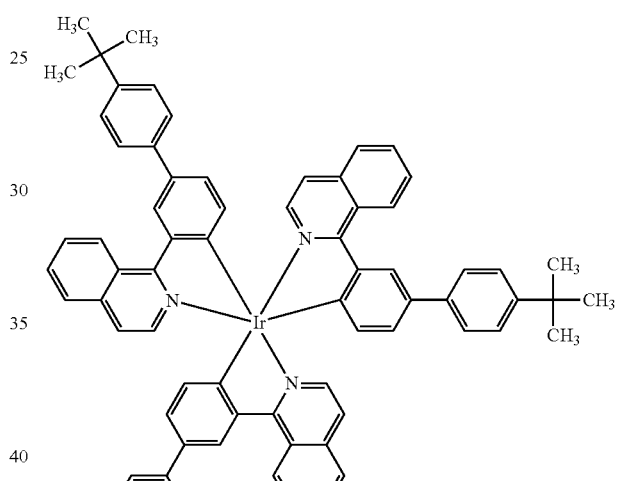
COM-3
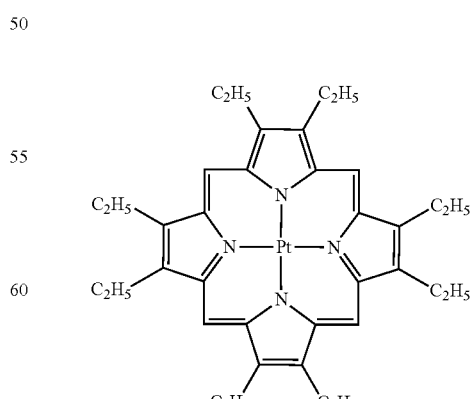
PtOEP

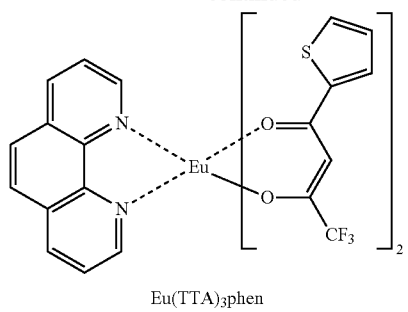

Eu(TTA)₃phen

[Chemical Formula 57]

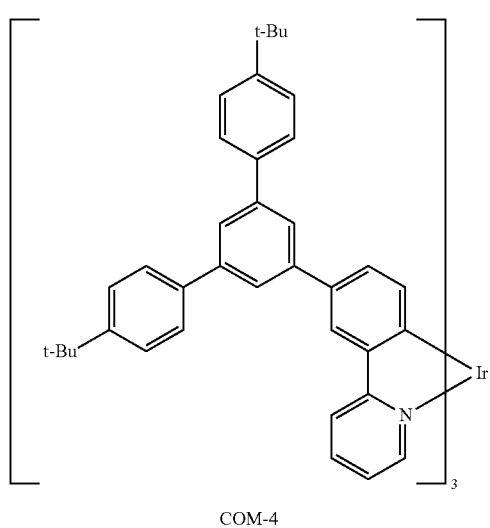

COM-4

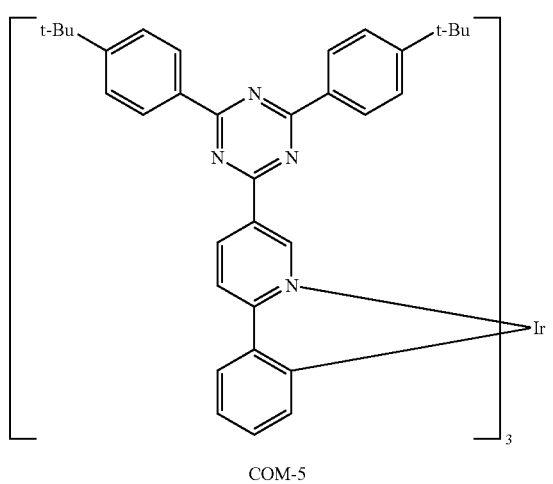

COM-5

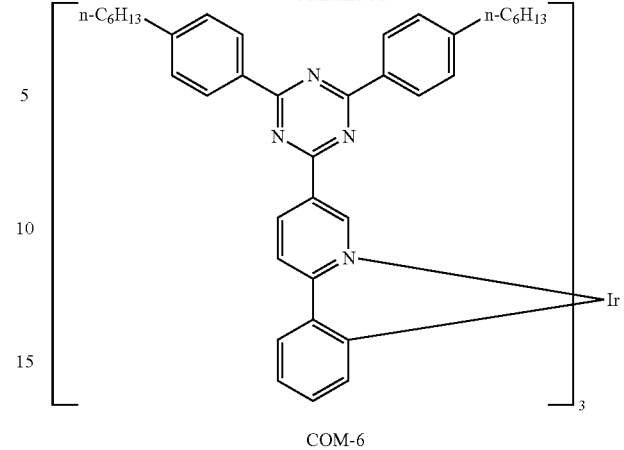

COM-6

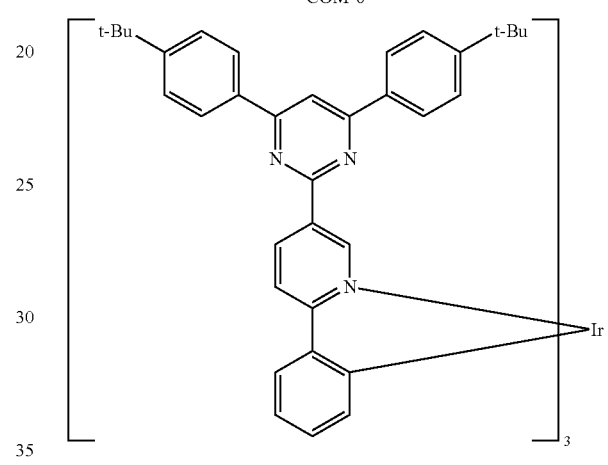

COM-7

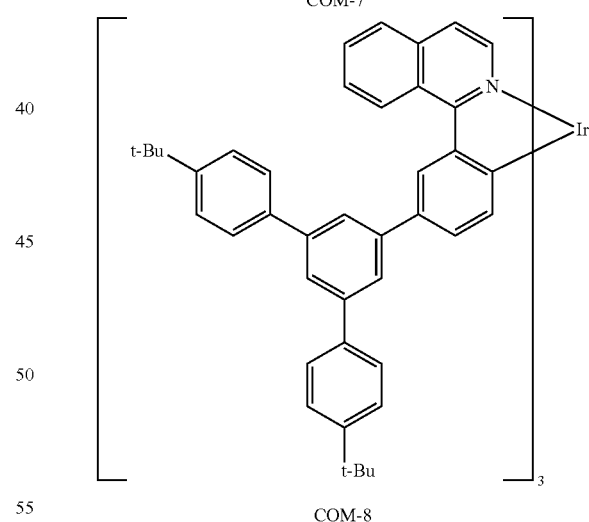

COM-8

The content of the light-emitting material is preferably 1 to 500 part by weight, more preferably 5 to 200 part by weight based on 100 part by weight of the polymer compound in the composition.

(Liquid Composition)

The polymer compound according to the present embodiment may be dissolved or dispersed in a solvent, preferably in an organic solvent to prepare a liquid composition (solution or dispersion liquid). Such a liquid composition is also referred to as an ink or a varnish. In the case where the liquid composition is used to form an organic film used in the light-emitting device, it is preferable that the liquid composition be a solution.

In addition to the polymer compound according to the present embodiment, the liquid composition may contain at least one selected from the group consisting of the hole transport material, the electron transport material, and the light-emitting material (namely, one embodiment of the composition above). Moreover, other substance may be added to the liquid composition unless the effects of the present invention are prevented. Examples of the other substance include an antioxidant, a viscosity control agent, and a surfactant.

Here, the organic solvent is not particularly limited as long as the polymer compound according to the present embodiment is dissolved or dispersed; examples of the organic solvent include the following organic solvents (hereinafter, referred to as a "solvent groups" in some cases).

Aromatic hydrocarbon solvents: such as toluene, xylene (isomers or a mixture thereof), 1,2,3-trimethylbenzene, 1,2,4-trimethylbenzene, mesitylene (1,3,5-trimethylbenzene), ethylbenzene, propylbenzene, isopropylbenzene, butylbenzene, isobutylbenzene, 2-phenylbutane, tert-butylbenzene, pentylbenzene, neopentylbenzene, isoamylbenzene, hexylbenzene, cyclohexylbenzene, heptylbenzene, octylbenzene, 3-propyltoluene, 4-propyltoluene, 1-methyl-4-propylbenzene, 1,4-diethylbenzene, 1,4-dipropylbenzene, 1,4-di-tert-butylbenzene, indane, and tetralin (1,2,3,4-tetrahydronaphthalene).

Aliphatic hydrocarbon solvents: such as n-pentane, n-hexane, cyclohexane, methylcyclohexane, n-heptane, n-octane, n-nonane, n-decane, and decalin.

Aromatic ether solvents: such as anisole, ethoxybenzene, propoxybenzene, butyloxybenzene, pentyloxybenzene, cyclopentyloxybenzene, hexyloxybenzene, cyclohexyloxybenzene, heptyloxybenzene, octyloxybenzene, 2-methylanisole, 3-methylanisole, 4-methylanisole, 4-ethylanisole, 4-propylanisole, 4-butylanisole, 4-pentylanisole, 4-hexylanisole, diphenylether, 4-methylphenoxybenzene, 4-ethylphenoxybenzene, 4-propylphenoxybenzene, 4-butylphenoxybenzene, 4-pentylphenoxybenzene, 4-hexylphenoxybenzene, 4-phenoxytoluene, 3-phenoxytoluene, 1,3-dimethoxybenzene, 2,6-dimethylanisole, 2,5-dimethylanisole, 2,3-dimethylanisole, and 3,5-dimethylanisole.

Aliphatic ether solvents: such as tetrahydrofuran, dioxane, and dioxolane.

Ketone solvents: such as acetone, methyl ethyl ketone, methyl isobutyl ketone, cyclohexanone, and acetophenone.

Ester solvents: such as ethyl acetate, butyl acetate, methyl benzoate, and ethyl cellosolve acetate.

Chlorinated solvents: such as methylene chloride, chloroform, 1,2-dichloroethane, 1,1,2-trichloroethane, chlorobenzene, and o-dichlorobenzene.

Alcohol solvents: methanol, ethanol, propanol, isopropanol, cyclohexanol, and phenol.

Polyhydric alcohols and derivatives thereof: such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerol, and 1,2-hexanediol.

Aprotic polar solvents: such as dimethylsulfoxide, N-methyl-2-pyrrolidone, N,N-dimethylformamide, and N,N-dimethylacetoamide.

These organic solvents may be used alone, or two or more thereof may be used as a mixed solvent. In the case where the mixed solvent is used, it is preferable that two or three or more of the solvents in the solvent groups be used in combination; several solvents from the same solvent group described above may be used in combination, or one or more solvents from different solvent groups may be used in combination. The composition ratio can be determined considering the physical properties of the solvents, the solubility of the polymer compound, and the like.

Preferable examples in the case where several solvents are selected from the same solvent group and used in combination include several solvents from the aromatic hydrocarbon solvents, and several solvents from the aromatic ether solvents.

Preferable examples in the case where one or more solvents are selected from different solvent groups and used in combination include the following combinations:
the aromatic hydrocarbon solvent and the aliphatic hydrocarbon solvent;
the aromatic hydrocarbon solvent and the aromatic ether solvent;
the aromatic hydrocarbon solvent and the aliphatic ether solvents;
the aromatic hydrocarbon solvent and the aprotic polar solvent; and
the aromatic ether solvent and the aprotic polar solvent.
A single solvent or the mixed organic solvent can be added to water.

Among these organic solvents, a single solvent or mixed solvent containing one or more organic solvents having a structure including a benzene ring, a melting point of 0° C. or less, and a boiling point of 100° C. or more is preferable; among these, a single solvent or mixed solvent containing one or more of the aromatic hydrocarbon solvents and the aromatic ether solvents are particularly preferable from the viewpoint of viscosity and good film forming properties.

These organic solvents can be used alone, or two or more thereof can be used in combination as a mixed solvent; since the film forming properties can be controlled, it is preferable that the mixed solvent be used. When necessary, the organic solvent may be refined by a method such as washing, distillation, and contacting with an adsorbent, and used.

According to the liquid composition, the organic film containing the polymer compound according to the present embodiment can be easily produced. Specifically, the liquid composition is applied onto a substrate, and the organic solvent is distilled away by heating, sending air, reducing pressure, or the like; thereby, the organic film containing the polymer compound according to the present embodiment is obtained. In the distillation of the organic solvent, the condition can be changed depending on the organic solvent to be used; examples of the condition include an atmosphere temperature of 50 to 150° C. (heating) or a reduced pressure atmosphere of approximately $10^{-3}$ Pa.

As the application, an application method such as a spin coating method, a casting method, a microgravure method, a gravure coating method, a bar coating method, a roll coating method, a wire bar coating method, a dip coating method, a slit coating method, a capillary coating method, a spray coating method, a screen printing method, a flexographic printing method, an offset printing method, an inkjet print method, and a nozzle coating method can be used.

A suitable viscosity of the liquid composition varies depending on the printing method; the viscosity at 25° C. is preferably 0.5 to 1000 mPa·s, and more preferably 0.5 to 500 mPa·s. In the case where the liquid composition is passed through an ejecting apparatus as in the inkjet print method, to prevent clogging and curved flight of ink droplets during ejection, the viscosity at 25° C. is preferably 0.5 to 50 mPa·s, and more preferably 0.5 to 20 mPa·s. The concentration of the polymer compound according to the present embodiment in the liquid composition is not limited; it is preferable that the concentration be 0.01 to 10% by weight, and it is more preferable that the concentration be 0.1 to 5% by weight.

(Organic Film)

The organic film according to the present embodiment contains the polymer compound. The organic film according to the present embodiment can be easily produced from the liquid composition as above.

The organic film according to the present embodiment can be suitably used as a light-emitting layer in the light-emitting device described later. The organic film according to the present embodiment can also be suitably used for an organic semiconductor device. Because the organic film according to the present embodiment contains the polymer compound, the luminance life of the light-emitting device is excellent in the case where the organic film is used as the light-emitting layer in the light-emitting device (Light-Emitting Device)

The light-emitting device according to the present embodiment has the organic film.

Specifically, the light-emitting device according to the present embodiment has an anode, a cathode, and a layer existing between the anode and the cathode and containing the polymer compound. Here, it is preferable that the layer containing the polymer compound be a layer formed of the organic film, and the layer function as the light-emitting layer. Hereinafter, the case where the layer containing the polymer compound functions as the light-emitting layer will be exemplified as preferable one embodiment.

Examples of the light-emitting device according to the present embodiment include light-emitting devices having the following structures (a) to (d). The symbol "/" designates that the layers before and after the symbol are adjacent and laminated (for example, "anode/light-emitting layer" designates that the anode and the light-emitting layer are adjacent and laminated).

(a) anode/light-emitting layer/cathode
(b) anode/hole transport layer/light-emitting layer/cathode
(c) anode/light-emitting layer/electron transport layer/cathode
(d) anode/hole transport layer/light-emitting layer/electron transport layer/cathode The light-emitting layer is a layer having a light emission function.

The hole transport layer is a layer having a function to transport holes.

The electron transport layer is a layer having a function to transport electrons.

The hole transport layer and the electron transport layer are collectively referred to as a charge transport layer in some cases.

The hole transport layer adjacent to the light-emitting layer is referred to as an interlayer layer in some cases.

Lamination of the layers and film formation can be performed using a solution containing components that form each of the layers. In lamination and film forming from a solution, an application method such as a spin coating method, casting method, a microgravure coating method, a gravure coating method, a bar coating method, a roll coating method, a wire bar coating method, a dip coating method, a slit coating method, a capillary coating method, a spray coating method, a screen printing method, a flexographic printing method, an offset printing method, an inkjet print method, and a nozzle coating method can be used.

The thickness of the light-emitting layer may be selected such that the driving voltage, the light emission efficiency, and the luminance life are proper values; the thickness is usually 1 nm to 1 μm, preferably 2 nm to 500 nm, and still more preferably 5 nm to 200 nm.

It is preferable that the hole transport layer contain the hole transport material. Film formation of the hole transport layer may be performed by any method; in the case where the hole transport material is a polymer compound, it is preferable that film formation be performed from the solution containing the hole transport material; in the case where the hole transport material is a low-molecular compound, it is preferable that film formation be performed from a mixed solution containing a polymer binder and the hole transport material. As the film forming method, the same method as the application method above can be used.

As the polymer binder that can be mixed with the hole transport material, a compound that does not extremely inhibit charge transportation and whose absorption of visible light is not strong is preferable. Examples of the polymer binder include polycarbonate, polyacrylate, polymethylacrylate, polymethylmethacrylate, polystyrene, polyvinyl chloride, and polysiloxane.

The thickness of the hole transport layer may be selected such that the driving voltage, the light emission efficiency, and the luminance life are proper values; the thickness is usually 1 nm to 1 μm, preferably 2 nm to 500 nm, and still more preferably 5 nm to 200 nm.

It is preferable that the electron transport layer contain the electron transport material above. The film formation of the electron transport layer may be performed by any method; in the case where the electron transport material is a polymer compound, a method of forming a film from a solution containing the electron transport material, and a method of melting the electron transport material and forming a film or the like are preferable. In the case where the electron transport material is a low-molecular compound, a method of forming a film using a powder of the electron transport material by a vacuum evaporation method, a method of forming a film from a solution containing the electron transport material, and a method of melting the electron transport material and forming a film or the like are preferable. Examples of the method of forming a film from a solution containing the electron transport material can include the same method as the application method above. A polymer binder may be contained in the solution.

As the polymer binder that can be mixed with the electron transport material, a compound that does not extremely inhibit charge transportation and whose absorption of visible light is not strong is preferable. Examples of the polymer binder include poly(N-vinylcarbazole), polyaniline and derivatives thereof, polythiophene and derivatives thereof, poly(para-phenylenevinylene) and derivatives thereof, poly(2,5-thienylenevinylene) and derivatives thereof, polycarbonate, polyacrylate, polymethylacrylate, polymethyl methacrylate, polystyrene, polyvinyl chloride, and polysiloxane.

The thickness of the electron transport layer may be selected such that the driving voltage, the light emission efficiency, and the luminance life are proper values; the thickness is usually 1 nm to 1 μm, preferably 2 nm to 500 nm, and still more preferably 5 nm to 200 nm.

Among the charge transport layers provided adjacent to an electrode, a charge transport layer having a function to improve charge injection efficiency from the electrode and an effect of reducing the driving voltage of the device is particularly referred to as a charge injection layer (hole injection layer, electron injection layer) in some cases. In order to improve adhesion of the electrode and injection of charges from the electrode, the charge injection layer or insulating layer may be provided adjacent to the electrode; in order to improve adhesion of the interface and prevention of mixing, a thin buffer layer may be inserted into the interface between the charge transport layer and the light-emitting layer. The order and the number of the layers to be laminated and the thicknesses of the layers may be selected considering the light emission efficiency and luminance life.

Examples of the light-emitting device in which the charge injection layer is provided include light-emitting devices having the following structures (e) to (p):
(e) anode/charge injection layer/light-emitting layer/cathode
(f) anode/light-emitting layer/charge injection layer/cathode
(g) anode/charge injection layer/light-emitting layer/charge injection layer/cathode
(h) anode/charge injection layer/hole transport layer/light-emitting layer/cathode
(i) anode/hole transport layer/light-emitting layer/charge injection layer/cathode
(j) anode/charge injection layer/hole transport layer/light-emitting layer/charge injection layer/cathode
(k) anode/charge injection layer/light-emitting layer/charge transport layer/cathode
(l) anode/light-emitting layer/electron transport layer/charge injection layer/cathode
(m) anode/charge injection layer/light-emitting layer/electron transport layer/charge injection layer/cathode
(n) anode/charge injection layer/hole transport layer/light-emitting layer/charge transport layer/cathode
(o) anode/hole transport layer/light-emitting layer/electron transport layer/charge injection layer/cathode
(p) anode/charge injection layer/hole transport layer/light-emitting layer/electron transport layer/charge injection layer/cathode Examples of the charge injection layer include (I) a layer containing a conductive polymer, (II) a layer provided between the anode and the hole transport layer and containing a material having an ionization potential of a middle value between the anode material in the anode and the hole transport material in the hole transport layer, and (III) a layer provided between the cathode and the electron transport layer and a layer containing a material having an electron affinity force of a middle value between the cathode material in the cathode and the electron transport material in the electron transport layer.

In the case where the charge injection layer is (I) the layer containing a conductive polymer, it is preferable that the electric conductivity of the conductive polymer be $10^{-5}$ S/cm to $10^3$ S/cm; in order to reduce the leak current between light-emitting pixels, it is more preferable that the electric conductivity of the conductive polymer be $10^{-5}$ S/cm to $10^2$ S/cm, and it is still more preferable that the electric conductivity of the conductive polymer be $10^{-5}$ S/cm to $10^1$ S/cm. In order to satisfy the range, the conductive polymer may be doped with a proper amount of ion.

The kind of ions to be doped with is an anion for a hole injection layer, and a cation for the electron injection layer. Examples of the anion include polystyrenesulfonic acid ion, alkylbenzenesulfonic acid ion, and camphorsulfonic acid ion. Examples of the cation include lithium ion, sodium ion, potassium ion, and tetrabutylammonium ion.

It is preferable that the thickness of the charge injection layer be 1 to 100 nm, and it is more preferable that the thickness of the charge injection layer be 2 to 50 nm.

The conductive polymer may be selected according to the relationship with the electrode and the material of the adjacent layer; examples thereof include conductive polymers such as polyaniline and derivatives thereof, polythiophene and derivatives thereof, polypyrrole and derivatives thereof, polyphenylenevinylene and derivatives thereof, polythienylenevinylene and derivatives thereof, polyquinoline and derivatives thereof, polyquinoxaline and derivatives thereof, and polymers including an aromatic amine structure in the main chain or side chain. Examples of the charge injection layer include metal phthalocyanines (such as copper phthalocyanine) and layers containing carbon or the like.

The insulating layer is a layer having a function to facilitate injection of charges. The thickness of the insulating layer is usually 0.1 to 20 nm, preferably 0.5 to 10 nm, and more preferably 1 to 5 nm Examples of a material used as the insulating layer include metal fluorides, metal oxides, and organic insulating materials.

Examples of the light-emitting device in which the insulating layer is provided include light-emitting devices having the following structures (q) to (ab):
(q) anode/insulating layer/light-emitting layer/cathode
(r) anode/light-emitting layer/insulating layer/cathode
(s) anode/insulating layer/light-emitting layer/insulating layer/cathode
(t) anode/insulating layer/hole transport layer/light-emitting layer/cathode
(u) anode/hole transport layer/light-emitting layer/insulating layer/cathode
(v) anode/insulating layer/hole transport layer/light-emitting layer/insulating layer/cathode
(w) anode/insulating layer/light-emitting layer/electron transport layer/cathode
(x) anode/light-emitting layer/electron transport layer/insulating layer/cathode
(y) anode/insulating layer/light-emitting layer/electron transport layer/insulating layer/cathode
(z) anode/insulating layer/hole transport layer/light-emitting layer/electron transport layer/cathode
(aa) anode/hole transport layer/light-emitting layer/electron transport layer/insulating layer/cathode
(ab) anode/insulating layer/hole transport layer/light-emitting layer/electron transport layer/insulating layer/cathode It is preferable that the light-emitting device according to the present embodiment have a substrate adjacent to the anode or the cathode. As the substrate, a substrate whose shape and properties do not change when the electrode and the layers are formed are preferable; examples thereof include substrates made of glass, plastics, polymer films, silicon, and the like. In the case of the non-transparent substrate, it is preferable that an electrode opposite to an electrode that the substrate contacts be transparent or semi-transparent.

In the light-emitting device according to the present embodiment, usually, at least one of the electrodes composed of the anode and the cathode is transparent or semi-transparent; it is preferable that the anode be transparent or semi-transparent.

As the material for the anode, conductive metal oxide films, semi-transparent metal films, and the like are used. Specifically, films produced using a conductive inorganic compound such as composite oxides formed of indium oxide, zinc oxide, tin oxide, and indium tin oxide (ITO) and composite oxides formed of indium zinc oxide, NESA, gold, platinum, silver, copper, and the like are used. As the anode, an organic transparent conductive film formed of polyaniline and derivatives thereof, polythiophene and derivatives thereof, and the like may be used. In order to facilitate injection of charges, a layer formed of a phthalocyanine derivative, a conductive polymer, carbon, or the like, or a layer formed of a metal oxide, a metal fluoride, an organic insulating material, or the like may be provided on the anode.

Examples of the method of producing the anode include a vacuum evaporation method, a sputtering method, an ion plating method, and a plating method.

The thickness of the anode can be selected considering light transmittance and electric conductivity; the thickness is usually 10 nm to 10 µm, preferably 20 nm to 1 µm, and still more preferably 30 nm to 500 nm.

As the material for the cathode, a material whose work function is small is preferable; a metal such as lithium, sodium, potassium, rubidium, cesium, beryllium, magnesium, calcium, strontium, barium, aluminum, scandium, vanadium, zinc, yttrium, indium, cerium, samarium, europium, terbium, and ytterbium, an alloy containing two or more of the metals, an alloy containing one or more of the metals and one or more of gold, silver, platinum, copper, manganese, titanium, cobalt, nickel, tungsten, and tin, graphite or a graphite interlayer compound, and the like are used.

As the method of producing the cathode, a vacuum evaporation method, a sputtering method, a lamination method for thermally pressing a metal film, and the like are used.

The thickness of the cathode can be selected considering electric conductivity and durability; the thickness is usually 10 nm to 10 µm, preferably 20 nm to 1 µm, and still more preferably 50 nm to 500 nm.

A layer formed of a conductive polymer or a layer formed of a metal oxide, a metal fluoride, an organic insulating material, or the like may be provided between the cathode and the light-emitting layer or between the cathode and the electron transport layer; after production of the cathode, a protective layer for protecting the light-emitting device may be attached. In order to use the light-emitting device stably for a long time, it is preferable that a protective layer and/or a protective cover be attached to protect the light-emitting device from the outside.

As the protective layer, resins, metal oxides, metal fluorides, metal borides, and the like can be used. As the protective cover, a glass plate, a plastic plate whose surface is subjected to a low moisture permeation treatment; a method of bonding the protective cover to an device substrate with a thermosetting resin or a photocurable resin is suitably used. If a space is kept using a spacer, the device can be easily prevented from being scratched. If an inert gas such as nitrogen and argon is sealed in the space, oxidation of the cathode can be prevented; further, by providing a desiccant such as barium oxide inside of the space, suppression in moisture adsorbed during the production step damaging the device is easy.

FIG. 1 is a schematic sectional view showing one embodiment of a light-emitting device according to the present invention (light-emitting device having the structure (p)). The light-emitting device 100 shown in FIG. 1 has a substrate 10, an anode 11 formed on the substrate 10, a hole injection layer 12, a hole transport layer 13, a light-emitting layer 14, an electron transport layer 15, an electron injection layer 16, and a cathode 17. The anode 11 is provided on the substrate 10 so as to contact the substrate 10; on a side of the anode 11 opposite to the substrate 10, the hole injection layer 12, the hole transport layer 13, the light-emitting layer 14, the electron transport layer 15, the electron injection layer 16, and the cathode 17 are laminated in this order.

Figure 2:
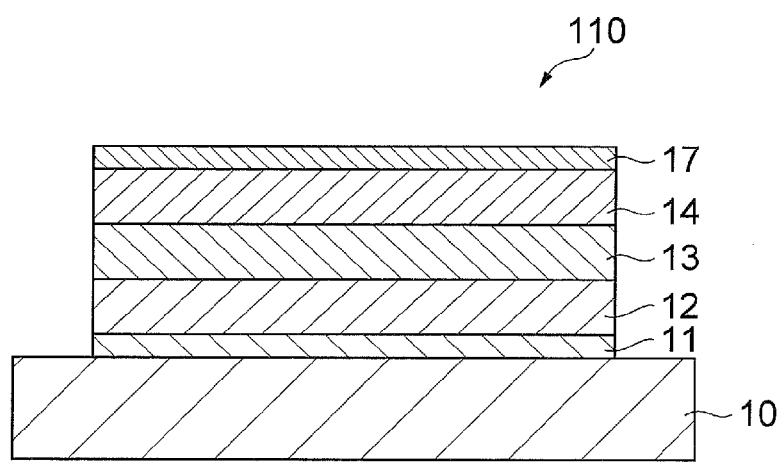
FIG. 2 is a schematic sectional view showing another embodiment of a light-emitting device according to the present invention.

FIG. 2 is a schematic sectional view showing another embodiment of the light-emitting device according to the present invention (light-emitting device having the structure (h)). The light-emitting device 110 shown in FIG. 2 has a substrate 10, an anode 11 formed on the substrate 10, a hole injection layer 12, a hole transport layer 13, a light-emitting layer 14, and a cathode 17. The anode 11 is provided on the substrate 10 so as to contact the substrate; on a side of the anode 11 opposite to the substrate 10, the hole injection layer 12, the hole transport layer 13, the light-emitting layer 14, and the cathode 17 are laminated in this order.

The light-emitting device containing the polymer compound according to the present embodiment is useful for surface lighting sources such as curved surface lighting sources and flat surface lighting sources (such as lighting); and display devices such as segment display devices, dot matrix display devices (such as dot matrix flat displays), and liquid crystal display devices (for example, liquid crystal display devices and backlights of liquid crystal displays), for example. The polymer compound according to the present embodiment is suitable for the material used in production of these; besides, the polymer compound according to the present embodiment is also suitable for dyes for a laser, a material for a conductive film such as materials for an organic solar cell, organic semiconductors for an organic transistor, conductive films, organic semiconductor films, a light-emittable film material that emits fluorescence, a material for polymer field-effect transistors, and the like.

In order to obtain a planar light emission using the light-emitting device according to the present embodiment, a planar anode and cathode may be disposed so as to be layered. In order to obtain a patterned light emission, a method in which a mask in which a patterned window is provided is provided on the surface of the planar light-emitting device, and a method in which one of the anode and the cathode or both of the electrode are formed to be patterned are used. A pattern is formed by any of these methods, and some of electrodes are arranged to be capable of being turned ON/OFF independently; thereby, a segment display device on which numerals, letters, simple symbols, and the like can be displayed is obtained.

Further, to obtain a dot matrix display device, the anode and the cathode both may be formed in a strip form and arranged intersecting perpendicular to each other. Partial color display and multicolor display are enabled by a method for applying polymer compounds of a plurality of different light-emitting colors, or a method using a color filter or a fluorescence conversion filter. The dot matrix display device can be passively driven, or may be actively driven in combination with a TFT or the like. These display devices can be used as display devices for computers, televisions, mobile terminals, mobile phones, car navigation systems, view finders for video cameras, and the like.

Figure 3:
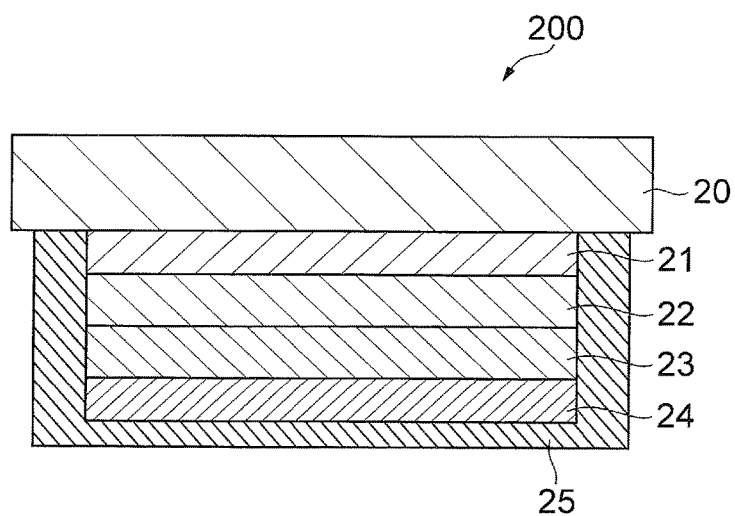
FIG. 3 is a schematic sectional view showing one embodiment of a surface lighting source according to the present invention.

FIG. 3 is a schematic sectional view showing one embodiment of the surface lighting source according to the present invention. The surface lighting source 200 shown in FIG. 3 includes a substrate 20, an anode 21, a hole injection layer 22, a light-emitting layer 23, a cathode 24, and a protective layer 25. The anode 21 is provided on the substrate 20 so as to contact the substrate 20; on a side of the anode 21 opposite to the substrate 20, the hole injection layer 22, the light-emitting layer 23, and the cathode 24 are laminated in this order. The protective layer 25 is formed so as to cover all the anode 21, the charge injection layer 22, the light-emitting layer 23, and the cathode 24 formed on the substrate 20 and contact the substrate 20 at the end. The polymer compound is contained in the light-emitting layer 23.

The surface lighting source 200 shown in FIG. 3 is configured to further have a plurality of light-emitting layers other than the light-emitting layer 23, and can be formed as a color display device by using a red light-emitting material, a blue light-emitting material, and a green light-emitting material for each of the light-emitting layers and controlling drive of the light-emitting layers.

EXAMPLES

Hereinafter, the present invention will be more specifically described using Examples, but the present invention will not be limited to Examples.

The polystyrene-equivalent number-average molecular weight and weight-average molecular weight of the polymer compound were determined using a gel permeation chromatograph (GPC) (made by SHIMADZU Corporation, trade name: LC-10Avp) on the following measurement condition.
<Measurement Condition>

The polymer compound to be measured was dissolved in tetrahydrofuran such that the concentration was approximately 0.05% by weight, and 10 μL of the solution was injected to the GPC. Tetrahydrofuran was used as a mobile phase for the GPC, and flowed at a flow rate of 2.0 mL/min. As a column, a PLgel MIXED-B (made by Polymer Laboratories Ltd.) was used. As a detector, a differential refractive index detector (made by SHIMADZU Corporation, trade name: RID-10A) was used.

Measurement of NMR was performed by dissolving 5 to 20 mg of a measurement sample in approximately 0.5 mL of an organic solvent and using an NMR (made by Varian, Inc., trade name: INOVA300).

Measurement of LC-MS was performed by the following method. A measurement sample was dissolved in a proper organic solvent (such as chloroform, tetrahydrofuran, ethyl acetate, and toluene) such that the concentration was 1 to 10 mg/mL, measured with an LC-MS (made by Agilent Technologies, Inc., trade name: 1100LCMSD), and analyzed. As a mobile phase for the LC-MS, ion exchange water, acetonitrile, tetrahydrofuran, or a mixed liquid thereof was used, and when necessary acetic acid was added. As a column, an L-column 2 ODS (3 μm) (made by Chemicals Evaluation and Research Institute, Japan, inner diameter: 4.6 mm, length: 250 mm, particle diameter: 3 μm) was used.

Example 1: Synthesis of Compound 5

(Synthesis of Compound 2)
First, using Compound 1, Compound 2 was synthesized as follows.

[Chemical Formula 58]

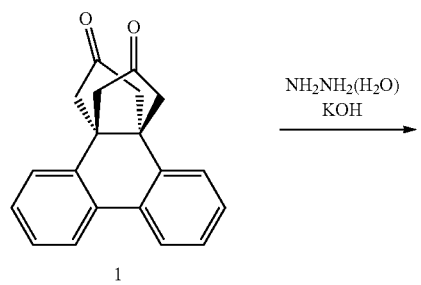

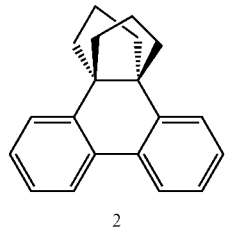

Compound 1 (4.5 g) and ethylene glycol (180 g) were placed in a 500 mL four-necked flask including a stirrer, and the gas inside of the flask was replaced with argon. Hydrazine monohydrate (3.2 g) and potassium hydroxide (4.3 g) were placed in the flask, and the temperature was raised to 180° C.; stirring was performed at the temperature for 28 hours while the temperature was kept. The reaction solution was cooled to room temperature, and water was added; then, a solid was precipitated. The solid was filtered, recovered, and dried by reducing pressure at room temperature; thereby, 3.9 g of Compound 2 was obtained as a white solid.
$^1$H-NMR (CDCl$_3$, 300 MHz) δ (ppm): 1.35-1.72 (4H, m), 1.89-2.24 (8H, m), 7.10-7.46 (6H, m), 7.90 (2H, d).
(Synthesis of Compound 3)
Next, using Compound 2, Compound 3 was synthesized as follows.

[Chemial Formula 59]

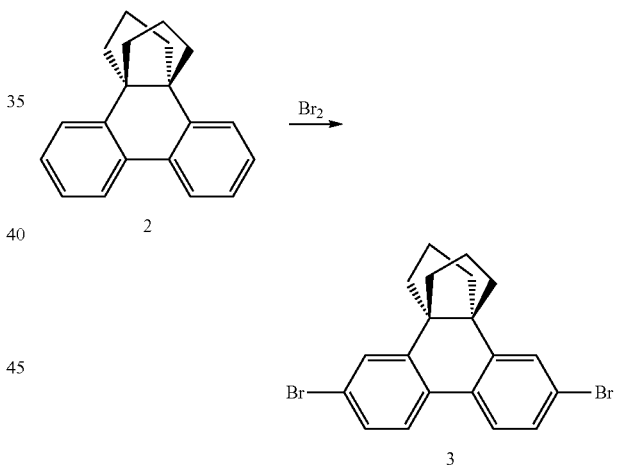

The gas inside of a 100 mL four-necked flask including a stirrer was replaced with argon, and Compound 2 (3.7 g), chloroform (45 g), and trifluoroacetic acid (7.5 mL) were added. The entire four-necked flask was shielded from light, and a mixture of bromine (5.7 g) and chloroform (11.2 g) was added at room temperature. Stirring was performed at room temperature for 2.5 hours while the temperature was kept, and a 10% by weight sodium sulfite aqueous solution (20 g) was added. An aqueous layer was separated from the reaction solution, and an organic layer was washed with water, a 10% by weight dipotassium hydrogenphosphate aqueous solution, and water in this order. The obtained organic layer was dried with magnesium sulfate, and filtered; the filtrate was condensed to obtain a crude product. The crude product was recrystallized with a mixed liquid of toluene and methanol; the obtained solid was dissolved in chloroform, and refined using a silica gel column (developing solvent of toluene/hexane). The obtained solution was condensed, and activated carbon (3 g) was added; stirring was performed at 65° C. for 0.5 hours while the temperature was kept. The solution was filtered at the temperature with a filter precoated with celite to obtain a filtrate and a residue. Next, the residue was washed with toluene several times to obtain a washing liquid. Here, the filtrate and the washing liquid obtained by washing several times were added, and partially condensed to obtain a toluene solution. Hexane was added to the toluene solution, and recrystallized; thereby, 3.6 g of Compound 3 was obtained as a white solid.

LC-MS (ESI, positive): [M+H]$^+$417.

$^1$H-NMR (CDCl$_3$, 300 MHz) δ (ppm): 1.38-1.76 (4H, m), 1.85-2.24 (8H, m), 7.33 (2H, d), 7.50 (2H, s), 7.70 (2H, d).

(Synthesis of Compound 4)

Next, using Compound 3, Compound 4 was synthesized as follows.

[Chemical Formula 60]

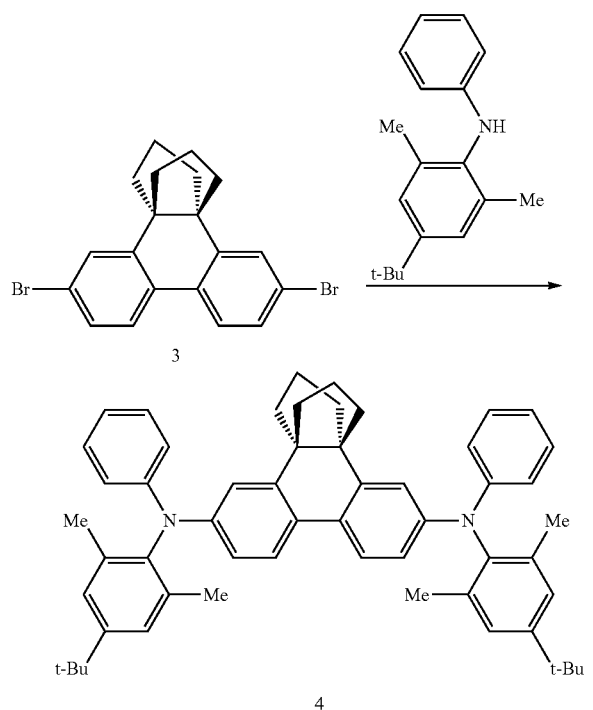

N-phenyl-N-(4-tert-butyl)-2,6-dimethyl phenyl amine (24.3 g), tris(dibenzylidene acetone)dipalladium(0) (1.99 g), tri-tert-butylphosphonium tetrafluoroborate (2.53 g), and sodium tert-butoxide (12.6 g) were placed in a 500 mL four-necked flask including a stirrer, and the gas inside of the flask was replaced with nitrogen. Toluene (100 mL) and tert-butanol (9 mL) were placed in the flask, and a mixture of Compound 3 (18.2 g) and toluene (170 mL) was dropped. Then, the temperature was raised to a reflux temperature, and stirring was performed for 2 hours while the temperature was kept.

The reaction solution was cooled to room temperature, and water was added; the reaction solution was filtered with a filter precoated with celite. The residue was washed with toluene, the aqueous layer was separated from the filtrate, and the organic layer was washed with water. The obtained organic layer was condensed to obtain a crude product. The crude product was refined using a silica gel column (devel-oping solvent of a hexane/toluene mixed liquid). The obtained solution was condensed, and recrystallized with a mixed liquid of isopropanol and toluene to obtain 30.6 g of Compound 4 as a white solid.

(Synthesis of Compound 5)

Next, using Compound 4, Compound 5 was synthesized as follows.

[Chemical Formula 61]

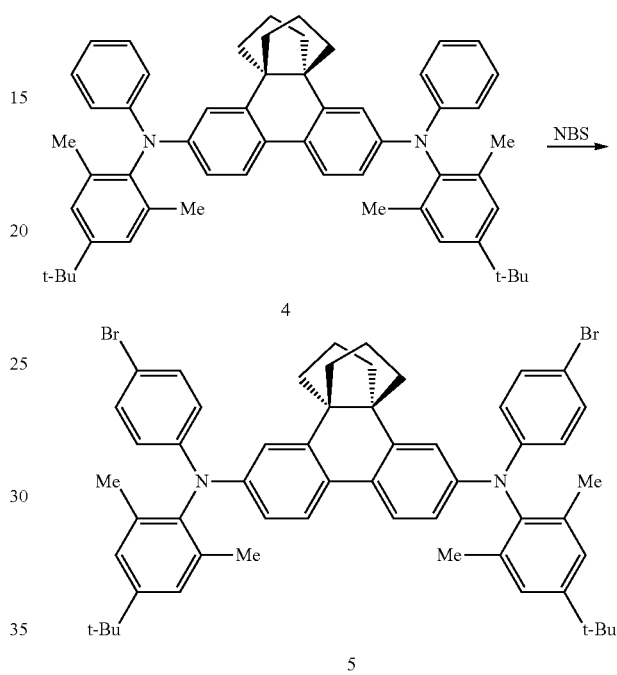

The gas inside of a 1 L four-necked flask including a stirrer was replaced with nitrogen; Compound 4 (30.1 g), N,N-dimethyl formamide (36 mL), chlorobenzene (360 mL), and chloroform (100 mL) were placed in the flask, and cooling was performed to 10° C. The flask was shielded from light, and N-bromosuccinimide (NBS) (14.2 g) was divided into several portions and added at 10° C. Stirring was performed at the temperature for 4 hours while the temperature was kept, and water was added; next, a saturated sodium sulfite aqueous solution was added until the color of bromine disappeared. The temperature was raised to room temperature; then, chloroform was added to the obtained solution, and the aqueous layer was separated. The organic layer was washed with water twice, and condensed to obtain a crude product. The crude product was dissolved in toluene; the temperature was raised to 65° C., and silica gel (75 g) and activated carbon (2 g) were added; stirring was performed for 30 minutes while the temperature was kept. The solution was filtered with a filter precoated with silica gel, and the residue was washed with toluene. Isopropanol was added to the obtained toluene solution to perform recrystallization; then, recrystallization was further performed with a mixed liquid of toluene and isopropanol to obtain 29.8 g of Compound 5 as a white solid.

LC-MS (APCI, positive): [M+H]$^+$919.

$^1$H-NMR (CDCl$_3$, 300 MHz) δ (ppm): 1.11-1.63 (22H, m), 1.80-2.08 (20H, m), 6.53-6.70 (2H, br), 6.75-6.90 (4H, m), 7.05-7.36 (10H, m), 7.50-7.66 (2H, br).

Example 2: Synthesis of Compound 10

(Synthesis of Compound 6)
First, using Compound 1, Compound 6 was synthesized as follows.

[Chemical Formula 62]

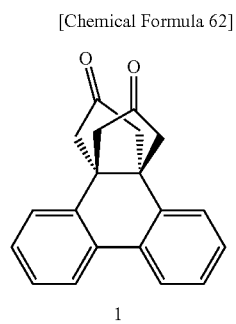

n-C$_7$H$_{15}$PPh$_3$Br
KOt-Bu
→

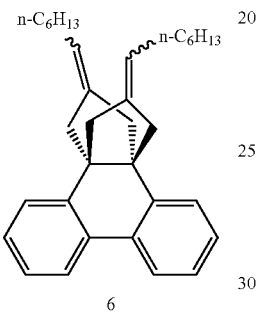

(wherein the wavy line indicates that the compound having the wavy line is a geometric isomer mixture).

n-Heptyltriphenylphosphonium bromide (115.0 g) was placed in a 1 L four-necked flask including a stirrer, and the gas inside of the flask was replaced with argon. Toluene (375 g) was placed in the flask, and cooling was performed to 5° C. or less. Potassium tert-butoxide (29.2 g) was placed in the flask, and the temperature was raised to room temperature; then, stirring was performed at room temperature for 3 hours while the temperature was kept. Compound 1 (15.0 g) was added to a red slurry produced during the reaction solution, and stirring was performed at room temperature for 12 hours while the temperature was kept. Acetic acid (10.0 g) was added to the reaction solution, and stirring was performed for 15 minutes; the reaction solution was filtered to obtain a filtrate and a residue. Next, the residue was washed with toluene several times to obtain a washing liquid. Here, the filtrate and the washing liquid obtained by washing several times were added, and condensed; when hexane was added, a slurry was produced; the slurry was stirred at 50° C. for 1 hour while the temperature was kept. The obtained mixture was cooled to room temperature, and filtered to obtain a filtrate and a residue. Next, the residue was washed with hexane several times to obtain a washing liquid. Here, the filtrate and the washing liquid obtained by washing several times were added, and condensed to obtain a crude product. The crude product was refined using a silica gel column (developing solvent of hexane) to obtain 21.7 g of Compound 6 as a colorless transparent liquid.

LC-MS (ESI, positive, KCl added): [M+K]$^+$491.
$^1$H-NMR (CDCl$_3$, 300 MHz) δ (ppm): 0.87 (6H, t), 1.20-1.36 (16H, m), 1.82-1.97 (4H, m), 2.57-2.81 (8H, m), 5.20 (2H, br), 7.23-7.32 (4H, m), 7.41-7.48 (2H, m), 7.87-7.90 (2H, m).

(Synthesis of Compound 7)
Next, using Compound 6, Compound 7 was synthesized as follows.

[Chemical Formula 63]

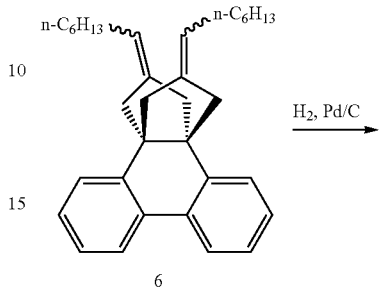

H$_2$, Pd/C
→

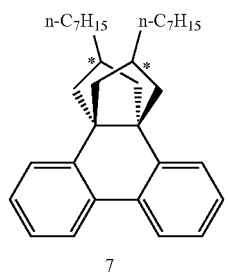

(wherein the wavy line indicates that the compound having the wavy line is a geometric isomer mixture; * indicates that a carbon atom to which * is attached is an asymmetric carbon atom).

Compound 6 (21.7 g) was placed in a 1 L four-necked flask including a stirrer, and ethyl acetate (152.4 g) and ethanol (151.6 g) were placed in the flask; the gas inside of the flask was replaced with nitrogen. 5% by weight Pd/C (a product containing approximately 50% by weight of water) (4.3 g) was added; then, the gas inside of the flask was replaced with hydrogen; under a hydrogen atmosphere, stirring was performed at 40° C. for 27 hours while the temperature was kept. Cooling was performed to room temperature, and filtration was performed with a filter pre-coated with celite to obtain a filtrate and a residue. Next, the residue was washed with ethyl acetate several times to obtain a washing liquid. Here, the filtrate and the washing liquid obtained by washing several times were added, and condensed to obtain a crude product. The crude product was refined using a silica gel column (developing solvent of hexane) to obtain 21.7 g of Compound 7 as a colorless transparent liquid.

LC-MS (APPI, positive): [M]$^+$456.
$^1$H-NMR (CDCl$_3$, 300 MHz) δ (ppm): 0.66-0.98 (6H, m), 1.00-2.22 (34H, m), 7.13-7.50 (6H, m), 7.80-7.98 (2H, m).

(Synthesis of Compound 8)
Next, using Compound 7, Compound 8 was synthesized as follows.

[Chemical Formula 64]

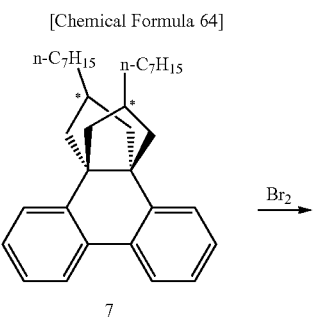

7

(wherein * indicates that a carbon atom to which * is attached is an asymmetric carbon atom).

Compound 7 (21.7 g), chloroform (261.1 g), and trifluoroacetic acid (44 g) were placed in a 500 mL four-necked flask including a stirrer, and the gas inside of the flask was replaced with argon. The entire four-necked flask was shielded from light, and a mixture of bromine (19.0 g) and chloroform (65.3 g) was dropped into the flask at room temperature over 15 minutes; then, the temperature was raised to 35° C. Stirring was performed at 35° C. for 7 hours while the temperature was kept; then, cooling was performed to 15° C. or less. A 10% by weight sodium sulfite aqueous solution (109 g) was added to the reaction solution, and the temperature was raised to room temperature. An aqueous layer was separated from the reaction solution, and an organic layer was washed with water, a 5% by weight sodium hydrogencarbonate aqueous solution, and water in this order. The obtained organic layer was dried with magnesium sulfate, and filtered; the filtrate was condensed to obtain a crude product. The crude product was recrystallized twice with a mixed liquid of ethanol and hexane. The obtained solid was dissolved in hexane, and refined using a silica gel column (developing solvent of hexane); activated carbon (2.1 g) was added to the obtained hexane solution, and the solution was stirred at 45° C. for 1 hour while the temperature was kept. The obtained mixture was cooled to room temperature, and filtered with a filter precoated with celite to obtain a filtrate and a residue. Next, the residue was washed with hexane several times to obtain a washing liquid. Here, the filtrate and the washing liquid obtained by washing several times were added, and partially condensed to obtain a hexane solution. Ethanol was added to the hexane solution, and recrystallization was performed to obtain 18.8 g of Compound 8 as a white solid.

LC-MS (ESI, negative, KCl added): [M+Cl]⁻648.

$^1$H-NMR (CDCl$_3$, 300 MHz) δ (ppm): 0.66-0.98 (6H, m), 1.00-2.20 (34H, m), 7.22-7.78 (6H, m).

From the $^1$H-NMR measurement result, it was found out that Compound 8 is a mixture of isomers with different stereochemistry (9a:9b:9c=51:39:10) (molar ratio).

[Chemical Formula 65]

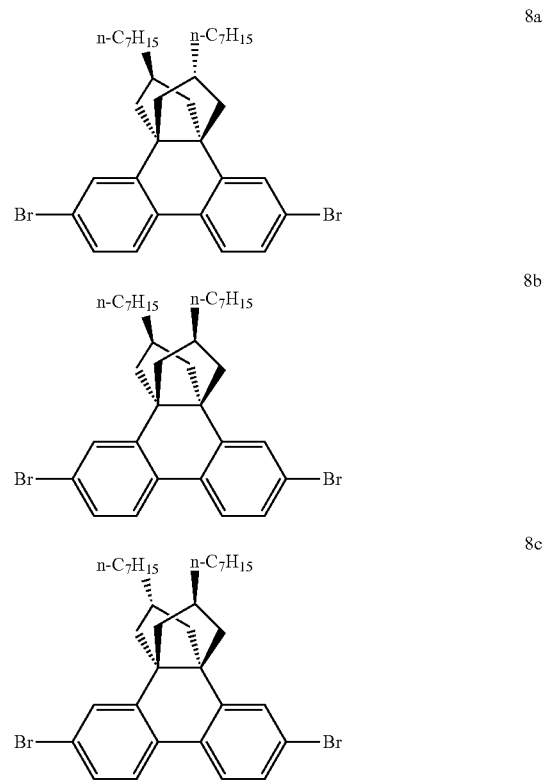

(Synthesis of Compound 9)

Next, using Compound 8, Compound 9 was synthesized as follows.

[Chemical Formula 66]

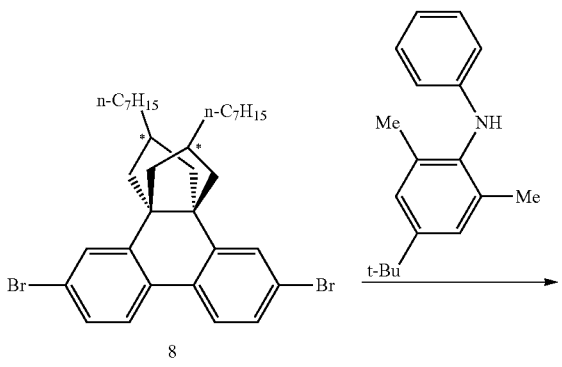

-continued

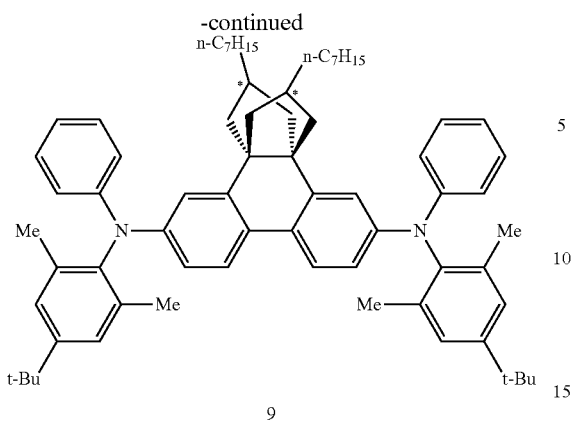

9

-continued

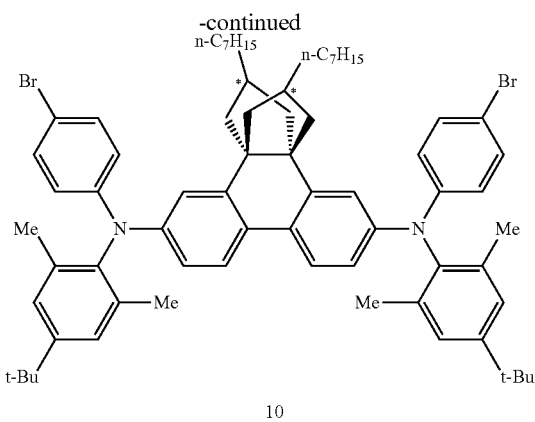

10

(wherein * indicates that a carbon atom to which * is attached is an asymmetric carbon atom).

N-phenyl-N-(4-tert-butyl)-2,6-dimethyl phenyl amine (4.53 g), tris(dibenzylidene acetone)dipalladium(0) (0.37 g), tri-tert-butyl phosphonium tetrafluoroborate (0.71 g), and sodium tert-butoxide (2.35 g) were placed in a 500 mL four-necked flask including a stirrer, and the gas inside of the flask was replaced with argon. Xylene (50 mL) and tert-butanol (10 mL) were added to the flask, and a mixture of Compound 8 (5.00 g) and xylene (50 mL) was dropped. Then, the temperature was raised to a reflux temperature, and stirring was performed for 3 hours while the temperature was kept. The reaction solution was cooled to room temperature, and water and toluene were added; the reaction solution was stirred at room temperature; then, an aqueous layer was separated, and an organic layer was washed with a saturated sodium chloride aqueous solution. Sodium sulfate was added to the obtained organic layer, and filtration and then condensation were performed to obtain a crude product. The crude product was refined using a silica gel column (developing solvent of hexane/toluene mixed liquid). The obtained solution was condensed, and recrystallized with a mixed liquid of isopropanol and toluene to obtain 5.0 g of Compound 9 as a white solid.

(Synthesis of Compound 10)

Next, Compound 10 was synthesized using Compound 9 as follows.

(wherein * indicates that a carbon atom to which * is attached is an asymmetric carbon atom).

The gas inside of a 1 L four-necked flask including a stirrer was replaced with argon; Compound 9 (4.25 g), N,N-dimethyl formamide (4 mL), and chlorobenzene (20 mL) were placed in the flask, and cooling was performed to 10° C. The flask was shielded from light, and N-bromosuccinimide (NBS) (1.59 g) was divided into several portions and added at 10° C. Then, the temperature was raised to room temperature, and stirring was performed for 17 hours while the temperature was kept; then, water was added; next, a saturated sodium sulfite aqueous solution was added until the color of bromine disappeared. The temperature was raised to room temperature, hexane was added to the reaction solution, and an aqueous layer was separated. The organic layer was washed once with water, and once with a saturated sodium chloride aqueous solution, and condensed to obtain a crude product. The crude product was refined using a silica gel column (developing solvent of hexane/toluene mixed liquid). The obtained solution was condensed, and recrystallized with isopropanol to obtain 3.8 g of Compound 10 as a white solid.

LC-MS (APCI, positive): [M+H]$^+$1115.

$^1$H-NMR (CDCl$_3$, 300 MHz) δ (ppm): 0.71-0.98 (6H, m), 0.98-2.31 (64H, m), 6.39-7.86 (18H, m).

From the $^1$H-NMR and HPLC measurement results, it was found out that Compound 10 is a mixture of isomers with different stereochemistry (10a:10b:10c=49:46:5) (molar ratio).

[Chemical Formula 67]

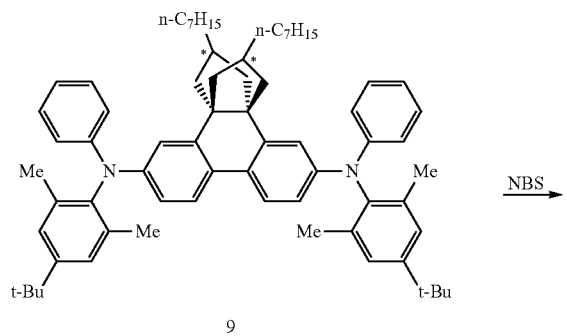

9

NBS →

[Chemical Formula 68]

10a

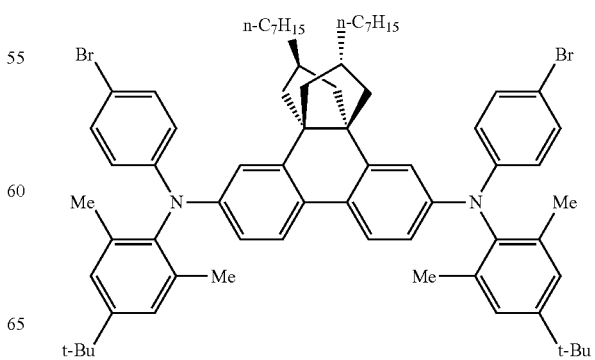

-continued

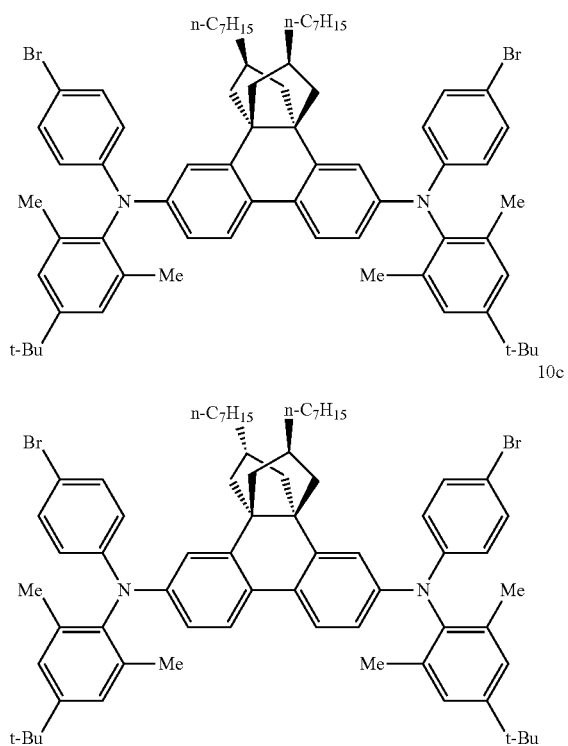

Synthesis Example 1: Synthesis of Compound 13

(Synthesis of Compound 11)
Using 1,5-naphthyl bis(trifluoromethanesulfonate), Compound 11 was synthesized as follows.

[Chemical Formula 69]

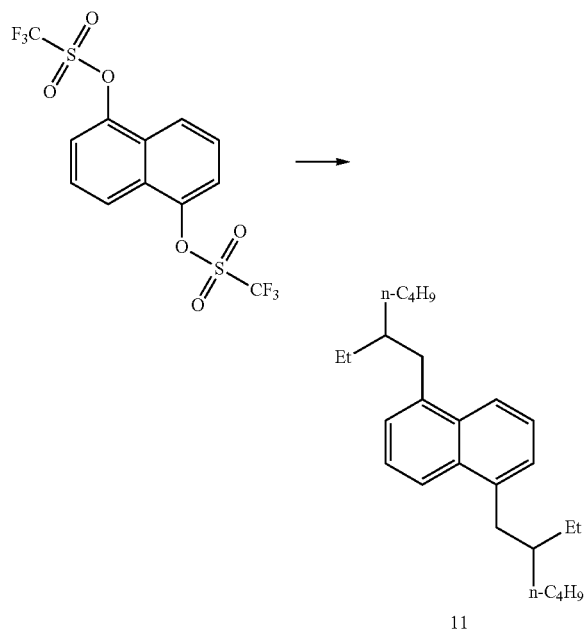

Under a nitrogen atmosphere, 1,5-naphthyl bis(trifluoromethanesulfonate) (25.0 g), a [1,1'-bis(diphenylphosphino)ferrocene]dichloropalladium (II)dichloromethylene adduct (0.24 g), and tert-butylmethylether (410 mL) were prepared, 2-ethylhexylmagnesium bromide (173 mL of a 1 mol/L diethyl ether solution) was dropped at 10° C. or less, and stirring was performed at room temperature for 4 hours. After the reaction was completed, the reaction solution was poured to a mixed liquid of water (500 ml) and 2 N hydrochloric acid (100 ml), and extracted with ethyl acetate; the obtained organic layer was washed with a sodium chloride aqueous solution; the washed organic layer was dried with magnesium sulfate, and the solvent was distilled away under reduced pressure. The residue was refined by silica gel column chromatography (developing solvent of hexane) to obtain 21.3 g of Compound 11 as a light yellow oil product.

LC-MS (ESI, positive): [M+]353.
$^1$H-NMR (300 MHz, CDCl$_3$) δ (ppm): 0.75-1.00 (12H, m), 1.10-1.50 (16H, m), 1.69-1.85 (2H, m), 2.90-3.05 (4H, m), 7.24-7.38 (3H, m), 7.35-7.44 (3H, m), 7.90-7.95 (3H, m).

(Synthesis of Compound 12)
Next, using Compound 11, Compound 12 was synthesized as follows.

[Chemical Formula 70]

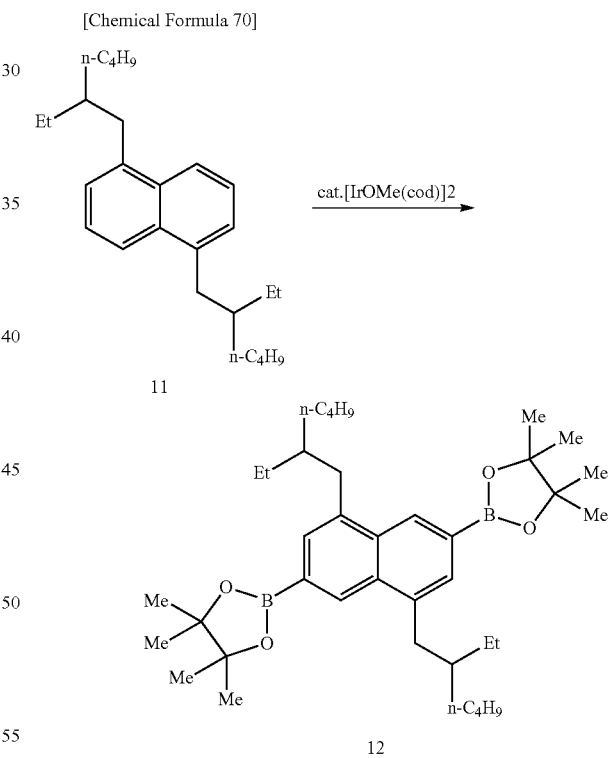

Under a nitrogen atmosphere, a mixture of Compound 10 (21.3 g), bis(pinacolate)diboron (4,4,4',4',5,5,5',5'-octamethyl-2,2'-bi-1,3,2-dioxaborolane) (46.0 g), bis(1,5-cyclooctadiene)di-μ-methoxydiiridium(I) (0.24 g) (made by Sigma-Aldrich Corporation), 4,4'-di-tert-butyl-2,2'-dipyridyl (0.19 g), and dioxane (140 mL) was stirred at 100° C. for 3 hours. After cooling, dioxane was distilled away under reduced pressure, and methanol (200 mL) was added to the residue; a precipitated solid was filtered out, and dried. The obtained solid was dissolved in toluene (250 mL), activated clay (20 g) was added, and the solution was stirred at 60° C. for 30 minutes. Then, the solution was filtered with a filter precoated with silica gel while the solution was hot, and the obtained filtrate was condensed under reduced pressure. Methanol (250 mL) was added to the obtained condensed product; a precipitated solid was filtered out, and dried to obtain 28.0 g of Compound 12 as a white powder.

LC-MS (ESI, positive): [M$^+$]605.

$^1$H-NMR (300 MHz, CDCl$_3$) δ (ppm): 0.85-0.95 (12H, m), 1.24-1.50 (16H, m), 1.66-1.85 (2H, m), 2.90-3.18 (4H, m), 7.60 (2H, s), 8.47 (2H, s).

(Synthesis of Compound 13)

Next, using Compound 12, Compound 13 was synthesized as follows.

[Chemical Formula 71]

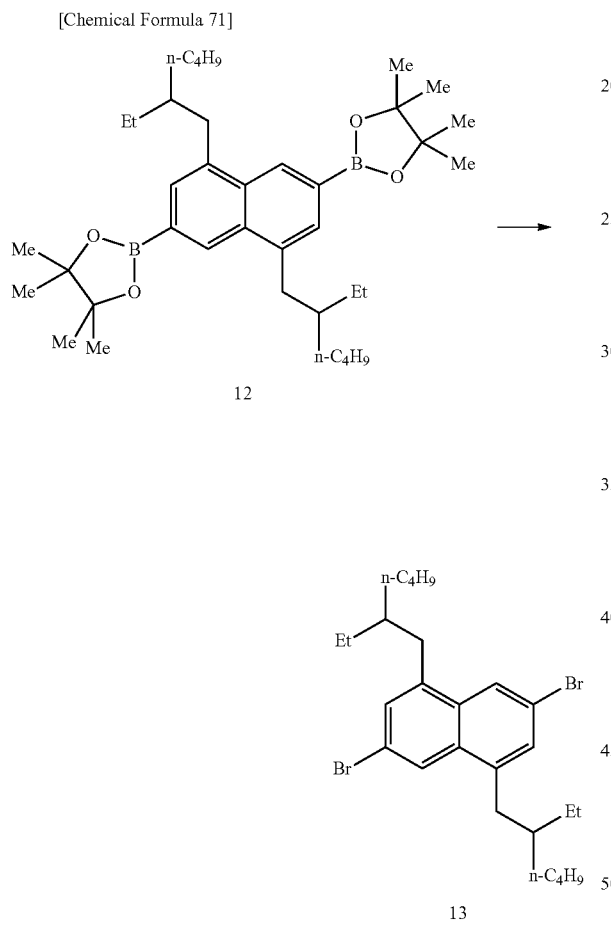

Under a nitrogen atmosphere, copper bromide(II) (62.7 g) was added to a mixed liquid of Compound 11 (28.0 g), dioxane (420 mL), N,N-dimethylformamide (420 mL), and water (210 mL), and stirring was performed at 95° C. for 2 hours. Further, copper bromide(II) (31.4 g) was added at the same temperature, and stirring was performed for 1.5 hours. Then, copper bromide(II) (31.4 g) was further added at the same temperature, and stirring was performed for 1.5 hours. The reaction solution was cooled; hexane (300 mL) was added, and stirring was performed. Then, an organic layer was separated, and dried with magnesium sulfate; the solvent was distilled away under reduced pressure. The residue was refined by silica gel column chromatography (developing solvent of hexane), and condensed to obtain a solid (21.0 g). The obtained solid was dissolved in toluene (150 mL), activated carbon (5 g) was added, and stirring was performed at 60° C. for 30 minutes. Then, the obtained mixture was filtered with a filter precoated with celite while the mixture was hot, and the obtained filtrate was condensed under reduced pressure. The obtained condensed product was recrystallized with a mixed liquid of toluene and methanol to obtain 13.2 g of Compound 12 as a white solid.

LC-MS (ESI, positive) [M$^+$]511.

$^1$H-NMR (300 MHz, CDCl$_3$) δ (ppm): 0.80-0.98 (12H, m), 1.20-1.44 (16H, m), 1.64-1.80 (2H, m), 2.77-2.95 (4H, m), 7.37 (2H, s), 8.00 (2H, s).

Example 3: Synthesis of Polymer Compound A1

Synthesis of a polymer (Polymer Compound A1) having the constitutional unit represented by the following formula (K-1), the constitutional unit represented by the following formula (K-2), and the constitutional unit represented by the following formula (K-3) at a molar ratio of 5:50:45 (a theoretical value based on prepared raw materials) was performed as follows.

[Chemical Formula 72]

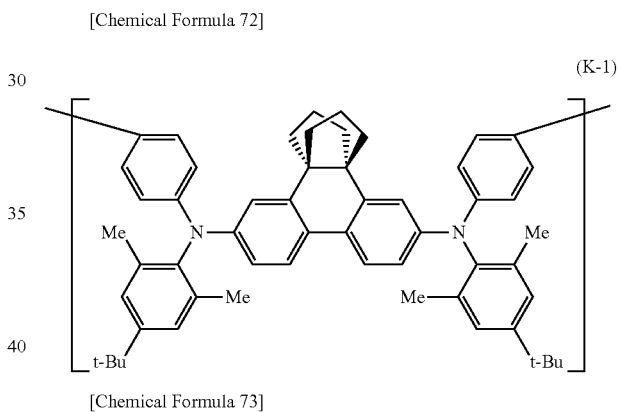

[Chemical Formula 73]

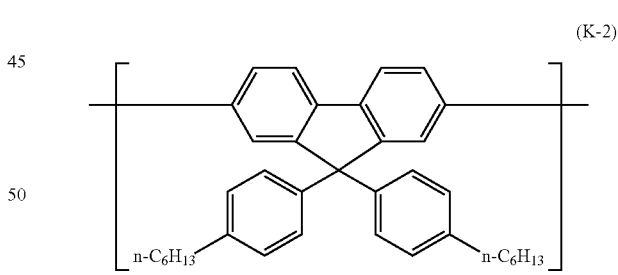

[Chemical Formula 74]

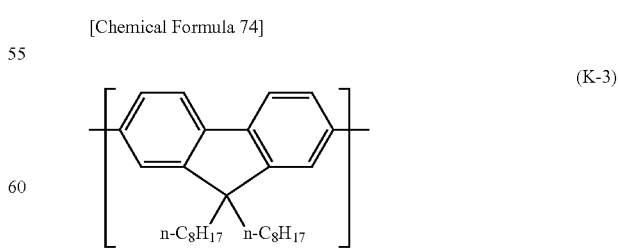

Under an argon atmosphere, Compound 5 synthesized in Example 1 (0.184 g, 0.20 mmol), the compound (1.477 g, 2.00 mmol) represented by the following formula (M-2-E):

[Chemical Formula 75]

(M-2-E)

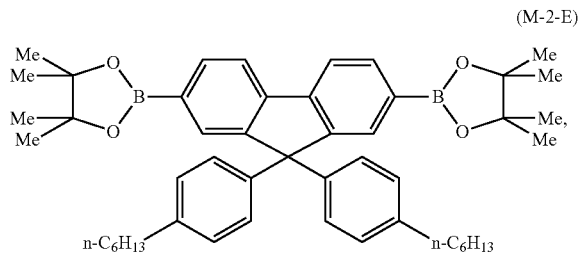

the compound (0.987 g, 1.80 mmol) represented by the following formula (M-3-BR):

[Chemical Formula 76]

(M-3-BR)

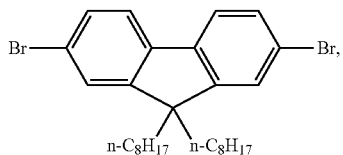

palladium acetate (1.35 mg), tris(o-methoxy phenyl)phosphine (14.8 mg), and toluene (44 mL) were mixed, and heated to 105° C. A 20% by weight tetraethylammonium hydroxide aqueous solution (6.9 g) was dropped into the reaction solution, and refluxing was performed for 2 hours. After the reaction, phenyl boronic acid (24.4 mg) and toluene (5 mL) were added thereto, and refluxing was further performed for 2 hours. Next, a sodium diethyldithiocarbamate aqueous solution was added thereto, and stirring was performed at 80° C. for 2 hours. The obtained mixture was cooled, and toluene was prepared; the mixture was washed twice with water, twice with a 3% by weight acetic acid aqueous solution, and twice with water. The obtained solution was dropped into methanol, and filtered to obtain a precipitate. This precipitate was dissolved in toluene, and the solution was passed through an alumina column and a silica gel column sequentially; thereby, the solution was refined. The obtained solution was dropped into methanol, and stirred; the obtained precipitate was filtered out, and dried; thereby, 1.09 g of Polymer Compound A1 was obtained. The polystyrene-equivalent number-average molecular weight of Polymer Compound A1 was $9.80 \times 10^4$, and the polystyrene-equivalent weight-average molecular weight thereof was $2.54 \times 10^5$.

Example 4: Synthesis of Polymer Compound A2

Synthesis of a polymer (Polymer Compound A2) having the constitutional unit represented by the following formula (K-1), the constitutional unit represented by the following formula (K-2), the constitutional unit represented by the following formula (K-3), and the constitutional unit represented by the following formula (K-4) at a molar ratio of 5:50:25:20 (a theoretical value based on prepared raw materials) was performed as follows.

[Chemical Formula 77]

(K-1)

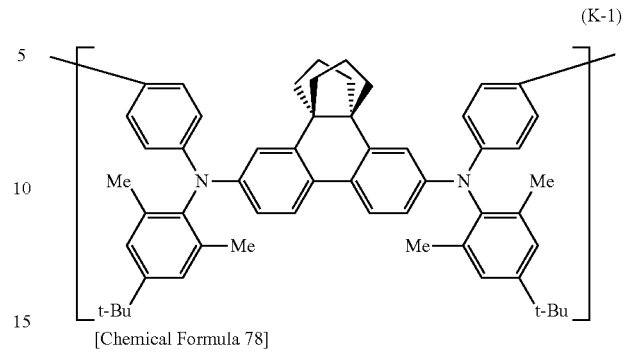

[Chemical Formula 78]

(K-2)

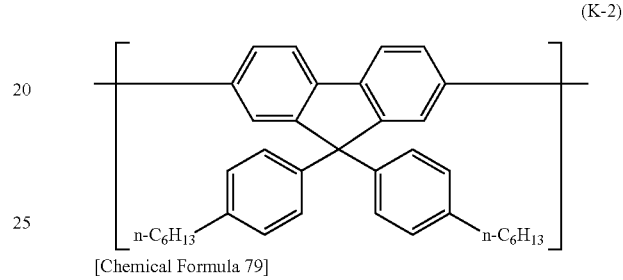

[Chemical Formula 79]

(K-3)

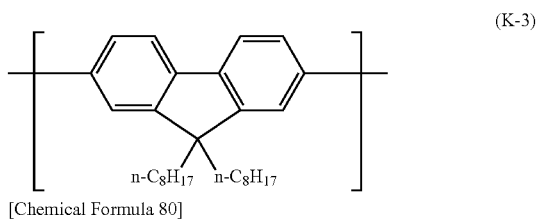

[Chemical Formula 80]

(K-4)

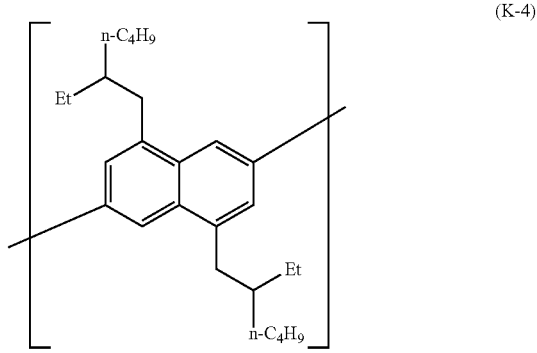

Under an argon atmosphere, Compound 5 synthesized in Example 1 (0.184 g, 0.20 mmol), the compound (1.477 g, 2.00 mmol) represented by the following formula (M-2-E):

[Chemical Formula 81]

(M-2-E)

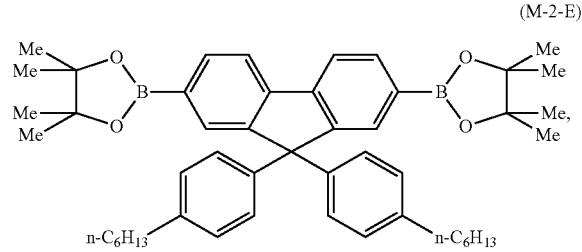

the compound (0.548 g, 1.00 mmol) represented by the following formula (M-3-BR):

[Chemical Formula 82]

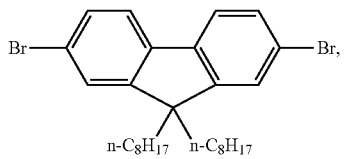

(M-3-BR)

Compound 13 synthesized in Synthesis Example 1 (0.408 g, 0.80 mmol), palladium acetate (1.35 mg), tris(o-methoxyphenyl)phosphine (14.8 mg), and toluene (44 mL) were mixed, and heated to 105° C. A 20% by weight tetraethylammonium hydroxide aqueous solution (6.9 g) was dropped into the reaction solution, and refluxing was performed for 2 hours. After the reaction, phenyl boronic acid (24.4 mg) and toluene (5 mL) were added thereto, and refluxing was further performed for 2 hours. Next, a sodium diethyldithiocarbamate aqueous solution was added thereto, and stirring was performed at 80° C. for 2 hours. The obtained mixture was cooled, and toluene was prepared; the mixture was washed twice with water, twice with a 3% by weight acetic acid aqueous solution, and twice with water. The obtained solution was dropped into methanol, and filtered to obtain a precipitate. The precipitate was dissolved in toluene, and the solution was passed through an alumina column and a silica gel column sequentially; thereby, the solution was refined. The obtained solution was dropped into methanol, and stirred; the obtained precipitate was filtered out, and dried; thereby, 1.90 g of Polymer Compound A2 was obtained. The polystyrene-equivalent number-average molecular weight of Polymer Compound A2 was $9.5 \times 10^4$, and the polystyrene-equivalent weight-average molecular weight thereof was $2.60 \times 10^5$.

Example 5: Synthesis of Polymer Compound A3

Synthesis of a polymer (Polymer Compound A3) having the constitutional unit represented by the following formula (K-5), the constitutional unit represented by the following formula (K-2), the constitutional unit represented by the following formula (K-3), and the constitutional unit represented by the following formula (K-6) at a molar ratio of 3:50:45:2 (a theoretical value based on prepared raw materials) was performed as follows.

[Chemical Formula 83]

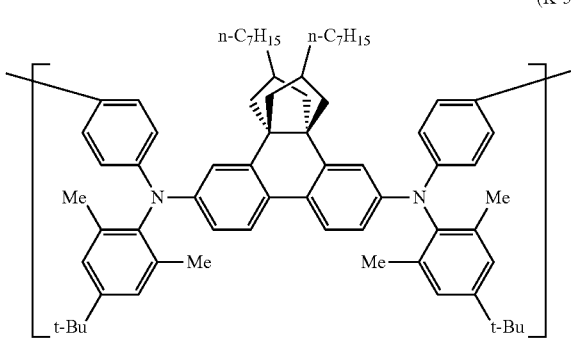

(K-5)

[Chemical Formula 84]

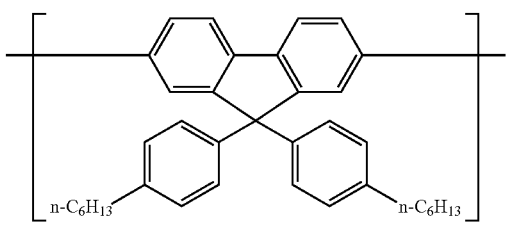

(K-2)

[Chemical Formula 85]

(K-3)

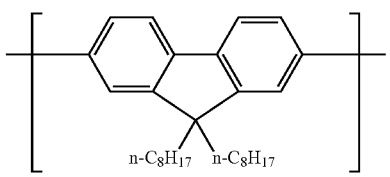

[Chemical Formula 86]

(K-6)

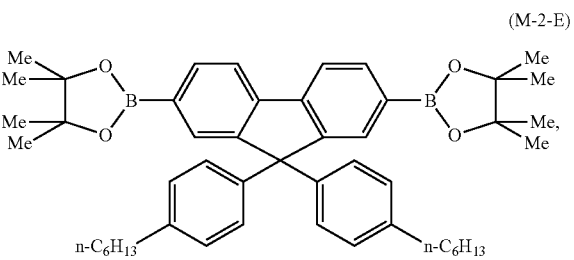

Under an argon atmosphere, Compound 10 synthesized in Example 2 (0.134 g, 0.12 mmol), the compound (1.477 g, 2.00 mmol) represented by the following formula (M-2-E):

[Chemical Formula 87]

(M-2-E)

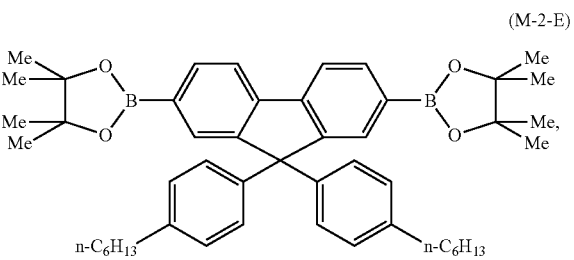

the compound (0.987 g, 1.80 mmol) represented by the following formula (M-3-BR):

[Chemical Formula 88]

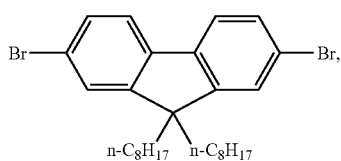

(M-3-BR)

the compound (0.088 g, 0.08 mmol) represented by the following formula (M-6-BR):

[Chemical Formula 89]

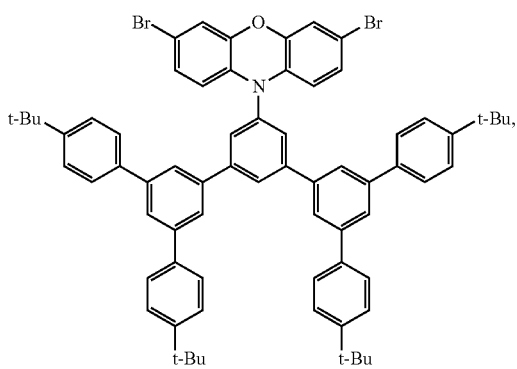

(M-6-BR)

palladium acetate (1.35 mg), tris(o-methoxy phenyl)phosphine (14.8 mg), and toluene (44 mL) were mixed, and heated to 105° C. A 20% by weight tetraethylammonium hydroxide aqueous solution (6.9 g) was dropped into the reaction solution, and refluxing was performed for 2 hours. After the reaction, phenyl boronic acid (24.4 mg) and toluene (5 mL) were added thereto, and refluxing was further performed for 2 hours. Next, a sodium diethyldithiocarbamate aqueous solution was added thereto, and stirring was performed at 80° C. for 2 hours. The obtained mixture was cooled, and toluene was prepared; the mixture was washed twice with water, twice with a 3% by weight acetic acid aqueous solution, and twice with water. The obtained solution was dropped into methanol, and filtered to obtain a precipitate. The precipitate was dissolved in toluene, and the solution was passed through an alumina column and a silica gel column sequentially; thereby, the solution was refined. The obtained solution was dropped into methanol, and stirred; the obtained precipitate was filtered out, and dried; thereby, 1.40 g of Polymer Compound A3 was obtained. The polystyrene-equivalent number-average molecular weight of Polymer Compound A3 was $1.39 \times 10^5$, and the polystyrene-equivalent weight-average molecular weight thereof was $4.13 \times 10^5$.

Example 6: Synthesis of Polymer Compound A4

Synthesis of a polymer (Polymer Compound A4) having the constitutional unit represented by the following formula (K-1), the constitutional unit represented by the following formula (K-2), the constitutional unit represented by the following formula (K-7), and the constitutional unit represented by the following formula (K-8) at a molar ratio of 3:37:50:10 (a theoretical value based on prepared raw materials) was performed as follows.

[Chemical Formula 90]

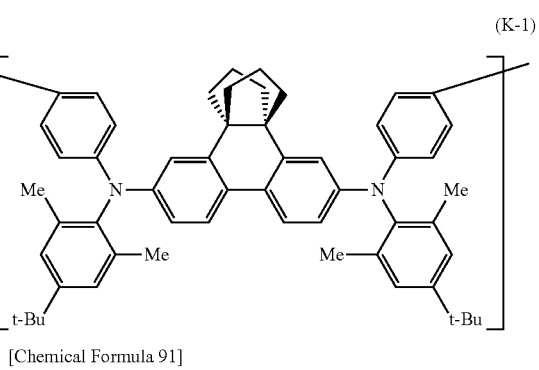

(K-1)

[Chemical Formula 91]

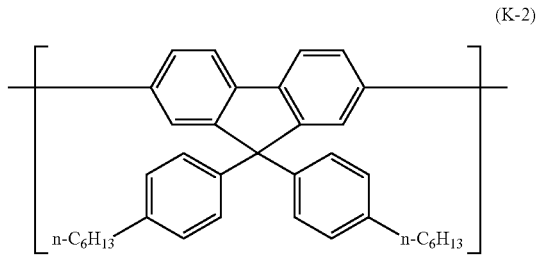

(K-2)

[Chemical Formula 92]

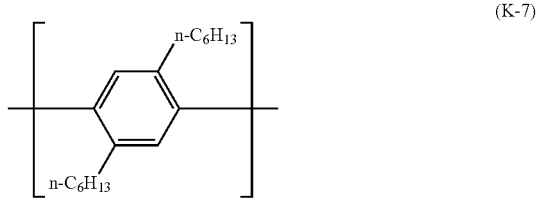

(K-7)

[Chemical Formula 93]

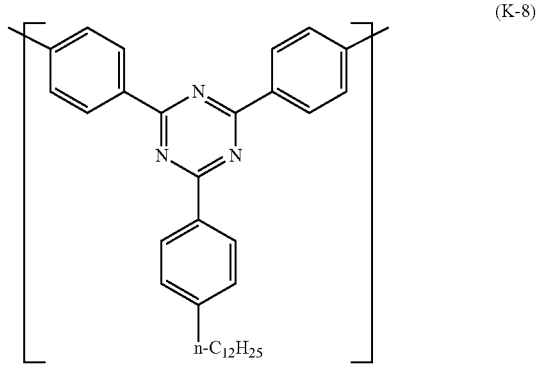

(K-8)

Under an argon atmosphere, Compound 5 synthesized in Example 1 (0.111 g, 0.12 mmol), the compound (0.954 g, 1.48 mmol) represented by the following formula (M-2-BR):

[Chemical Formula 94]

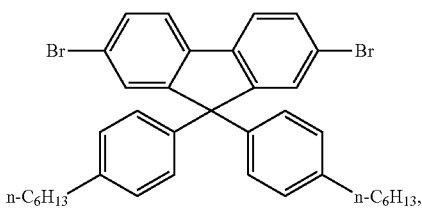
(M-2-BR)

the compound (0.997 g, 2.00 mmol) represented by the following formula (M-7-E):

[Chemical Formula 95]

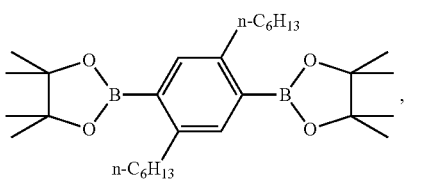
(M-7-E)

the compound (0.254 g, 0.40 mmol) represented by the following formula (M-8-BR):

[Chemical Formula 96]

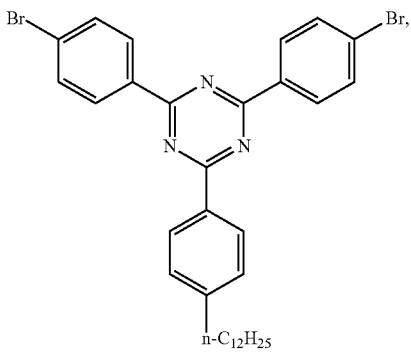
(M-8-BR)

palladium acetate (1.35 mg), tris(o-methoxy phenyl)phosphine (14.8 mg), and toluene (44 mL) were mixed, and heated to 105° C. A 20% by weight tetraethylammonium hydroxide aqueous solution (6.9 g) was dropped into the reaction solution, and refluxing was performed for 2 hours. After the reaction, phenyl boronic acid (24.4 mg) and toluene (5 mL) were added thereto, and refluxing was further performed for 2 hours. Next, a sodium diethyldithiocarbamate aqueous solution was added thereto, and stirring was performed at 80° C. for 2 hours. The obtained mixture was cooled, and toluene was prepared; the mixture was washed twice with water, twice with a 3% by weight acetic acid aqueous solution, and twice with water. The obtained solution was dropped into methanol, and filtered to obtain a precipitate. The precipitate was dissolved in toluene, and the solution was passed through an alumina column and a silica gel column sequentially; thereby, the solution was refined. The obtained solution was dropped into methanol, and stirred; the obtained precipitate was filtered out, and dried; thereby, 1.10 g of Polymer Compound A4 was obtained. The polystyrene-equivalent number-average molecular weight of Polymer Compound A4 was $8.2 \times 10^4$, and the polystyrene-equivalent weight-average molecular weight thereof was $2.22 \times 10^5$.

Synthesis Example 2: Synthesis of Polymer Compound AA

Synthesis of a polymer (Polymer Compound AA) having the constitutional unit represented by the following formula (K-101), the constitutional unit represented by the following formula (K-102), and the constitutional unit represented by the following formula (K-3) at a molar ratio of 42:8:50 (a theoretical value based on prepared raw materials) was performed as follows.

[Chemical Formula 97]

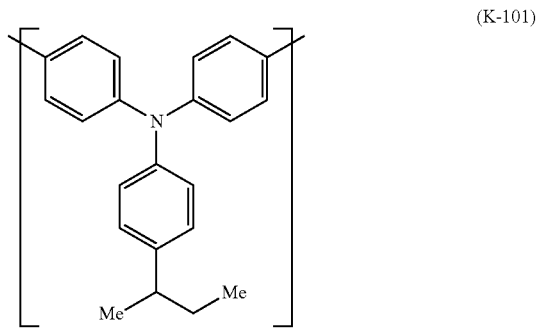
(K-101)

[Chemical Formula 98]

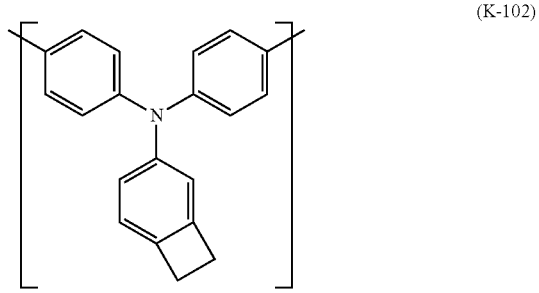
(K-102)

[Chemical Formula 99]

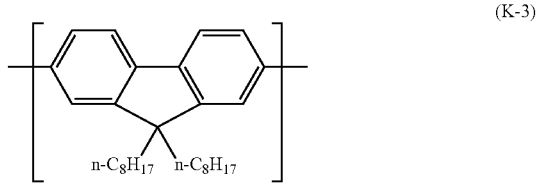
(K-3)

Under an argon atmosphere, the compound (17.57 g, 33.13 mmol) represented by the following formula (M-3-Z):

[Chemical Formula 100]

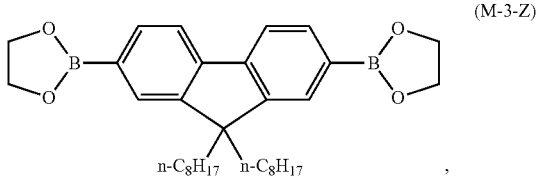

(M-3-Z)

the compound (12.88 g, 28.05 mmol) represented by the following formula (M-101-BR):

[Chemical Formula 101]

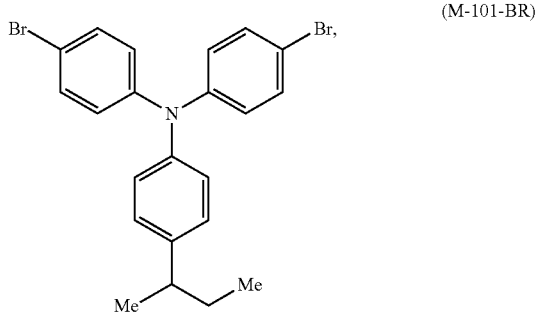

(M-101-BR)

the compound (2.15 g, 5.01 mmol) represented by the following formula (M-102-BR):

[Chemical Formula 102]

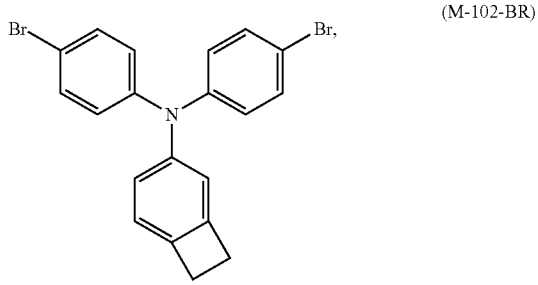

(M-102-BR)

palladium(II) acetate (7.4 mg), tris(2-methylphenyl)phosphine (70 mg), a 0.74M toluene solution of quaternary ammonium chloride (Aliquat (registered trademark 336, made by Sigma-Aldrich Corporation, 3 g), and toluene (200 g) were mixed.

A 18% by weight sodium carbonate aqueous solution (64 g) was dropped into the mixed liquid; the mixed liquid was heated for 3 hours or more and refluxed. After the reaction, phenylboronic acid (0.4 g) was added to the mixed liquid, and refluxing was further performed for 5 hours or more. Next, the reaction solution was diluted with toluene, and washed with a 3% by weight acetic acid aqueous solution and ion exchange water in this order; then, sodium diethyldithiocarbamate trihydrate (1.5 g) was added to the extracted organic layer, and stirred for 4 hours. The obtained solution was refined by column chromatography using an equivalent mixture of alumina and silica gel as a stationary phase. The obtained toluene solution was dropped into methanol, and stirred; the obtained precipitate was filtered out, and dried to obtain Polymer Compound AA. The polystyrene-equivalent number-average molecular weight of Polymer Compound AA was $8.9 \times 10^4$, and the polystyrene-equivalent weight-average molecular weight thereof was $4.2 \times 10^5$.

Example 7: Production and Evaluation of Light-Emitting Device 1

A film having a thickness of 35 nm was formed using a ethylene glycol monobutyl ether/water=3/2 (volume ratio) mixed liquid of polythiophenesulfonic acid (Sigma-Aldrich Corporation, trade name: Plexcore OC 1200) by spin coating on a glass substrate on which an ITO film having a thickness of 45 nm was formed by a sputtering method, and dried on a hot plate at 170° C. for 15 minutes.

Next, Polymer Compound AA was dissolved in xylene to prepare a 0.7% by weight xylene solution. By spin coating using the xylene solution, a film having a thickness of 20 nm was formed. This was heated on the hot plate in a nitrogen gas atmosphere at 180° C. for 60 minutes.

Next, Polymer Compound A1 was dissolved in xylene to prepare a 1.3% by weight xylene solution. By spin coating using the xylene solution, a film having a thickness of 65 nm was formed; the film was dried by heating in the nitrogen atmosphere at 130° C. for 10 hours; then, as the cathode, approximately 3 nm of sodium fluoride, and then approximately 80 nm of aluminum were vapor deposited to produce Light-Emitting Device 1. The vapor deposition of the metal was started after the degree of vacuum reached $1 \times 10^4$ Pa or less.

Voltage was applied to the obtained Light-Emitting Device 1; EL light emission having a peak at 445 nm was obtained from the device, and the maximum light emission efficiency was 6.3 cd/A. The results are shown in Table 1.

In the obtained Light-Emitting Device 1, the current value was set such that the initial luminance was 1000 cd/m$^2$; then, Light-Emitting Device 1 was driven at a constant current, and temporal change in luminance was measured. As a result, the luminance reduced by half after 46 hours. The result is shown in Table 1.

Example 8: Production and Evaluation of Light-Emitting Device 2

Light-Emitting Device 2 was produced in the same manner as in Example 7 except that Polymer Compound A2 was used instead of Polymer Compound A1 in Example 7. Voltage was applied to the obtained Light-Emitting Device 2; EL light emission having a peak at 450 nm was obtained from the device, and the maximum light emission efficiency was 7.4 cd/A. In the obtained Light-Emitting Device 2, the current value was set such that the initial luminance was 1000 cd/m$^2$; then, Light-Emitting Device 2 was driven at a constant current, and temporal change in luminance was measured. As a result, the luminance reduced by half after 134 hours. The result is shown in Table 1.

Example 9: Production and Evaluation of Light-Emitting Device 3

Light-Emitting Device 3 was produced in the same manner as in Example 7 except that Polymer Compound A3 was used instead of Polymer Compound A1 in Example 7. Voltage was applied to the obtained Light-Emitting Device 3; EL light emission having a peak at 465 nm was obtained from the device, and the maximum light emission efficiency was 10.8 cd/A. In the obtained Light-Emitting Device 3, the current value was set such that the initial luminance was 1000 cd/m$^2$; then, Light-Emitting Device 3 was driven at a constant current, and temporal change in luminance was measured. As a result, the luminance reduced by half after 640 hours. The results are shown in Table 1.

Example 10: Production and Evaluation of Light-Emitting Device 4

Light-Emitting Device 4 was produced in the same manner as in Example 7 except that instead of the xylene solution of Polymer Compound A1 in Example 7, a mixed solution in which a 1.3% by weight xylene solution of Polymer Compound A1 and a 1.3% by weight xylene solution of the compound represented by the following formula (T-1):

[Chemical Formula 103]

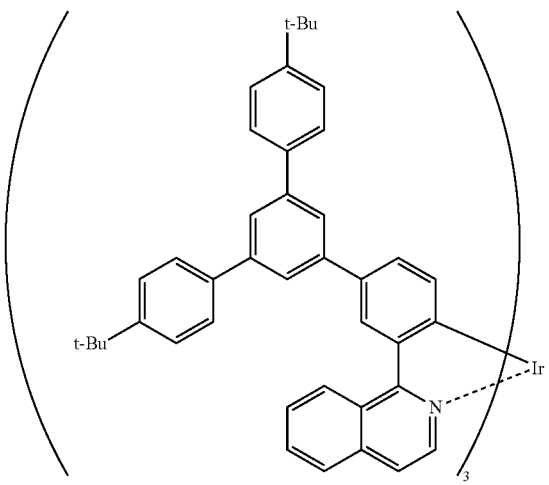

(T-1)

were mixed such that the weight ratio was 92.5:7.5 was used. Voltage was applied to the obtained Light-Emitting Device 4; EL light emission having a peak at 625 nm was obtained from the device, and the maximum light emission efficiency was 9.9 cd/A. In Light-Emitting Device 4 obtained above, the current value was set such that the initial luminance was 1000 cd/m$^2$; then, Light-Emitting Device 4 was driven at a constant current, and temporal change in luminance was measured. As a result, the luminance reduced by half after 7013 hours. The result is shown in Table 1.

Comparative Example 1: Synthesis of Polymer Compound B, and Production and Evaluation of Light-Emitting Device C1

Synthesis of a polymer (Polymer Compound B) having the constitutional unit represented by the following formula (K-9), the constitutional unit represented by the following formula (K-2), and the constitutional unit represented by the following formula (K-3) at a molar ratio of 5:50:45 (a theoretical value based on prepared raw materials) was performed as follows.

[Chemical Formula 104]

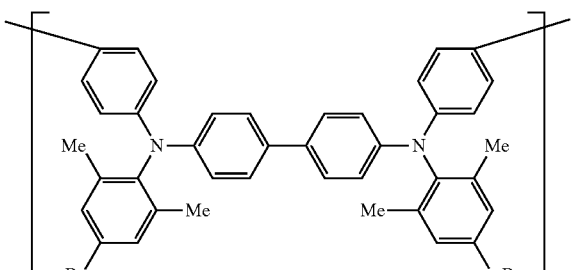

(K-9)

[Chemical Formula 105]

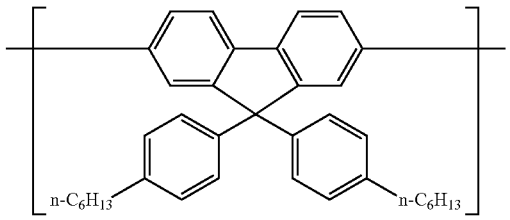

(K-2)

[Chemical Formula 106]

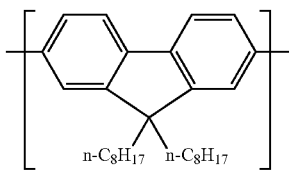

(K-3)

Under an argon atmosphere, the compound (0.326 g, 0.40 mmol) represented by the following formula (M-9-BR):

[Chemical Formula 107]

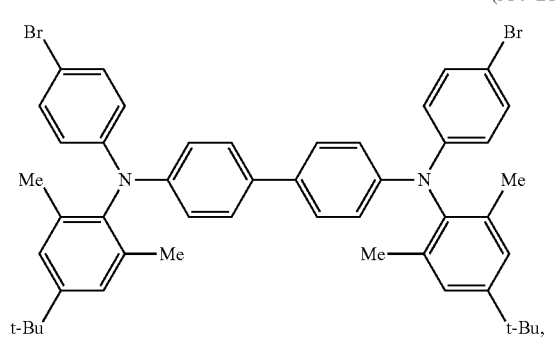

(M-9-BR)

the compound (2.955 g, 4.00 mmol) represented by the following formula (M-2-E):

[Chemical Formula 108]

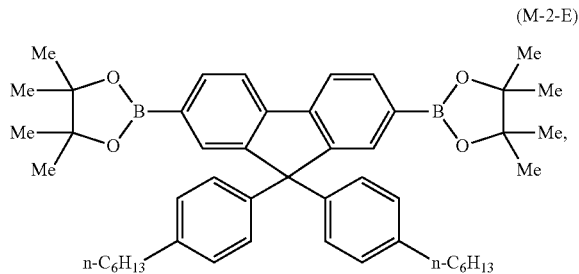

the compound (1.974 g, 3.60 mmol) represented by the following formula (M-3-BR):

[Chemical Formula 109]

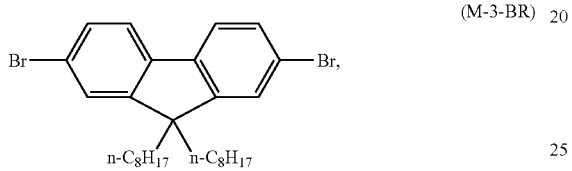

palladium acetate (2.7 mg), tris(o-methoxy phenyl)phosphine (29.6 mg), quaternary ammonium chloride (Aliquat (registered trademark) 336, made by Sigma-Aldrich Corporation, 0.52 g), and toluene (40 mL) were mixed, and heated to 105° C.

A 17.5% by weight sodium carbonate (10.9 mL) was dropped into the reaction solution, and refluxing was performed for 2.5 hours. After the reaction, phenyl boronic acid (50 mg) and toluene (5 mL) were added thereto, and refluxing was further performed for 2 hours. Next, a sodium diethyldithiocarbamate aqueous solution was added thereto, and stirring was performed at 80° C. for 2 hours. The obtained mixture was cooled, and toluene was prepared; the mixture was washed twice with water, twice with a 3% by weight acetic acid aqueous solution, and twice with water. The obtained solution was dropped into methanol, and filtered to obtain a precipitate. The precipitate was dissolved in toluene, and the solution was passed through an alumina column and a silica gel column sequentially; thereby, the solution was refined. The obtained solution was dropped into methanol, and stirred; the obtained precipitate was filtered out, and dried; thereby, 2.04 g of Polymer Compound B was obtained. The polystyrene-equivalent number-average molecular weight of Polymer Compound B was $1.30 \times 10^5$, and the polystyrene-equivalent weight-average molecular weight thereof was $3.20 \times 10^5$.

Light-Emitting Device C1 was produced in the same manner as in Example 7 except that Polymer Compound B was used instead of Polymer Compound A1 in Example 7. Voltage was applied to the obtained Light-Emitting Device C1; EL light emission having a peak at 440 nm was obtained from the device, and the maximum light emission efficiency was 5.6 cd/A. In the obtained Light-Emitting Device C1, the current value was set such that the initial luminance was 1000 cd/m², then, Light-Emitting Device C1 was driven at a constant current, and temporal change in luminance was measured. As a result, the luminance reduced by half after 29 hours. The results are shown in Table 1.

Comparative Example 2: Synthesis of Polymer Compound C, And, Production and Evaluation of Light-Emitting Device C2

Synthesis of a polymer (Polymer Compound C) having the constitutional unit represented by the following formula (K-10), the constitutional unit represented by the following formula (K-2), and the constitutional unit represented by the following formula (K-3) at a molar ratio of 5:50:45 (a theoretical value based on prepared raw materials) was performed as follows.

[Chemical Formula 110]

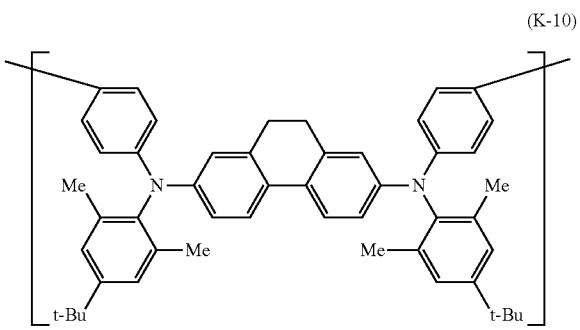

[Chemical Formula 111]

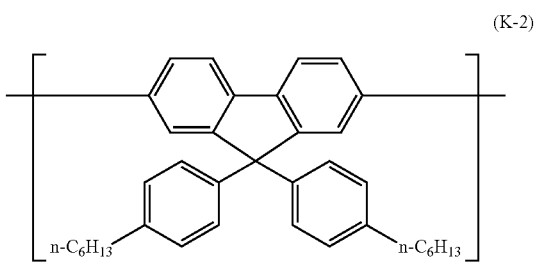

[Chemical Formula 112]

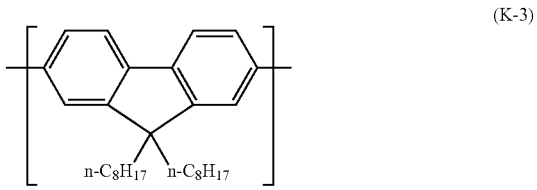

Under an argon atmosphere, the compound (0.168 g, 0.20 mmol) represented by the following formula (M-10-BR):

[Chemical Formula 113]

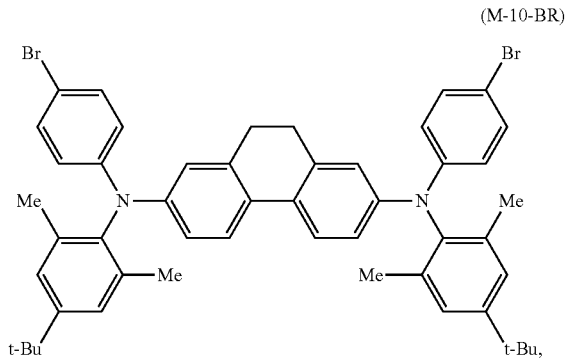

the compound (1.477 g, 2.00 mmol) represented by the following formula (M-2-E):

[Chemical Formula 114]

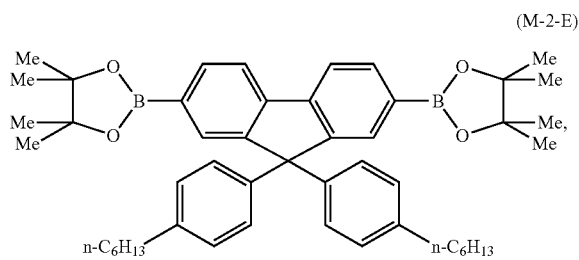

(M-2-E)

the compound (0.987 g, 1.80 mmol) represented by the following formula (M-3-BR):

[Chemical Formula 115]

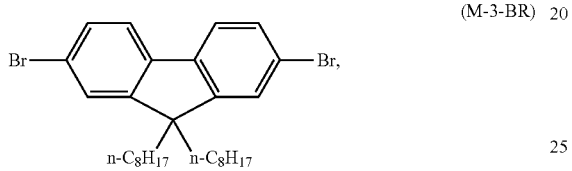

(M-3-BR)

palladium acetate (1.35 mg), tris(o-methoxy phenyl)phosphine (14.8 mg), and toluene (44 mL) were mixed, and heated to 105° C. A 20% by weight tetraethylammonium hydroxide aqueous solution (6.9 g) was dropped into the reaction solution, and refluxing was performed for 3 hours.

After the reaction, phenyl boronic acid (24.4 mg) and toluene (5 mL) were added thereto, and refluxing was further performed for 18 hours. Next, a sodium diethyldithiocarbamate aqueous solution was added thereto, and stirring was performed at 80° C. for 2 hours. The obtained mixture was cooled, and toluene was prepared; the mixture was washed twice with water, twice with a 3% by weight acetic acid aqueous solution, and twice with water. The obtained solution was dropped into methanol, and filtered to obtain a precipitate. The precipitate was dissolved in toluene, and the solution was passed through an alumina column and a silica gel column sequentially; thereby, the solution was refined. The obtained solution was dropped into methanol, and stirred; the obtained precipitate was filtered out, and dried; thereby, 1.28 g of Polymer Compound C was obtained. The polystyrene-equivalent number-average molecular weight of Polymer Compound C was $7.8 \times 10^4$, and the polystyrene-equivalent weight-average molecular weight thereof was $2.16 \times 10^5$.

Light-Emitting Device C2 was produced in the same manner as in Example 7 except that Polymer Compound C was used instead of Polymer Compound A1 in Example 7. Voltage was applied to the obtained Light-Emitting Device C2; EL light emission having a peak at 445 nm was obtained from the device, and the maximum light emission efficiency was 4.7 cd/A. In the obtained Light-Emitting Device C2, the current value was set such that the initial luminance was 1000 cd/m$^2$; then, Light-Emitting Device C2 was driven at a constant current, and temporal change in luminance was measured. As a result, the luminance reduced by half after less than 1 hours. The results are shown in Table 1.

Comparative Example 3: Production and Evaluation of Light-Emitting Device C3

Light-Emitting Device C3 was produced in the same manner as in Example 7 except that instead of the xylene solution of Polymer Compound A1 in Example 7, a mixed solution in which a 1.3% by weight xylene solution of Polymer Compound B and a 1.3% by weight xylene solution of the compound represented by the above formula (T-1) were mixed such that the weight ratio was 92.5:7.5 was used. Voltage was applied to the obtained Light-Emitting Device C3; EL light emission having a peak at 625 nm was obtained from the device, and the maximum light emission efficiency was 8.8 cd/A. In Light-Emitting Device C3 obtained above, the current value was set such that the initial luminance was 1000 cd/m$^2$; then, Light-Emitting Device C3 was driven at a constant current, and temporal change in luminance was measured. As a result, the luminance reduced by half after 4039 hours. The result is shown in Table 1.

TABLE 1

| Light-emitting device | Polymer compound | Triplet light-emitting complex | The maximum light emission efficiency (cd/A) | Light emission peak wavelength (nm) | Luminance half-decay lifetime (hours) |
| --- | --- | --- | --- | --- | --- |
| Example 7 | 1 | A1 | — | 6.3 | 445 | 46 |
| Example 8 | 2 | A2 | — | 7.4 | 450 | 134 |
| Example 9 | 3 | A3 | — | 10.8 | 465 | 640 |
| Example 10 | 4 | A1 | T1 | 9.9 | 625 | 7013 |
| Comparative Example 1 | C1 | B | — | 5.6 | 440 | 29 |
| Comparative Example 2 | C2 | C | — | 4.7 | 445 | Less than 1 hour |
| Comparative Example 3 | C3 | B | T1 | 8.8 | 625 | 4039 |

Examples 7, 8, and 9 correspond to Comparative Examples 1 and 2. In Table 1 above, Example 10 corresponds to Comparative Example 3. Apparently from Table 1 above, it turns out that the polymer compound according to the present invention is useful for production of the light-emitting device which is excellent in luminance life.

REFERENCE SIGNS LIST

10 . . . substrate, 11 . . . anode, 12 . . . hole injection layer, 13 . . . hole transport layer, 14 . . . light-emitting layer, 15 . . . electron transport layer, 16 . . . electron injection layer, 17 . . . cathode, 20 . . . substrate, 21 . . . anode, 22 . . . hole injection layer, 23 . . . light-emitting layer, 24 . . . cathode, 25 . . . protective layer, 100 . . . light-emitting device, 110 . . . light-emitting device, 200 . . . surface lighting source.

The invention claimed is:

1. A polymer compound comprising a constitutional unit represented by the following formula (1):

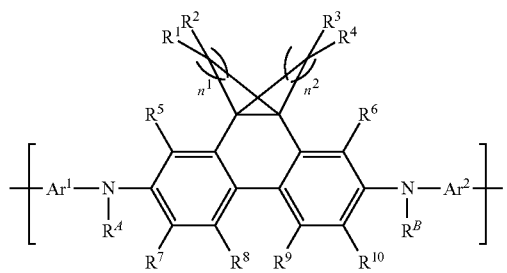

(1)

wherein $n^1$ and $n^2$ each independently represent an integer of 1 to 5;

$R^1$, $R^2$, $R^3$, $R^4$, $R^5$, $R^6$, $R^7$, $R^8$, $R^9$, and $R^{10}$ each independently represent a hydrogen atom, an unsubstituted or substituted alkyl group, an unsubstituted or substituted alkoxy group, an unsubstituted or substituted aryl group, an unsubstituted or substituted aryloxy group, or an unsubstituted or substituted monovalent heterocyclic group;

$R^A$ and $R^B$ each independently represent a hydrogen atom, an unsubstituted or substituted alkyl group, an unsubstituted or substituted aryl group, or an unsubstituted or substituted monovalent heterocyclic group;

$Ar^1$ and $Ar^2$ each independently represent an unsubstituted or substituted arylene group, an unsubstituted or substituted divalent heterocyclic group, or a divalent group in which two or more same or different optionally substituted groups selected from the group consisting of arylene groups and divalent heterocyclic groups are linked;

when $R^1$, $R^2$, $R^3$, and $R^4$ exist in plural, the plurality of $R^1$, $R^2$, $R^3$, or $R^4$ can be the same or different from each other; among $R^1$, $R^2$, $R^3$, and $R^4$, adjacent groups can be linked to each other to form a ring structure; among $R^7$, $R^8$, $R^9$ and $R^{10}$, adjacent groups can be linked to each other to form a ring structure; $Ar^1$ and $R^A$ can be linked to each other to form a ring structure; and $Ar^2$ and $R^B$ can be linked to each other to form a ring structure, wherein the polymer compound further comprises a constitutional unit represented by the following formula (2):

(2)

wherein $Ar^3$ represents an unsubstituted or substituted arylene group, an unsubstituted or substituted divalent heterocyclic group, or a divalent group in which two or more same or different optionally substituted groups selected from the group consisting of arylene groups and divalent heterocyclic groups are linked, and wherein a content of the constitutional unit represented by the formula (1) is 0.1 mol % to 5 mol % of the total constitutional units in the polymer compound.

2. The polymer compound according to claim 1, wherein at least one of the constitutional units represented by the formula (2) is a constitutional unit consisting of an unsubstituted or substituted fluorenediyl group.

3. The polymer compound according to claim 2, wherein at least one of the constitutional units represented by the formula (2) is a constitutional unit consisting of an unsubstituted or substituted 2,7-fluorenediyl group.

4. The polymer compound according to claim 1, wherein at least one of the constitutional units represented by the formula (2) is a constitutional unit consisting of at least one group selected from the group consisting of an unsubstituted or substituted phenylene group, an unsubstituted or substituted naphthalenediyl group, an unsubstituted or substituted anthracenediyl group, and groups represented by the following formula (3'):

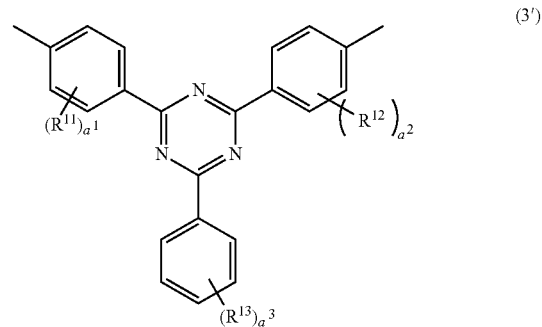

(3')

wherein $a^1$ and $a^2$ each independently represent an integer of 0 to 4; $a^3$ represents an integer of 0 to 5;

$R^{11}$, $R^{12}$, and $R^{13}$ each independently represent an unsubstituted or substituted alkyl group, an unsubstituted or substituted alkoxy group, an unsubstituted or substituted aryl group, an unsubstituted or substituted aryloxy group, an unsubstituted or substituted monovalent heterocyclic group, an unsubstituted or substituted alkoxycarbonyl group, an unsubstituted or substituted silyl group, a halogen atom, a carboxyl group, or a cyano group; and when $R^{11}$, $R^{12}$, $R^{13}$, and $R^{14}$ exist in plural, the plurality of $R^{11}$, $R^{12}$, $R^{13}$, or $R^{14}$ can be the same or different from each other.

5. The polymer compound according to claim 1, further comprising a constitutional unit represented by the following formula (4):

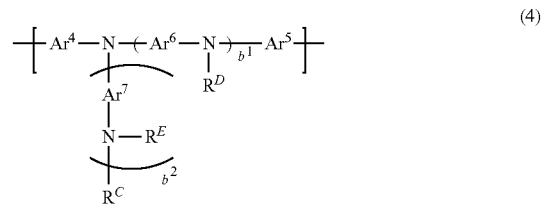

(4)

wherein $b^1$ and $b^2$ each independently represent 0 or 1;

$Ar^4$, $Ar^5$, $Ar^6$, and $Ar^7$ each independently represent an unsubstituted or substituted arylene group, an unsubstituted or substituted divalent heterocyclic group, or a divalent group in which two or more same or different optionally substituted groups selected from the group consisting of arylene groups and divalent heterocyclic groups are linked;

R$^C$, R$^D$, and R$^E$ each independently represent a hydrogen atom, an unsubstituted or substituted alkyl group, an unsubstituted or substituted aryl group, or an unsubstituted or substituted monovalent heterocyclic group;

Ar$^4$, Ar$^5$, Ar$^6$, and Ar$^7$ each can be linked to a group other than the group to form a ring structure, the other group being bonded to a nitrogen atom to which the group is bonded; and the constitutional unit represented by the formula (4) is different from the constitutional unit represented by the formula (1).

6. The polymer compound according to claim 5, wherein at least one of the constitutional units represented by the formula (4) is a constitutional unit represented by the following formula (5):

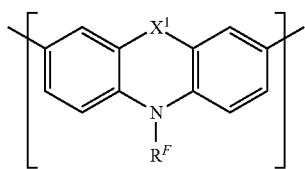

(5)

wherein R$^F$ represents a hydrogen atom, an unsubstituted or substituted alkyl group, an unsubstituted or substituted aryl group, or an unsubstituted or substituted monovalent heterocyclic group;

X$^1$ represents a single bond, an oxygen atom, a sulfur atom, or a group represented by —C(R$^{14}$)$_2$—, wherein R$^{14}$ represents an unsubstituted or substituted alkyl group or an unsubstituted or substituted aryl group, and a plurality of R$^{14}$ can be the same or different from each other.

7. The polymer compound according to claim 5, comprising the constitutional unit represented by the formula (1), the constitutional unit represented by formula (2), the constitutional unit represented by the formula (4), a constitutional unit consisting of an unsubstituted or substituted fluorenediyl group, and a constitutional unit represented by an unsubstituted or substituted phenylene group.

8. The polymer compound according to claim 5, comprising the constitutional unit represented by the formula (1), the constitutional unit represented by formula (2), the constitutional unit represented by the formula (4), a constitutional unit consisting of an unsubstituted or substituted fluorenediyl group, and a constitutional unit consisting of an unsubstituted or substituted naphthalenediyl group.

9. The polymer compound according to claim 5, comprising the constitutional unit represented by the formula (1), the constitutional unit represented by formula (2), the constitutional unit represented by the formula (4), a constitutional unit consisting of an unsubstituted or substituted fluorenediyl group, and a constitutional unit consisting of an unsubstituted or substituted anthracenediyl group.

10. The polymer compound according to claim 5, comprising the constitutional unit represented by the formula (1), the constitutional unit represented by formula (2), the constitutional unit represented by the formula (4), a constitutional unit consisting of an unsubstituted or substituted fluorenediyl group, and a constitutional unit represented by the following formula (3):

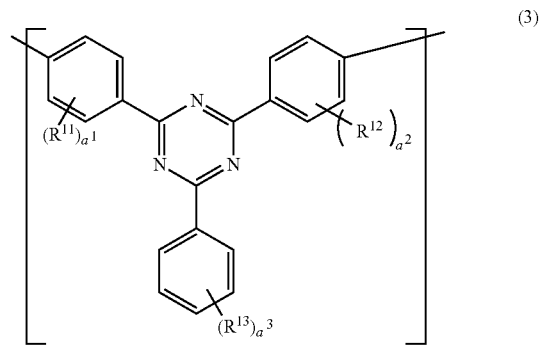

(3)

wherein a$^1$ and a$^2$ each independently represent an integer of 0 to 4; a$^3$ represents an integer of 0 to 5;

R$^{11}$, R$^{12}$, and R$^{13}$ each independently represent an unsubstituted or substituted alkyl group, an unsubstituted or substituted alkoxy group, an unsubstituted or substituted aryl group, an unsubstituted or substituted aryloxy group, an unsubstituted or substituted monovalent heterocyclic group, an unsubstituted or substituted alkoxycarbonyl group, an unsubstituted or substituted silyl group, a halogen atom, a carboxyl group, or a cyano group; and when R$^{11}$, R$^{12}$, R$^{13}$, and R$^{14}$ exist in plural, the plurality of R$^{11}$, R$^{12}$, R$^{13}$, or R$^{14}$ can be the same or different from each other.

11. The polymer compound according to claim 1, wherein n$^1$ and n$^2$ in the formula (1) each independently represent 3 or 4.

12. The polymer compound according to claim 11, wherein R$^A$ and R$^B$ in the formula (1) each independently represent an unsubstituted or substituted aryl group or an unsubstituted or substituted monovalent heterocyclic group.

13. The polymer compound according to claim 1, wherein the polymer compound is synthesized by condensation polymerization of a monomer (1) that introduces the constitutional unit represented by the formula (1) with a monomer (X) that introduces a constitutional unit different from the constitutional unit represented by the formula (1), and when the number of the monomer (1) is N$_1$ and the number of the monomer (X) is N$_X$, N$_1$ and N$_X$ satisfy the following equation (I):

$$0.1 \leq N_1 \times 100/(N_1+N_X) \leq 5 \qquad (I).$$

14. A composition comprising the polymer compound according to claim 1, and at least one selected from the group consisting of a hole transport material, an electron transport material, and a light-emitting material.

15. The composition according to claim 14, comprising a triplet light-emitting complex as the light-emitting material.

16. A liquid composition comprising the polymer compound according to claim 1, and a solvent.

17. An organic film comprising the polymer compound according to claim 1.

18. An organic film prepared using the composition according to claim 14.

19. A light-emitting device having the organic film according to claim 17.

20. A surface lighting source having the light-emitting device according to claim 19.

21. A display device having the light-emitting device according to claim 19.

22. The polymer compound according to claim 12, wherein $R^1$, $R^2$, $R^3$, and $R^4$ each independently represent a hydrogen atom, or an unsubstituted or substituted alkyl group.

23. The polymer compound according to claim 22, wherein $R^5$, $R^6$, $R^7$, $R^8$, $R^9$, and $R^{10}$ each independently represent a hydrogen atom, an unsubstituted or substituted alkyl group, or an unsubstituted or substituted aryl group.

24. The polymer compound according to claim 23, wherein $Ar^1$ and $Ar^2$ each independently represent an unsubstituted or substituted arylene group, or an unsubstituted or substituted divalent heterocyclic group.

* * * * *